United States Patent
Dzhekiev et al.

(10) Patent No.: US 12,383,160 B2
(45) Date of Patent: Aug. 12, 2025

(54) SYSTEM AND METHOD FOR AUTOMATIC DETECTION OF DISEASE-ASSOCIATED RESPIRATORY SOUNDS

(71) Applicant: Insubiq Inc., Wilmington, DE (US)

(72) Inventors: Igor Dzhekiev, Moscow (RU); Eugene Nikolaev, Cheboksary (RU)

(73) Assignee: Insubiq Inc., Newtown, PA (US)

( * ) Notice: Subject to any disclaimer, the term of this patent is extended or adjusted under 35 U.S.C. 154(b) by 0 days.

(21) Appl. No.: 17/516,376

(22) Filed: Nov. 1, 2021

(65) Prior Publication Data
US 2022/0338756 A1    Oct. 27, 2022

Related U.S. Application Data

(60) Provisional application No. 63/108,763, filed on Nov. 2, 2020.

(51) Int. Cl.
| | |
|---|---|
| A61B 5/08 | (2006.01) |
| A61B 5/00 | (2006.01) |
| A61B 7/00 | (2006.01) |
| G10L 21/0308 | (2013.01) |
| G10L 25/18 | (2013.01) |
| G10L 25/66 | (2013.01) |

(52) U.S. Cl.
CPC .......... *A61B 5/0823* (2013.01); *A61B 5/7267* (2013.01); *A61B 5/7282* (2013.01);
(Continued)

(58) Field of Classification Search
CPC ... A61B 5/0823; A61B 5/7267; A61B 5/7282; A61B 7/003; A61B 5/7264; A61B 5/6898; A61B 5/7253; A61B 2560/0223; A61B 2562/0247; A61B 5/1038; A61B 5/112; A61B 5/6807; A61B 5/7225;
(Continued)

(56) References Cited

U.S. PATENT DOCUMENTS

| | | | |
|---|---|---|---|
| 6,168,568 B1 * | 1/2001 | Gavriely | A61B 5/087 600/529 |
| 6,182,018 B1 * | 1/2001 | Tran | G06F 18/00 324/76.12 |

(Continued)

FOREIGN PATENT DOCUMENTS

WO    WO-2013142908 A1 * 10/2013 .......... A61B 5/0803

*Primary Examiner* — Alex M Valvis
*Assistant Examiner* — Jonathan E. Cooper
(74) *Attorney, Agent, or Firm* — Hoffberg & Associates; Steven M. Hoffberg

(57) ABSTRACT

A method to detect and analyze cough parameters remotely and in the background through the user's device in everyday life. The method involves consecutive or selective execution of 4 stages, which solve a variety of the following tasks: Detection of coughing events in sound, in environmental noise. Separation of the sound containing the cough into the sound of the cough and the rest of the sounds, even when extraneous sounds occurred during the cough. Identify the user by the sound of the cough to prevent analyzing the sounds of the cough that do not belong to the user (for example when another person coughs nearby). Assessment of cough characteristics (wet/dry, severity, duration, number of spasms, etc.). The method can work on wearable devices, smart devices, personal computers, laptops in 24/7 mode or in a selected range of time, and has a high energy efficiency.

20 Claims, 10 Drawing Sheets

(52) U.S. Cl.
CPC .......... *A61B 7/003* (2013.01); *G10L 21/0308* (2013.01); *G10L 25/18* (2013.01); *G10L 25/66* (2013.01)

(58) Field of Classification Search
CPC ......... A61B 5/0022; A61B 5/01; A61B 5/021; A61B 5/145; A61B 5/024; A61B 5/1455; A61B 5/726; A61B 5/7203; A61B 5/38; G10L 21/0308; G10L 25/18; G10L 25/66
USPC .......................................................... 600/529
See application file for complete search history.

(56) References Cited

U.S. PATENT DOCUMENTS

| | | | |
|---|---|---|---|
| 9,282,898 B2* | 3/2016 | McRoberts | G16H 40/67 |
| 11,504,011 B1* | 11/2022 | Jain | G06N 5/04 |
| 2009/0319265 A1* | 12/2009 | Wittenstein | G10L 15/26 |
| | | | 704/E15.015 |
| 2012/0302898 A1* | 11/2012 | Zhang | A61B 5/0823 |
| | | | 607/18 |
| 2014/0310739 A1* | 10/2014 | Ricci | G06F 3/013 |
| | | | 725/75 |
| 2014/0336537 A1* | 11/2014 | Patel | A61B 5/0816 |
| | | | 600/586 |
| 2019/0073489 A1* | 3/2019 | Amschler | H04L 9/0833 |
| 2019/0105011 A1* | 4/2019 | Kim | G06F 18/295 |
| 2019/0192047 A1* | 6/2019 | Stamatopoulos | A61B 7/003 |
| 2019/0298224 A1* | 10/2019 | Rahman | A61B 5/0816 |
| 2020/0245873 A1* | 8/2020 | Frank | A61B 5/0823 |
| 2021/0319804 A1* | 10/2021 | Whitehill | G06N 3/044 |
| 2021/0338103 A1* | 11/2021 | Imran | A61B 5/7267 |
| 2022/0008030 A1* | 1/2022 | Sunshine | G10L 25/66 |
| 2022/0409089 A1* | 12/2022 | den Brinker | G16H 50/20 |

* cited by examiner

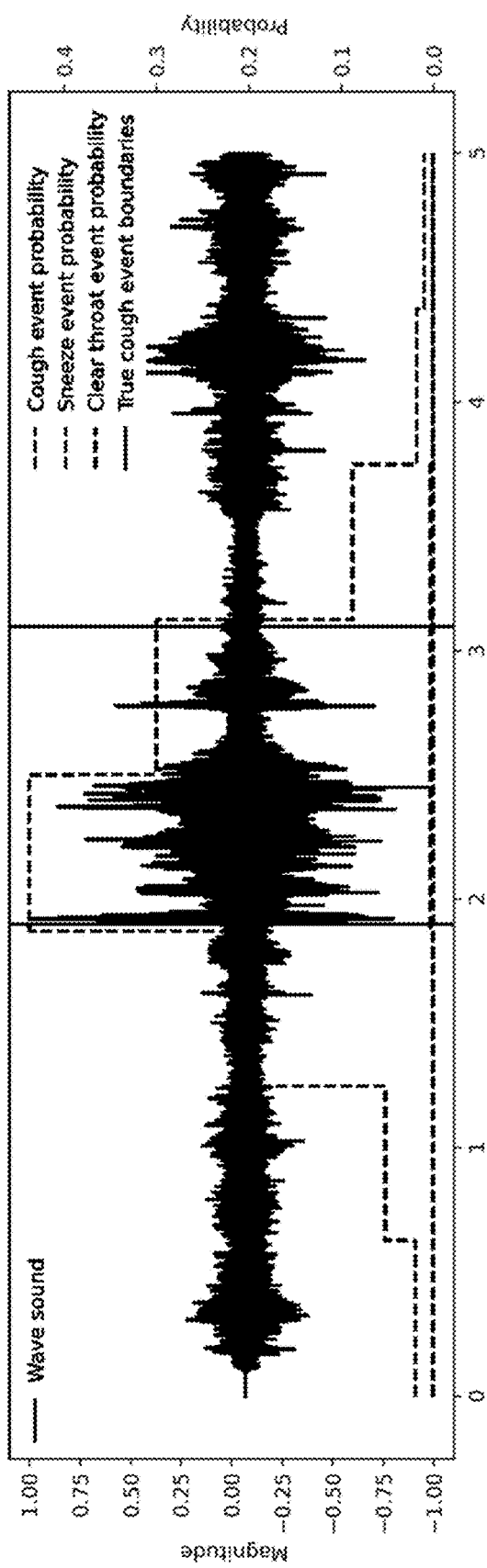
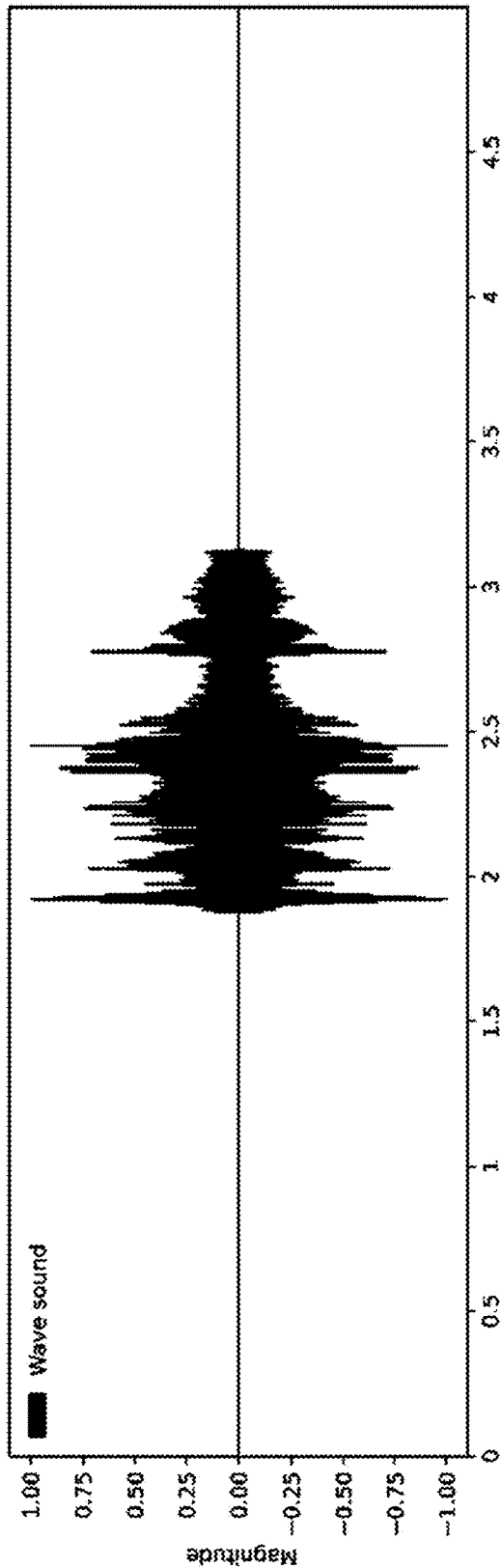
Fig. 8A
Fig. 8B

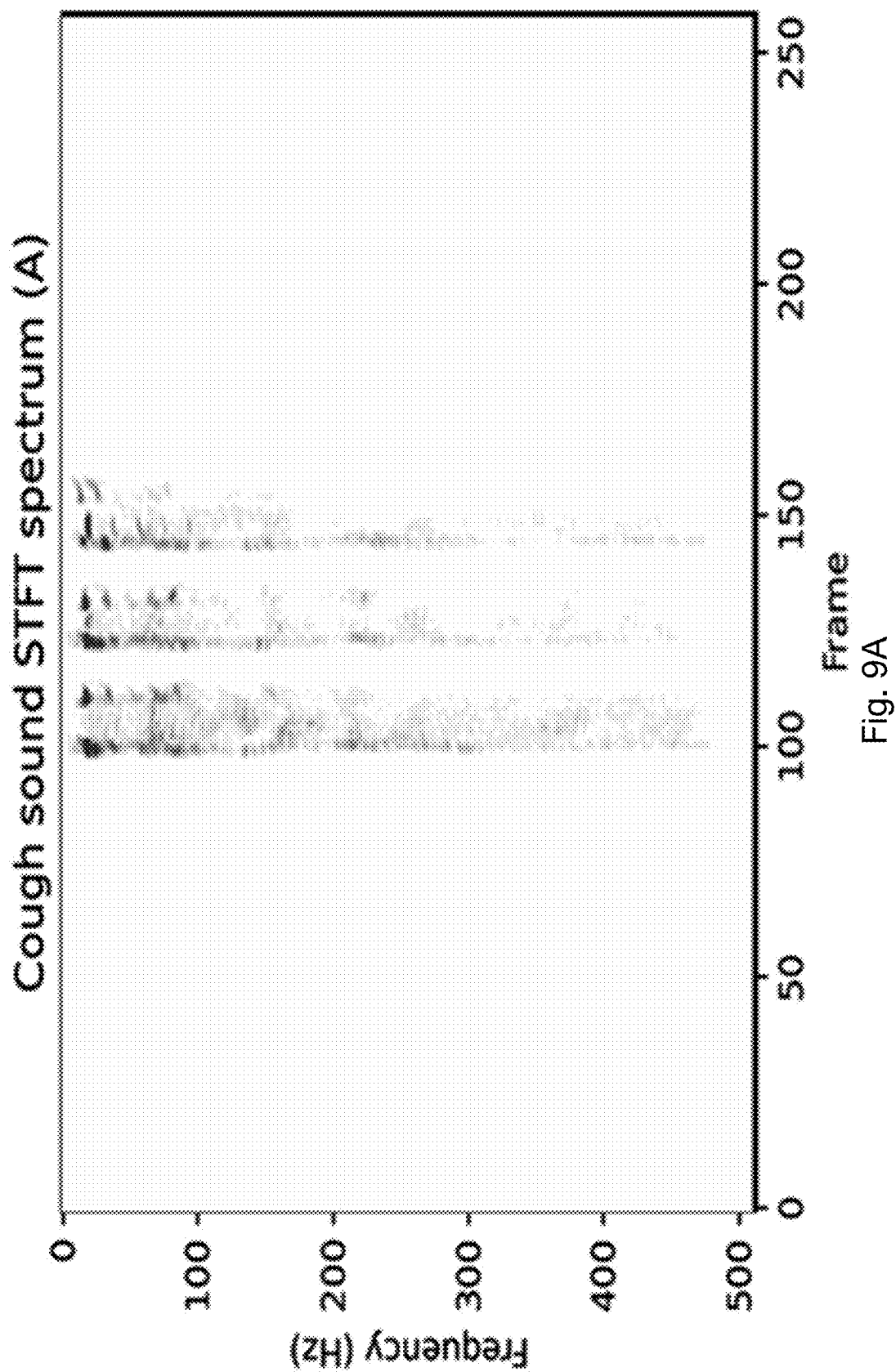

SYSTEM AND METHOD FOR AUTOMATIC DETECTION OF DISEASE-ASSOCIATED RESPIRATORY SOUNDS

CROSS REFERENCE TO RELATED APPLICATION

The present application is a non-provisional of, and claims benefit of priority under 35 U.S.C. § 119(e) from U.S. Provisional Patent Application No. 63/108,763, filed Nov. 2, 2020, the entirety of which is expressly incorporated herein by reference.

FIELD OF THE INVENTION

The present invention relates to the field of automated analysis of acoustic signatures, and, in particular, of cough and other respiratory indicia of disease.

BACKGROUND OF THE INVENTION

Each reference cited herein is expressly incorporated herein by reference in its entirety. Note that citation of a reference herein is not an admission that the reference is prior art to the invention as claimed.

Coronavirus disease 2019 (COVID-19) is a contagious disease caused by severe acute respiratory syndrome coronavirus 2 (SARS-CoV-2). The first known case was identified in Wuhan, China, in December 2019. The disease has since spread worldwide, leading to an ongoing pandemic.

Symptoms of COVID-19 are variable, but often include fever, cough, headache, fatigue, breathing difficulties, and loss of smell and taste. Symptoms may begin one to fourteen days after exposure to the virus. At least a third of people who are infected do not develop noticeable symptoms. Of those people who develop symptoms noticeable enough to be classed as patients, most (81%) develop mild to moderate symptoms (up to mild pneumonia), while 14% develop severe symptoms (dyspnea, hypoxia, or more than 50% lung involvement on imaging), and 5% suffer critical symptoms (respiratory failure, shock, or multiorgan dysfunction). Older people are at a higher risk of developing severe symptoms. Some people continue to experience a range of effects (long COVID) for months after recovery, and damage to organs has been observed. Multi-year studies are underway to further investigate the long-term effects of the disease.

COVID-19 transmits when people breathe in air contaminated by droplets and small airborne particles containing the virus. The risk of breathing these in is highest when people are in close proximity, but they can be inhaled over longer distances, particularly indoors. Transmission can also occur if splashed or sprayed with contaminated fluids in the eyes, nose or mouth, and, rarely, via contaminated surfaces. People remain contagious for up to 20 days, and can spread the virus even if they do not develop symptoms.

The disease is mainly transmitted via the respiratory route when people inhale droplets and small airborne particles (that form an aerosol) that infected people breath out as they breathe, talk, cough, sneeze, or sing. Infected people are more likely to transmit COVID-19 when they are physically close. However, infection can occur over longer distances, particularly indoors.

Infectivity can occur 1-3 days before the onset of symptoms. Infected persons can spread the disease even if they are pre-symptomatic or asymptomatic. Most commonly, the peak viral load in upper respiratory tract samples occurs close to the time of symptom onset and declines after the first week after symptoms begin. Current evidence suggests a duration of viral shedding and the period of infectiousness of up to 10 days following symptom onset for persons with mild to moderate COVID-19, and a up to 20 days for persons with severe COVID-19, including immunocompromised persons.

Infectious particles range in size from aerosols that remain suspended in the air for long periods of time to larger droplets that remain airborne or fall to the ground. Additionally, COVID-19 research has redefined the traditional understanding of how respiratory viruses are transmitted. The largest droplets of respiratory fluid do not travel far, and can be inhaled or land on mucous membranes on the eyes, nose, or mouth to infect. Aerosols are highest in concentration when people are in close proximity, which leads to easier viral transmission when people are physically close, but airborne transmission can occur at longer distances, mainly in locations that are poorly ventilated; in those conditions small particles can remain suspended in the air for minutes to hours.

The number of people generally infected by one infected person varies; as only 10 to 20% of people are responsible for the disease's spread. It often spreads in clusters, where infections can be traced back to an index case or geographical location. Often in these instances, superspreading events occur, where many people are infected by one person.

A number of systems are proposed for detecting cough with a smartphone, and for diagnosing the etiology of the detected cough. See: U.S. Pat. No. 10,786,395; 10,803,714; 10,823,746; 10,842,896; 10,880,303; 10,887,104; 10,902,955; 10,906,180; 10,917,429; 10,922,631; 10,927,404; 10,937,296; 10,987,067; 10,991,185; 10,991,190; 10,991,463; 10,997,325; 11,000,191; 11,006,843; 11,011,258; 11,011,278; 11,013,472; 11,013,639; 11,017,688; 11,024,339; 11,030,708; 11,038,914; 11,045,271; 11,053,556; 11,056,242; 11,057,689; 11,080,607; 11,080,981; 11,087,054; 11,089,262; 11,093,671; 11,096,059; 20200230408; 20200269097; 20200273578; 20200279339; 20200279464; 20200279585; 20200294680; 20200305265; 20200321007; 20200322917; 20200338304; 20200350989; 20200352456; 20200357512; 20200358762; 20200367040; 20200380957; 20200381130; 20200388287; 20200388382; 20200390402; 20200397341; 20210003528; 20210005324; 20210008309; 20210018210; 20210018212; 20210020294; 20210022536; 20210033586; 20210036678; 20210047165; 20210050116; 20210052221; 20210058736; 20210060391; 20210073430; 20210073433; 20210073434; 20210073435; 20210073440; 20210073441; 20210073442; 20210073446; 20210073447; 20210073448; 20210073449; 20210073736; 20210076932; 20210077010; 20210077762; 20210082583; 20210092114; 20210096656; 20210102197; 20210105353; 20210106238; 20210107008; 20210110736; 20210110919; 20210113723; 20210116376; 20210116377; 20210116378; 20210116384; 20210116449; 20210117642; 20210120193; 20210121062; 20210123921; 20210128021; 20210128762; 20210132035; 20210134463; 20210142874; 20210151136; 20210151172; 20210151198; 20210152910; 20210154343; 20210158378; 20210166819; 20210169422; 20210173711; 20210173854; 20210177266; 20210178217; 20210183278; 20210183515; 20210183523; 20210197834; 20210202098; 20210202099; 20210202100; 20210202101; 20210202102; 20210202103; 20210202104; 20210202105; 20210202106; 20210202107; 20210204886; 20210204887; 20210208062; 20210209523; 20210210170; 20210210207; 20210225519; 20210225520; 20210225521; 20210225522; 20210233631; 20210241395; 20210241901; 20210241918; 20210241923; 20210244365;

20210251191; 20210251497; 20210256180; 20210256439; 20210256833; 20210257004; 20210257074; 20210257104; 20210258756; AU2020101374; AU2020323954; AU2020323954; AU2021200000; AU2021203016; CA3104257; CN112117012; CN112117012; CN112188405; CN112188405; CN112675324; CN112869259; CN113141572; CN213373949; CN213404956; DE202020001414; DE202020004514; DE202020004603; DE202020102240; DE202020103629; DE202020104079; DE202020104376; DE202020104542; DE202020105375; DE202021000267; DE202021001238; DE202021100976; DE202021102756; ES1254484; ES1255880; ES1260754; ES1275216; IL274446; IN202011013950; IN202011015845; IN202011024379; IN202011028610; IN202011029521; IN202011048046; IN202011048322; IN202011050693; IN202011053168; IN202011053957; IN202021039996; IN202021053503; IN202031019682; IN202031024977; IN202041026465; IN202041043302; IN202041056246; IN202111001305; IN202111001797; IN202111002806; IN202111002823; IN202111003926; IN202111021143; IN202111026825; IN202141002214; IN202141027048; IN202141028360; JP3230579; JP6830285; JP6889963; JP6889964; JP6889965; KR102160589; KR102166497; KR102181197; KR102188384; KR102197383; KR102202140; KR102209329; KR102209435; KR102216783; KR102224469; KR102231505; KR102232966; KR102234025; KR102241569; KR102247752; KR102248320; KR102255483; KR102256959; KR102271921; KR102272576; KR102272654; KR102278186; KR102282092; KR102282352; KR102284675; KR102295660; KR20200047457; KR20210030855; RU204085; RU2735400C1; RU2735722C1; RU2748960C1; RU2749725C1; RU2752137C1; WO2020236481; WO2020243701; WO2020257291; WO2021011762; WO2021016391; WO2021026460; WO2021026606; WO2021034859; WO2021041187; WO2021044150; WO2021044160; WO2021044216; WO2021050343; WO2021050910; WO2021050916; WO2021050966; WO2021052970; WO2021067944; WO2021076642; WO2021076972; WO2021077063; WO2021081472; WO2021081511; WO2021087487; WO2021099466; WO2021101934; WO2021102050; WO2021113593; WO2021119047; WO2021119591; WO2021127100; WO2021133697; WO2021133977; WO2021138480; WO2021144824; WO2021146641; WO2021148985; WO2021150989; WO2021154401; WO2021155213; WO2021156876; WO2021161204;

each of which is expressly incorporated herein by reference.

Abeler, Johannes, Matthias Backer, Ulf Buermeyer, and Hannah Zillessen. "COVID-19 contact tracing and data protection can go together." JMIR mHealth and uHealth 8, no. 4 (2020): e19359.

Alam, Tanweer. "Internet of things and blockchain-based framework for Coronavirus (COVID-19) disease." Available at SSRN 3660503 (2020).

Alowais, Sarah. "Smartphone And Covid-19 Crisis: How The Smartphone Technology Impacted Life Under Covid-19 Pandemic." Issues in Information Systems 21, no. 4 (2020).

Arifeen, Md Murshedul, Abdullah Al Mamun, M. Shamim Kaiser, and Mufti Mahmud. "Blockchain-enable contact tracing for preserving user privacy during COVID-19 outbreak." (2020).

Aslam, Bakhtawar, Abdul Rehman Javed, Chinmay Chakraborty, Jamel Nebhen, Saira Raqib, and Muhammad Rizwan. "Blockchain and ANFIS empowered IoMT application for privacy preserved contact tracing in COVID-19 pandemic." Personal and Ubiquitous Computing (2021): 1-17.

Bachtiger, Patrik, Alexander Adamson, Jennifer K. Quint, and Nicholas S. Peters. "Belief of having had unconfirmed Covid-19 infection reduces willingness to participate in app-based contact tracing." NPJ digital medicine 3, no. 1 (2020): 1-7.

Buchanan, William J., Muhammad Ali Imran, Masood Ur-Rehman, Lei Zhang, Qammer H. Abbasi, Christos Chrysoulas, David Haynes, Nikolaos Pitropakis, and Pavlos Papadopoulos. "Review and critical analysis of privacy-preserving infection tracking and contact tracing." Frontiers in Communications and Networks 1 (2020): 2.

Cheng, Weibin, and Chun Hao. "Case-Initiated COVID-19 contact tracing using anonymous notifications." JMIR mHealth and uHealth 8, no. 6 (2020): e20369.

Cohen-McFarlane, Madison, Rafik Goubran, and Frank Knoefel. "Novel coronavirus cough database: NoCoCoDa." IEEE Access 8 (2020): 154087-154094.

Collado-Borrell, Roberto, Vicente Escudero-Vilaplana, Cristina Villanueva-Bueno, Ana Herranz-Alonso, and Maria Sanjurjo-Saez. "Features and functionalities of smartphone apps related to COVID-19: systematic search in app stores and content analysis." J Med Internet Res 22, no. 8 (2020): e20334.

Currie, Danielle J., Cindy Q. Peng, David M. Lyle, Brydie A. Jameson, and Michael S. Frommer. "Stemming the flow: how much can the Australian smartphone app help to control COVID-19." Public Health Res Pract 30, no. 2 (2020): 3022009.

Fenton, Norman, Scott McLachlan, Peter Lucas, Kudakwashe Dube, Graham Hitman, Magda Osman, Evangelia Kyrimi, and Martin Neil. "A privacy-preserving Bayesian network model for personalised COVID19 risk assessment and contact tracing." medRxiv (2021): 2020-07.

Idrees, Sheikh Mohammad, Mariusz Nowostawski, and Roshan Jameel. "Blockchain-based digital contact tracing apps for COVID-19 pandemic management: Issues, challenges, solutions, and future directions." JMIR medical informatics 9, no. 2 (2021): e25245.

Khan, Hameed, K. K. Kushwah, Saurabh Singh, Harshika Urkude, Muni Raj Maurya, and Kishor Kumar Sadasivuni. "Smart technologies driven approaches to tackle COVID-19 pandemic: a review." 3 Biotech 11, no. 2 (2021): 1-22.

Khan, Suleman, Muhammad Khurram Khan, and Rizwan Khan. "Harnessing intelligent technologies to curb COVID-19 pandemic: taxonomy and open challenges." Computing (2021): 1-20.

Kitchin, Rob. "Civil liberties or public health, or civil liberties and public health? Using surveillance technologies to tackle the spread of COVID-19." Space and Polity 24, no. 3 (2020): 362-381.

Kitchin, Rob. "Using digital technologies to tackle the spread of the coronavirus: Panacea or folly." The Programmable City Working Paper 44, no. April (2020): 1-24.

Liang, Steve H L, Sara Saeedi, Soroush Ojagh, Sepehr Honarparvar, Sina Kiaei, Mahnoush Mohammadi Jahromi, and Jeremy Squires. "An Interoperable Architecture for the Internet of COVID-19 Things (IoCT) Using Open Geospatial Standards-Case Study: Workplace Reopening." Sensors 21, no. 1 (2021): 50.

Maccari, Leonardo, and Valeria Cagno. "Do we need a contact tracing app?." Computer Communications 166 (2021): 9-18.

Maghdid, Halgurd S., and Kayhan Zrar Ghafoor. "A smartphone enabled approach to manage COVID-19 lockdown and economic crisis." SN Computer Science 1, no. 5 (2020): 1-9.

Manekiya, Mohammedhusen, and Massimo Donelli. "Monitoring the Covid-19 Diffusion by Combining Wearable Biosensors and Smartphones." Progress In Electromagnetics Research M 100 (2021): 13-21.

Narvaez, Alvaro Aspilcueta, and Jorge Guerra Guerra. "Received signal strength indication—based COVID-19 mobile application to comply with social distancing using bluetooth signals from smartphones." In Data Science for COVID-19, pp. 483-501. Academic Press, 2021.

Nasajpour, Mohammad, Seyedamin Pouriyeh, Reza M. Parizi, Mohsen Dorodchi, Maria Valero, and Hamid R. Arabnia. "Internet of Things for current COVID-19 and future pandemics: An exploratory study." Journal of healthcare informatics research (2020): 1-40.

Rowe, Frantz, Ojelanki Ngwenyama, and Jean-Loup Richet. "Contact-tracing apps and alienation in the age of COVID-19." European Journal of Information Systems 29, no. 5 (2020): 545-562.

Schuller, Björn Wolfgang, Dagmar M. Schuller, Kun Qian, Juan Liu, Huaiyuan Zheng, and Xiao Li. "COVID-19 and Computer Audition: An Overview on What Speech & SoundAnalysis Could Contribute in theSARS-CoV-2 Corona Crisis." Frontiers in Digital Health 3 (2021): 14.

Shin, Woochang. "Implementation of Cough Detection System Using IoT Sensor in Respirator." International journal of advanced smart convergence 9, no. 4 (2020): 132-138.

Shubina, Viktoriia, Sylvia Holcer, Michael Gould, and Elena Simona Lohan. "Survey of decentralized solutions with mobile devices for user location tracking, proximity detection, and contact tracing in the COVID-19 era." Data 5, no. 4 (2020): 87.

Singh, Hanson John Leon, Danielle Couch, and Kevin Yap. "Mobile health apps that help with COVID-19 management: scoping review." JMIR nursing 3, no. 1 (2020): e20596.

Trivedi, Amee, and Deepak Vasisht. "Digital contact tracing: technologies, shortcomings, and the path forward." ACM SIGCOMM Computer Communication Review 50, no. 4 (2020): 75-81.

Vedaei, Seyed Shahim, Amir Fotovvat, Mohammad Reza Mohebbian, Gazi M E Rahman, Khan A. Wahid, Paul Babyn, Hamid Reza Marateb, Marjan Mansourian, and Ramin Sami. "COVID-SAFE: an IoT-based system for automated health monitoring and surveillance in post-pandemic life." IEEE Access 8 (2020): 188538-188551.

Zhao, Zhiheng, Ray Y. Zhong, Yong-Hong Kuo, Yelin Fu, and George Q. Huang. "Cyber-physical spatial temporal analytics for digital twin-enabled smart contact tracing." Industrial Management & Data Systems (2021).

The foregoing references are expressly incorporated by reference in their entirety.

Automated classification of coughs as being from COVID-19 positive persons and COVID-19 negative persons has been proposed. See:

Andreu-Perez, Javier, Humberto Pérez-Espinosa, Eva Timonet, Mehrin Kiani, Manuel Ivan Giron-Perez, Alma B. Benitez-Trinidad, Delaram Jarchi et al. "A generic deep learning based cough analysis system from clinically validated samples for point-of-need covid-19 test and severity levels." IEEE Transactions on Services Computing (2021).

Bagad, Piyush, Aman Dalmia, Jigar Doshi, Arsha Nagrani, Parag Bhamare, Amrita Mahale, Saurabh Rane, Neeraj Agarwal, and Rahul Panicker. "Cough against COVID: Evidence of COVID-19 signature in cough sounds." arXiv preprint arXiv:2009.08790 (2020).

Banerjee, Annesya, and Achal Nilhani. "A Residual Network based Deep Learning Model for Detection of COVID-19 from Cough Sounds." arXiv preprint arXiv:2106.02348 (2021).

Bansal, Vipin, Gaurav Pahwa, and Nirmal Kannan. "Cough Classification for COVID-19 based on audio mfcc features using Convolutional Neural Networks." In 2020 IEEE International Conference on Computing, Power and Communication Technologies (GUCON), pp. 604-608. IEEE, 2020.

Belkacem, Abdelkader Nasreddine, Sofia Ouhbi, Abderrahmane Lakas, Elhadj Benkhelifa, and Chao Chen. "End-to-End AI-Based Point-of-Care Diagnosis System for Classifying Respiratory Illnesses and Early Detection of COVID-19: A Theoretical Framework." Frontiers in Medicine 8 (2021): 372.

Brown, Chloë, Jagmohan Chauhan, Andreas Grammenos, Jing Han, Apinan Hasthanasombat, Dimitris Spathis, Tong Xia, Pietro Cicuta, and Cecilia Mascolo. "Exploring automatic diagnosis of COVID-19 from crowdsourced respiratory sound data." arXiv preprint arXiv:2006.05919 (2020).

Buonsenso, Danilo, Niccolo Parri, Cristina De Rose, Piero Valentini, and Gemelli-pediatric COVID. "Toward a clinically based classification of disease severity for paediatric COVID-19." The Lancet. Infectious Diseases 21, no. 1 (2021): 22.

Chen, Dong, Feng Tang, Shushu Lu, and Qifa Song. "Toward a clinically based classification of disease severity for paediatric COVID-19-Authors' reply." The Lancet Infectious Diseases 21, no. 1 (2021): 22-23.

Chowdhury, Nihad Karim, Muhammad Ashad Kabir, and Md Rahman. "An Ensemble-based Multi-Criteria Decision Making Method for COVID-19 Cough Classification." arXiv preprint arXiv:2110.00508 (2021).

Dubnov, Tammuz. Signal Analysis and Classification of Audio Samples From Individuals Diagnosed With COVID-19. University of California, San Diego, 2020.

Erdogan, Yunus Emre, and Ali Narin. "COVID-19 detection with traditional and deep features on cough acoustic signals." Computers in Biology and Medicine 136 (2021): 104765.

Feng, Ke, Fengyu He, Jessica Steinmann, and Ilteris Demirkiran. "Deep-learning Based Approach to Identify Covid-19." In SoutheastCon 2021, pp. 1-4. IEEE, 2021.

Grant, Drew, Ian McLane, and James West. "Rapid and Scalable COVID-19 Screening using Speech, Breath, and Cough Recordings." In 2021 IEEE EMBS International Conference on Biomedical and Health Informatics (BHI), pp. 1-6. IEEE, 2021.

Imran, Ali, Iryna Posokhova, Haneya N. Qureshi, Usama Masood, Muhammad Sajid Riaz, Kamran Ali, Charles N. John, M D Iftikhar Hussain, and Muhammad Nabeel. "AI4COVID-19: AI enabled preliminary diagnosis for COVID-19 from cough samples via an app." Informatics in Medicine Unlocked 20 (2020): 100378.

Irawati, Mesayu Elida, and Hasballah Zakaria. "Classification Model for Covid-19 Detection Through Recording of Cough Using XGboost Classifier Algorithm." In 2021

International Symposium on Electronics and Smart Devices (ISESD), pp. 1-5. IEEE, 2021.

Kumar, Lella Kranthi, and P. J. A. Alphonse. "Automatic Diagnosis of COVID-19 Disease using Deep Convolutional Neural Network with Multi-Feature Channel from Respiratory Sound Data: Cough, Voice, and Breath." Alexandria Engineering Journal (2021).

Lella, Kranthi Kumar, and Alphonse Pja. "Automatic COVID-19 disease diagnosis using 1D convolutional neural network and augmentation with human respiratory sound based on parameters: cough, breath, and voice." AIMS Public Health 8, no. 2 (2021): 240.

Lu, Xiaofan, Yang Wang, Taige Chen, Jun Wang, and Fangrong Yan. "Classification of COVID-19 in intensive care patients." Critical Care 24, no. 1 (2020): 1-4.

Manshouri, Negin. "Identifying COVID-19 by Using Spectral analysis of Cough Recordings: A Distinctive Classification Study." (2021).

Melek, Mesut. "Diagnosis of COVID-19 and non-COVID-19 patients by classifying only a single cough sound." Neural Computing and Applications (2021): 1-12.

Mohammed, Emad A., Mohammad Keyhani, Amir Sanati-Nezhad, S. Hossein Hejazi, and Behrouz H. Far. "An ensemble learning approach to digital corona virus preliminary screening from cough sounds." Scientific Reports 11, no. 1 (2021): 1-11.

Mouawad, Pauline, Tammuz Dubnov, and Shlomo Dubnov. "Robust Detection of COVID-19 in Cough Sounds." SN Computer Science 2, no. 1 (2021): 1-13.

Orlandic, Lara, Tomas Teijeiro, and David Atienza. "The COUGHVID crowdsourcing dataset, a corpus for the study of large-scale cough analysis algorithms." Scientific Data 8, no. 1 (2021): 1-10.

Pahar, Madhurananda, and Thomas Niesler. "Machine Learning based COVID-19 Detection from Smartphone Recordings: Cough, Breath and Speech." arXiv preprint arXiv:2104.02477 (2021).

Pahar, Madhurananda, Marisa Klopper, Robin Warren, and Thomas Niesler. "COVID-19 Cough Classification using Machine Learning and Global Smartphone Recordings." Computers in Biology and Medicine (2021): 104572.

Pahar, Madhurananda, Marisa Klopper, Robin Warren, and Thomas Niesler. "COVID-19 Detection in Cough, Breath and Speech using Deep Transfer Learning and Bottleneck Features." arXiv preprint arXiv:2104.02477 (2021).

Pal, Ankit, and Malaikannan Sankarasubbu. "Pay attention to the cough: Early diagnosis of COVID-19 using interpretable symptoms embeddings with cough sound signal processing." In Proceedings of the 36th Annual ACM Symposium on Applied Computing, pp. 620-628. 2021.

Petrellis, Nikos, and George K. Adam. "Cough Sound Classification Based on Similarity Metrics." In 2021 44th International Conference on Telecommunications and Signal Processing (TSP), pp. 214-217. IEEE, 2021.

Ponomarchuk, Alexander, Ilya Burenko, Elian Malkin, Ivan Nazarov, Vladimir Kokh, Manvel Avetisian, and Leonid Zhukov. "Project Achoo: A Practical Model and Application for COVID-19 Detection from Recordings of Breath, Voice, and Cough." arXiv preprint arXiv:2107.10716 (2021).

Schuller, Björn W., Anton Batliner, Christian Bergler, Cecilia Mascolo, Jing Han, Iulia Lefter, Heysem Kaya et al. "The INTERSPEECH 2021 Computational Paralinguistics Challenge: COVID-19 cough, COVID-19 speech, escalation & primates." arXiv preprint arXiv:2102.13468 (2021).

Tena, Alberto, Francesc Claria, and Francesc Solsona. "Automated detection of COVID-19 cough." Biomedical Signal Processing and Control 71 (2022): 103175.

Valdés, Julio J., Pengcheng Xi, Madison Cohen-McFarlane, Bruce Wallace, Rafik Goubran, and Frank Knoefel. "Analysis of cough sound measurements including COVID-19 positive cases: A machine learning characterization." In 2021 IEEE International Symposium on Medical Measurements and Applications (MeMeA), pp. 1-6. IEEE, 2021.

Van Truong, Hoang, and Lam Pham. "A Cough-based deep learning framework for detecting COVID-19." arXiv preprint arXiv:2110.03251 (2021).

Vrindavanam, Jayavrinda, Raghunandan Srinath, Hari Haran Shankar, and Gaurav Nagesh. "Machine Learning based COVID-19 Cough Classification Models—A Comparative Analysis." In 2021 5th International Conference on Computing Methodologies and Communication (ICCMC), pp. 420-426. IEEE, 2021.

Wei, Wenqi, Jianzong Wang, Jiteng Ma, Ning Cheng, and Jing Xiao. "A real-time robot-based auxiliary system for risk evaluation of COVID-19 infection." arXiv preprint arXiv:2008.07695 (2020).

Xue, Hao, and Flora D. Salim. "Exploring Self-Supervised Representation Ensembles for COVID-19 Cough Classification." arXiv preprint arXiv:2105.07566 (2021).

The foregoing references are expressly incorporated by reference in their entirety.

Chronic respiratory conditions affect millions of people worldwide, with a high burden in terms of healthcare costs and absenteeism. The most prevalent are asthma, affecting predominantly children and young persons, and COPD, affecting especially adult and aged people. So international (WHO, PAHO) and local health care organizations aim to control them by increasing detection and awareness.

But other diseases are present, that cause disability and mortality, as bronchiectasis, cystic fibrosis, pulmonary fibrosis, etc. Although less prevalent, they consume a large budget for each affected person, at the same time they decrease autonomy and quality of life.

Although they are non-respiratory conditions, gastroesophageal reflux disease (GERD) and congestive heart failure (CHF) are also prevalent diseases that are very often part of diagnostic workup of respiratory diseases, since they share several features, specially chest tightness, wheezing, and cough.

These symptoms often indicate an exacerbation or aggravation of most of this conditions, and monitoring could help in the diagnostic process and guide treatment, once diagnosis has been reached.

For example, night coughing is one of the marker features of asthma, but is also present in GERD and CHF, which could be present in the same patient since they share at least one of the risk factors. So learning of night cough pattern or differentiating between characteristic cough sounds could be instrumental for the physician.

Most patients are not aware of their cough, because they are asleep, or because coughing is part of their everyday life. Furthermore, few patients can discriminate different cough patterns, apart from dry/wet. So, it would take a skilled person to follow and annotate every cough during a certain period, something that, for practical reasons, is impossible to achieve. For that reason, the complain about night symptoms usually comes from a relative sleeping near the patient, as are parents and spouses.

Of course, a physician can neither be present on the bedside every night, nor a single entire night. So, having the chance to record, discriminate and monitor the coughs could accelerate and simplify diagnostic process and avoid delays in the process or unnecessary empiric treatments.

Additionally, taking advantage from the same technology, other respiratory sounds not considered by the person could be recognized, recorded and counted, adding value to the process.

Finally, that information, totally confidential, could be made available to the physician in the way of a structured report, similar to the ones obtained from traditional diagnostic monitoring devices, as EKG or blood pressure Holter devices, respiratory polygraphs, etc.

Some conditions, as asthma or allergic rhinitis, are triggered by ambient conditions or pollutants. The most well known are pollen and pollution, for which there exist widespread located detectors, that send their information in real time to servers and make this information available for any user.

Coupling this data with respiratory sounds from a single person or from and entire population can help prevent community increase in pollutants associated symptoms, or at least contextualize them and avoid initiating unnecessary diagnostic processes.

But also on a population level, an increase in the occurrence of a symptom like cough, could be an early indicator of a respiratory infectious outbreak. And this could be detected many days or weeks in advance of the healthcare authorities taking knowledge.

Linking automated respiratory sound detection technology from a wide population to health care management services or organizations, could give trigger early warning as well as precise location and evolution of all those events. This can guide resource destination, containment policies, or enhance and simplify epidemiological monitoring.

The technology of automatic detection and analysis of respiratory sounds can be used in various situations. For example, to make a diagnosis of the disease, analyze the disease progression, study the symptoms of the disease, assess the risks of getting sick, etc. However, existing methods to detect and analyze coughs are not effective enough for automatic use in everyday life 24/7 for several reasons:

1. In everyday life, the sound of coughing contains extraneous sounds (the sound of the TV, the noise of passing cars, the conversation of other people, etc.). The extraneous sounds may interfere with automatic cough analysis. A segment in the sound may be selected that contains the sound of the cough, and only the sound segment with the cough used, so the problem of getting extraneous noise on the recording can be partially solved. However, the extraneous sounds may be present concurrently with the cough sounds. Therefore, a method is required that would automatically remove any extraneous sound, leaving only the coughing sound, in the selected segment. This class of tasks is usually called sound source separation, and is actively used in tasks to separate sound into components of vocals/drums/bass/piano/other separation. The inventors applied this approach to the task of clearing the sound of coughing from extraneous sounds and found its high efficiency. Likewise, the pattern of sounds when no cough sound is present may also be relevant to the analysis.

2. Identifying cough segments in the sound stream requires sound labeling, which may be a manual process. The beginning and the end of the segment in the sound that contains the cough sound needs to be isolated. Manual labeling is time-consuming and laborious. Likewise, a workable solution preferably can work with weakly labeled data.

3. If the detected cough sounds are to be analyzed by a qualified person (or other means which do not assure privacy), the user should be sure that no confidential information will get to the recording with the cough sound. To do this, the user will have to constantly listen to the recorded sounds and choose which sounds can be sent to the expert. This scenario is extremely inconvenient for the user and can hardly be called automatic.

4. A cough that does not belong to the user may get into the recording. For example, a person who is coughing next to the user. Thus, the user's cough analysis may include the cough of other people. To solve this problem requires a way to identify the user by the sounds of the cough, especially when a far field microphone is employed.

5. The method should be extremely effective for work on mobile devices and laptops and have a high quality of analysis.

The existing cough assessment methods do not split sound into cough sounds and other sounds, as in the Sound Source Separation task. Also, existing methods for determining the beginning and end of the sound of events such as coughing require manual labeling to train the model. U.S. Pub. Patent Application and Patent Nos. 20200098384; 20200029929; 20200015709; 20190336039; 20190095586; 20180228434; 20170368410; 20140336537; 20140067008; 20140052209; 20120302921; 20110087079; 20110015704; 20090216127; 20080312547; 20070118054; 20030083874; 20020059064; 20190029588; 20180126104; 20170325779; 20170007497; 20150245788; 20150025417; 20140336537; U.S. Pat. Nos. 10,750,976; 10,716,534; 10,709,414; 10,709,353; 10,702,239; 10,448,920; 10,269,228; 10,121,494; 9,042,992; 8,934,970; 8,777,874; 8,771,205; 8,588,906; 8,241,223; 8,177,720; 7,207,948; 7,107,209; 7,069,221; 7,048,697; 4,481,504; and 4,413,620.

Existing cough assessment methods don't use dry/wet assessment, and only count the number of explosive phases. See, e.g., Resapp, US20200015709A1. See also:

Adhi Pramono, R. X., S. Anas Imtiaz, and Esther Rodriguez-Villegas. "Automatic cough detection in acoustic signal using spectral features."

Ahmed, Mohsin Y., Md Mahbubur Rahman, and Jilong Kuang. "DeepLung: Smartphone Convolutional Neural Network-Based Inference of Lung Anomalies for Pulmonary Patients." In Interspeech, pp. 2335-2339. 2019.

Al Hossain, Forsad, Andrew A. Lover, George A. Corey, Nicholas G. Reich, and Tauhidur Rahman. "FluSense: a contactless syndromic surveillance platform for influenza-like illness in hospital waiting areas." Proceedings of the ACM on Interactive, Mobile, Wearable and Ubiquitous Technologies 4, no. 1 (2020): 1-28.

Amoh, Justice, and Kofi M. Odame. "An optimized recurrent unit for ultra-low-power keyword spotting." Proceedings of the ACM on Interactive, Mobile, Wearable and Ubiquitous Technologies 3, no. 2 (2019): 1-17.

Amoh, Justice, and Kofi Odame. "Deep neural networks for identifying cough sounds." IEEE transactions on biomedical circuits and systems 10, no. 5 (2016): 1003-1011.

Amoh, Justice, and Kofi Odame. "DeepCough: A deep convolutional neural network in a wearable cough detection system." In 2015 IEEE Biomedical Circuits and Systems Conference (BioCAS), pp. 1-4. IEEE, 2015.

Andreu-Perez, Javier, Humberto Pérez-Espinos, Eva Timone, Manuel I. Girón-Pérez, Mehrin Kiani, Alma B. Benitez-Trinidad, Delaram Jarchi et al. "A Novel Deep Learning Based Recognition Method and Web-App for Covid-19 Infection Test from Cough Sounds with a Clinically Validated Dataset." (2020).

Barata, Filipe, Kevin Kipfer, Maurice Weber, Peter Tinschert, Elgar Fleisch, and Tobias Kowatsch. "Towards device-agnostic mobile cough detection with convolutional neural networks." In 2019 IEEE International Conference on Healthcare Informatics (ICHI), pp. 1-11. IEEE, 2019.

Barata, Filipe, Peter Tinschert, Frank Rassouli, Claudia Steurer-Stey, Elgar Fleisch, Milo Alan Puhan, Martin Brutsche, David Kotz, and Tobias Kowatsch. "Automatic Recognition, Segmentation, and Sex Assignment of Nocturnal Asthmatic Coughs and Cough Epochs in Smartphone Audio Recordings: Observational Field Study." Journal of medical Internet research 22, no. 7 (2020): e18082.

Bardou, Dalal, Kun Zhang, and Sayed Mohammad Ahmad. "Lung sounds classification using convolutional neural networks." Artificial intelligence in medicine 88 (2018): 58-69.

Belkacem, Abdelkader Nasreddine, Sofia Ouhbi, Abderrahmane Lakas, Elhadj Benkhelifa, and Chao Chen. "End-to-End AI-Based Point-of-Care Diagnosis System for Classifying Respiratory Illnesses and Early Detection of COVID-19." arXiv preprint arXiv:2006.15469 (2020).

Botha, G. H. R., G. Theron, R. M. Warren, M. Klopper, K. Dheda, P. D. Van Helden, and T. R. Niesler. "Detection of tuberculosis by automatic cough sound analysis." Physiological measurement 39, no. 4 (2018): 045005.

Bouserhal, Rachel E., Philippe Chabot, Milton Sarria Paja, Patrick Cardinal, and Jérémie Voix. "Classification of Nonverbal Human Produced Audio Events: A Pilot Study." In interspeech, pp. 1512-1516. 2018.

Burileanu, Corneliu. "Cough Sound Recognition in Respiratory Disease Epidemics."

Chatrzarrin, Hanieh, Amaya Arcelus, Rafik Goubran, and Frank Knoefel. "Feature extraction for the differentiation of dry and wet cough sounds." In 2011 IEEE International Symposium on Medical Measurements and Applications, pp. 162-166. IEEE, 2011.

Di Perna, Leonardo, Gabriele Spina, Susannah Thackray-Nocera, Michael G. Crooks, Alyn H. Morice, Paolo Soda, and Albertus C. den Brinker. "An automated and unobtrusive system for cough detection." In 2017 IEEE Life Sciences Conference (LSC), pp. 190-193. IEEE, 2017.

Drugman, Thomas, Jerome Urbain, Nathalie Bauwens, Ricardo Chessini, Anne-Sophie Aubriot, Patrick Lebecque, and Thierry Dutoit. "Audio and contact microphones for cough detection." arXiv preprint arXiv:2005.05313 (2020).

Hiew, Y. H., J. A. Smith, D. J. Tait, B. M. G. Cheetham, J. E. Earis, and A. A. Woodcock. "Long-term objective cough recognition and quantification." (2002): 20-20.

Hoyos-Barcelo, Carlos, Jesus Monge-Alvarez, Muhammad Zeeshan Shakir, Jose-María Alcaraz-Calero, and Pablo Casaseca-de-La-Higuera. "Efficient k-NN implementation for real-time detection of cough events in smartphones." IEEE journal of biomedical and health informatics 22, no. 5 (2017): 1662-1671.

Hoyos-Barceló, Carlos, Jesús Monge-Álvarez, Zeeshan Pervez, Luis M. San-José-Revuelta, and Pablo Casaseca-de-la-Higuera. "Efficient computation of image moments for robust cough detection using smartphones." Computers in biology and medicine 100 (2018): 176-185.

Hoyos-Barceló, Carlos, José Ramón Garmendia-Leiza, María Dolores Aguilar-García, Jesús Monge-Álvarez, Diego Asay Párez-Alonso, Carlos Alberola-López, and Pablo Casaseca-de-la-Higuera. "Evaluation in a real environment of a trainable cough monitoring app for smartphones." In Mediterranean Conference on Medical and Biological Engineering and Computing, pp. 1175-1180. Springer, Cham, 2019.

Huynh, Thai Hoa, Vu An Tran, and Huy Dat Tran. "Semi-supervised tree support vector machine for online cough recognition." In Twelfth Annual Conference of the International Speech Communication Association. 2011.

Imran, Ali, Iryna Posokhova, Haneya N. Qureshi, Usama Masood, Sajid Riaz, Kamran Ali, Charles N. John, and Muhammad Nabeel. "AI4COVID-19: AI enabled preliminary diagnosis for COVID-19 from cough samples via an app." arXiv preprint arXiv:2004.01275 (2020).

Jayalakshmi, S. L., S. Chandrakala, and R. Nedunchelian. "Global statistical features-based approach for Acoustic Event Detection." Applied Acoustics 139 (2018): 113-118.

Kadambi, Prad, Abinash Mohanty, Hao Ren, Jaclyn Smith, Kevin McGuinnes, Kimberly Holt, Armin Furtwaengler et al. "Towards a wearable cough detector based on neural networks." In 2018 IEEE International Conference on Acoustics, Speech and Signal Processing (ICASSP), pp. 2161-2165. IEEE, 2018.

Khomsay, Sunisa, Rangsarit Vanijjirattikhan, and Jittiwut Suwatthikul. "Cough detection using PCA and deep learning." In 2019 International Conference on Information and Communication Technology Convergence (ICTC), pp. 101-106. IEEE, 2019.

Klco, Peter, Marian Kollarik, and Milos Tatar. "Novel computer algorithm for cough monitoring based on octonions." Respiratory physiology & neurobiology 257 (2018): 36-41.

Kochetov, Kirill, Evgeny Putin, Maksim Balashov, Andrey Filchenkov, and Anatoly Shalyto. "Noise masking recurrent neural network for respiratory sound classification." In International Conference on Artificial Neural Networks, pp. 208-217. Springer, Cham, 2018.

Kvapilova, Lucia, Vladimir Boza, Peter Dubec, Martin Majernik, Jan Bogar, Jamileh Jamison, Jennifer C. Goldsack, Duncan J. Kimmel, and Daniel R. Karlin. "Continuous sound collection using smartphones and machine learning to measure cough." Digital biomarkers 3, no. 3 (2019): 166-175.

Miranda, Igor D S, Andreas H. Diacon, and Thomas R. Niesler. "A comparative study of features for acoustic cough detection using deep architectures." In 2019 41st Annual International Conference of the IEEE Engineering in Medicine and Biology Society (EMBC), pp. 2601-2605. IEEE, 2019.

Monge-Alvarez, Jesus, Carlos Hoyos-Barceló, Keshav Dahal, and Pablo Casaseca-de-la-Higuera. "Audio-cough event detection based on moment theory." Applied Acoustics 135 (2018): 124-135.

Monge-Álvarez, Jesús, Carlos Hoyos-Barceló, Luis Miguel San-Josd-Revuelta, and Pablo Casaseca-de-la-Higuera. "A machine hearing system for robust cough detection based on a high-level representation of band-specific audio features." IEEE Transactions on Biomedical Engineering 66, no. 8 (2018): 2319-2330.

Monge-Álvarez, Jesús, Carlos Hoyos-Barceló, Paul Lesso, and Pablo Casaseca-de-la-Higuera. "Robust detection of audio-cough events using local Hu moments." IEEE journal of biomedical and health informatics 23, no. 1 (2018): 184-196.

Mun, Seongkyu, Suwon Shon, Wooil Kim, David K. Han, and Hanseok Ko. "Deep neural network based learning and transferring mid-level audio features for acoustic scene classification." In 2017 IEEE international conference on acoustics, speech and signal processing (ICASSP), pp. 796-800. IEEE, 2017.

Nemati, Ebrahim, Md Mahbubur Rahman, Viswam Nathan, and Jilong Kuang. "Private audio-based cough sensing for in-home pulmonary assessment using mobile devices." In EAI International Conference on Body Area Networks, pp. 221-232. Springer, Cham, 2018.

Nguyen, Khuong An, and Zhiyuan Luo. "Cover your cough: detection of respiratory events with confidence using a smartwatch." In Conformal and Probabilistic Prediction and Applications, pp. 114-131. 2018.

Pham, Cuong. "MobiCough: real-time cough detection and monitoring using low-cost mobile devices." In Asian Conference on Intelligent Information and Database Systems, pp. 300-309. Springer, Berlin, Heidelberg, 2016.

Pires, Ivan Miguel, Gongalo Marques, Nuno M. Garcia, Nuno Pombo, Francisco Flórez-Revuelta, Susanna Spinsante, Maria Canavarro Teixeira, and Eftim Zdravevski. "Recognition of Activities of Daily Living and Environments Using Acoustic Sensors Embedded on Mobile Devices." Electronics 8, no. 12 (2019): 1499.

Porter, Paul, Udantha Abeyratne, Vinayak Swarnkar, Jamie Tan, Ti-wan Ng, Joanna M. Brisbane, Deirdre Speldewinde et al. "A prospective multicentre study testing the diagnostic accuracy of an automated cough sound centred analytic system for the identification of common respiratory disorders in children." Respiratory research 20, no. 1 (2019): 81.

Pramono, Renard Xaviero Adhi, Syed Anas Imtiaz, and Esther Rodriguez-Villegas. "A cough-based algorithm for automatic diagnosis of pertussis." PloS one 11, no. 9 (2016): e0162128.

Pramono, Renard Xaviero Adhi, Syed Anas Imtiaz, and Esther Rodriguez-Villegas. "Automatic cough detection in acoustic signal using spectral features." In 2019 41st Annual International Conference of the IEEE Engineering in Medicine and Biology Society (EMBC), pp. 7153-7156. IEEE, 2019.

Rahman, Md Juber, Ebrahim Nemati, Mahbubur Rahman, Korosh Vatanparvar, Viswam Nathan, and Jilong Kuang. "Efficient Online Cough Detection with a Minimal Feature Set Using Smartphones for Automated Assessment of Pulmonary Patients."

Rudraraju, Gowrisree, ShubhaDeepti Palreddy, Baswaraj Mamidgi, Narayana Rao Sripada, Y. Padma Sai, Naveen Kumar Vodnala, and Sai Praveen Haranath. "Cough sound analysis and objective correlation with spirometry and clinical diagnosis." Informatics in Medicine Unlocked (2020): 100319.

Saba, Elliot. "Techniques for Cough Sound Analysis." PhD diss., 2018.

Sharan, Roneel V., Udantha R. Abeyratne, Vinayak R. Swarnkar, and Paul Porter. "Automatic croup diagnosis using cough sound recognition." IEEE Transactions on Biomedical Engineering 66, no. 2 (2018): 485-495.

Shi, Yan, He Liu, Yixuan Wang, Maolin Cai, and Weiqing Xu. "Theory and application of audio-based assessment of cough." Journal of Sensors 2018 (2018).

Shin, Sung-Hwan, Takeo Hashimoto, and Shigeko Hatano. "Automatic detection system for cough sounds as a symptom of abnormal health condition." IEEE Transactions on Information Technology in Biomedicine 13, no. 4 (2008): 486-493.

Swarnkar, Vinayak, Udantha R. Abeyratne, Yusuf Amrulloh, Craig Hukins, Rina Triasih, and Amalia Setyati. "Neural network based algorithm for automatic identification of cough sounds." In 2013 35th Annual International Conference of the IEEE Engineering in Medicine and Biology Society (EMBC), pp. 1764-1767. IEEE, 2013.

Teyhouee, Aydin, and Nathaniel D. Osgood. "Cough Detection Using Hidden Markov Models." In International Conference on Social Computing, Behavioral-Cultural Modeling and Prediction and Behavior Representation in Modeling and Simulation, pp. 266-276. Springer, Chain, 2019.

Tracey, Brian H., Germán Comina, Sandra Larson, Marjory Bravard, José W. López, and Robert H. Gilman. "Cough detection algorithm for monitoring patient recovery from pulmonary tuberculosis." In 2011 Annual international conference of the IEEE engineering in medicine and biology society, pp. 6017-6020. IEEE, 2011.

Vatanparvar, Korosh, Ebrahim Nemati, Viswam Nathan, Md Mahbubur Rahman, and Jilong Kuang. "CoughMatch-Subject Verification Using Cough for Personal Passive Health Monitoring." In 2020 42nd Annual International Conference of the IEEE Engineering in Medicine & Biology Society (EMBC), pp. 5689-5695. IEEE, 2020.

Vhaduri, Sudip. "Nocturnal cough and snore detection using smartphones in presence of multiple background-noises." In Proceedings of the 3rd ACM SIGCAS Conference on Computing and Sustainable Societies, pp. 174-186. 2020.

Vizel, Eldad, Mordechai Yigla, Yulia Goryachev, Eyal Dekel, Vered *Felis*, Hanna Levi, Isaac Kroin, Simon Godfrey, and Noam Gavriely. "Validation of an ambulatory cough detection and counting application using voluntary cough under different conditions." Cough 6, no. 1 (2010): 3.

Whitehill, Matt, Jake Garrison, and Shwetak Patel. "Whosecough: In-the-Wild Cougher Verification Using Multitask Learning." In ICASSP 2020-2020 IEEE International Conference on Acoustics, Speech and Signal Processing (ICASSP), pp. 896-900. IEEE, 2020.

You, Mingyu, Huihui Wang, Zeqin Liu, Chong Chen, Jiaming Liu, Xiang-Huai Xu, and Zhong-Min Qiu. "Novel feature extraction method for cough detection using NMF." IET Signal Processing 11, no. 5 (2017): 515-520.

You, Mingyu, Zeqin Liu, Chong Chen, Jiaming Liu, Xiang-Huai Xu, and Zhong-Min Qiu. "Cough detection by ensembling multiple frequency subband features." Biomedical Signal Processing and Control 33 (2017): 132-140.

Zhao, Jian, Xuan Li, Wanghong Liu, Yun Gao, Minggang Lei, Hequn Tan, and Di Yang. "DNN-HMM based acoustic model for continuous pig cough sound recognition." International Journal of Agricultural and Biological Engineering 13, no. 3 (2020): 186-193.

Laguarta, Jordi, Ferran Hueto, and Brian Subirana. "COVID-19 Artificial Intelligence Diagnosis using only Cough Recordings." IEEE Open Journal of Engineering in Medicine and Biology (2020).

SUMMARY OF THE INVENTION

The present invention provides a method, and automated systems embodying or performing the method, for automatically analyzing sounds from a microphone, to classify the sounds especially for cough, to identify whether the cough is from a target subject, and to ensure privacy of the recorded sounds.

The present invention also provides methods for detecting coughs and other types of pathology-related respiratory sounds (whooping cough, sneezing, barking cough, etc.), identifying the pathological respiratory sound, and evaluating parameters of the pathological respiratory sound through wearables devices, smart devices, laptops, and personal assistants in noisy environments. The method is suitable for continuous 24/7 surveillance in everyday life. The method may be achieved by using four models, which perform the following functions.

The present invention further comprises technology for monitoring the respiratory status of an individual over a long period of time, e.g., monitoring an asthmatic, chronic obstructive pulmonary disease patient, cardiac patient with e.g., congestive heart failure, smoker, etc., for the existence of symptoms, and to monitor and/or modify therapy. For example, monitoring cough sounds may help titrate doses of β-sympathomimetic drugs, steroids, antibiotics, diuretics, beta blockers, calcium channel blockers, antihypertensive drugs, antidiabetic drugs, etc. The monitoring may also help predict changes in status, by changes in frequency of cough or other respiratory sounds, or in features of such sounds.

For example, a respiratory model of a patient may be implemented, with appropriate latencies and correlations of triggers, respiratory sounds, activities, etc. As the respiratory sounds are monitored by the system according to the present technology, pathological features may be indicated, allowing both monitoring and prognostication. Where the condition is under therapy, the model may also help predict what modifications of a baseline regimen are appropriate to optimally maintain health. For example, the model may predict an optimal time for receiving a dose of inhaled albuterol to treat bronchial constriction, bearing in mind environmental triggers, past doses, patient history and drug sensitivity, diurnal variations, medical limits, and interaction with other medication. The model may also suggest non-medical intervention, such as walking, or avoidance of stress (to avoid triggering a stress-induced attack). The model may also be informed by weather report, pollen counts, etc., to compensate for allergens and other environmental triggers.

The technology is preferably implemented as a background task on a smartphone, and therefore must have very low power consumption. Likewise, in order to be generally compatible with a range of platforms, it should consume a small amount of random access memory, and not burden internal communication busses. External communications from the smartphone should be limited, and if possible piggyback on other communications. An intelligent selection should be made to determine which resources to employ at a given time to achieve the best strategy. For example, if WiFi is turned on, it is generally efficient to communicate using the WiFi rather than 4G/LTE or 5G. In order to effectively map contacts between people, Bluetooth is effective for determining proximity, and using the received signal strength indicator (RSSI), can provide an estimate of short-range proximity between smartphones. GPS may also be used to determine proximity, especially if the GPS systems of two receivers communicate to effect what is essentially a differential GPS system. Inertial management units (accelerometers, gyroscopes, magnetometers) within smartphones may also assist in effectively localizing smartphones to determine relative proximity. As a result, the system can detect respiratory sounds of smartphone users, persons nearby the smartphone distinct from the user, location and historical path of the smartphone, and proximity to other smartphones, to affect an automated contact tracing system, such as to track infections diseases including COVID-19 and influenza. See, e.g., U.S, 20200322767; 20200304941; 20200288673; 20200287948; 20200191511; 20200169848; 20200148320; 20200068852; 20200005628; 20190392701; 20190287382; 20190232860; 20190168635; 20190136580; 20190130137; 20190114901; 20190089393; 20190089392; 20190082756; 20190044559; 20180352135; 20180247151; 20180227732; 20180220264; 20180184777; 20180137523; 20180114435; 20180070193; 20180049028; 20180047014; 20170366529; 20170215034; 20170213445; 20170178512; 20170171750; 20170116546; 20170071018; 20160297316; 20160278156; 20160249212; 20160241999; 20160192145; 20160140846; 20160119149; 20160088438; 20160061481; 20160021535; 20150348003; 20150287109; 20150228066; 20150189467; 20150185837; 20150054797; 20140354441; 20140324527; 20140302795; 20140148207; 20140106677; 20140097608; 20140057646; 20140057609; 20130159705; 20120079080; 20100069115; 20080022089; U.S. Pat. Nos. 10,803,714; 10,796,559; 10,708,778; 10,652,734; 10,540,977; 10,507,760; 10,438,477; 10,412,070; 10,375,518; 10,346,468; 10,285,649; 10,215,443; 10,158,391; 10,111,031; 10,109,179; 10,089,862; 10,068,473; 9,973,913; 9,973,878; 9,949,079; 9,881,305; 9,815,382; 9,801,058; 9,787,951; 9,717,109; 9,682,638; 9,654,973; 9,603,179; 9,552,084; 9,531,548; 9,513,703; 9,313,614; 8,732,459; 8,433,244; 8,341,397; 8,069,319; and 7,831,786.

Alternately, assuming that all smartphones have a compatible app installed, local communication can occur through microphones and speakers, such as an ultrasonic signal emitted periodically through the speaker of one phone and heard through the microphone(s) of another phone.

More generally, the proximity detector can operate in different ways. For example, proximity detection may be based on analyzing signals formatted according to protocols, such as with near-field communication, radio-frequency identification, Bluetooth®. WiFi, especially in 5 GHz or higher bands, e.g., IEEE-802.11mc, see, people.csail.mit-.edu/bkph/ftmrtt_biblio:

Using Time of Flight (ToF) for Geolocation

"Facing the obstructed path problem in indoor TOA-based ranging between IEEE 802.11 nodes," M. Ciurana and F. Barcelo-Arroyo IEEE 19th International Symposium on Personal, Indoor and Mobile Radio Communications, 2008 October "WiFi FTM and Map Information Fusion for Accurate Positioning," Leor Banin, Uri Schatzberg, and Yuval Amizur, International Conference on Indoor Positioning and Indoor Navigation (IPIN), Alcale de Henares, Spain, 2016 Oct. 4-7.

"Wi-Fi Certified Location brings Wi-Fi indoor positioning capabilities," Wi-Fi Alliance, 2017 Feburary 22.

"High-Accuracy Indoor Geolocation using Collaborative Time of Arrival (CToA)," Leor Banin, Ofer Bar-Shalom, Nir Dvorecki, and Yuval Amizur, 2017 September.

"Reference Positioning Engine & Measurements Database for Indoor Time-Delay Wi-Fi Client Positioning," Leor Banin, Ofer Bar-Shalom, Nir Dvorecki, and Yuval Amizur, 2018 April.

"How to achieve 1-meter accuracy in Android," Frank Van Diggelen, Roy Want and Wei Wang, Google, 2018 Jul. 3

"Testing Wifi RTT on Android P for Indoor Positioning," James Cobb, CrowdConnected, 2018 Sep. 13.

"Scalable Wi-Fi Client Self-Positioning Using Cooperative FTM-Sensors," Leor Banin, Ofer Bar-Shalom, Nir Dvorecki, and Yuval Amizur, IEEE Transactions on Instrumentation and Measurement, 2018 October.

"Verification: Accuracy Evaluation of WiFi Fine Time Measurements on an Open Platform," Mohamed Ibrahim, Hansi Liu, Minitha Jawahar, Viet Nguyen, Marco Gruteser, Richard Howard, Bo Yu, and Fan Bai, MobiCom-18, 2018 Oct. 29-Nov. 2, New Delhi, India.

"A Machine Learning Approach for Wi-Fi RTT Ranging," Nir Dvorecki, Ofer Bar-Shalom, Leor Banin and Yuval Amizur, Proceedings of the 2019 International Technical Meeting of The Institute of Navigation, 2019 Jan. 28-31, Hyatt Regency, Reston, Reston Virginia "A Robust Dead Reckoning Algorithm Based on Wi-Fi FTM and Multiple Sensors," Yue Yu, Ruizhi Chen, Liang Chen, Guangyi Guo, Feng Ye and Zuoya Liu, Remote Sensing, Vol. 11, No. 5, 2019 March.

"Massive MIMO-based Localization and Mapping Exploiting Phase Information of Multipath Components," Xuhong Li, Magnus Oskarsson, Kalle Åström, and Fredrik Tofvesson, IEEE Trans. on Wireless Communications, 2019 June.

IEEE 802.11mc (a.k.a. IEEE 802.11-2016)

"Next Generation Positioning—Beyond Indoor Navigation," Jonathan Segev, Carlos Aldana, Naveen Kakani, Rolf de Vegt, Gal Basson, Ganesh Venkatesan, and Gaby Prechner, IEEE 11-14/1193r0, 2014

"Addition of p802.11-MC Fine Timing Measurement (FTM) to p802.1AS-Rev", Kevin Stanton and Carlos Aldana, 2015 Mar. 9.

"FTM Parameters for 802.1AS", Carlos Aldana, 2016 January

"Discussion of New State Machines and Specifications for Transport of Time Sync in 802.1AS using 802.11 FTM", Geoffrey M. Garner and Carlos Aldana, 2016 March.

"Security Enhancement to FTM," Qi Wang, Nehru Bhandaru and Matthew Fiischer 2016 July.

IEEE 802.11-2016—IEEE Standard for Information technology—Telecommunications and information exchange between systems Local and metropolitan area networks—Specific requirements—Part 11: Wireless LAN Medium Access Control (MAC) and Physical Layer (PHY) Specifications "IEEE 802.1AS REV D5.0 Review Comments", Ganesh Venkatesan, 2017 Sep. 10.

"Status of 802.1AS-Rev/D5.1 and Questions on Several Items Needing Resolution/Revision", Geoffrey Garner, 2017 Nov. 8.

"Derivation of FTM Parameters in 12.6 of 802.1AS-Rev", Geoffrey M. Garner 2018 Oct. 28.

Relative Permittivity of Building Materials

"Electromagnetic Signal Attenuation in Construction Material", William Stone et al (NIST), 1997 Oct.

"Propagation Losses Through Common Building Materials—2.4 GHz vs 5 GHz", Robert Wilson Magis Networks, 2002 August.

"Complex Permittivity of Planar Building Materials Measured with an Ultra-Wideband Free-Field Antenna Measurement System", Ben Davis, Chriss Grosvenor, Robert Johnk, David Novotny, James Baker-Jarvis, and Michael Janezic, Journal of Research of the National Institute of Standards and Technology, Volume 112, Number 1, 2007 January-February.

"Millimeter Waves Sensing behind Walls—Feasibility Study with FEL", B. Kapilevich, M. Einat, A. Yahalom, M. Kanter, B. Litvak, A. Gover, Proceedings of FEL 2007, 2007, Novosibirsk, Russia.

"Building Materials and Propagation Final Report—Ofcom", Richard Rudd, Ken Craid, Martin Ganley, and Richard Hartless, 2014 Sep. 14.

Super Resolution for Time of Arrival (ToA)

"Super-Resolution TOA Estimation with Diversity for Indoor Geolocation," Xinrong Li and Kaveh Pahlavan, IEEE Transactions on Wireless Communications, vol. 3, no. 1, pp. 224-234, 2004 January.

"Time of Arrival Estimation for WLAN Indoor Positioning Systems using Matrix Pencil Super Resolution Algorithms," Ali Aassie Ali and A. S. Omar, Proc. 2nd Workshop on Positioning, Navigation and Communications (WPNC), 2005

"Super-Resolution Time Delay Estimation in Multipath Environments," F. X. Ge, D. Shen, Y. Peng and V. O. K. Li, IEEE Transactions on Circuits and Systems I, vol. 54, no. 9, pp. 1977-1986, 2007 September.

"Super-Resolution Time of Arrival for Indoor Localization," David Humphrey, and Mark Hedley, Proc. IEEE Communications Society 2008 (ICC), 2008 May.

"Prior Models for Indoor Super-Resolution Time of Arrival Estimation," David Humphrey, and Mark Hedley, Proc. IEEE 69th Conference: Vehicular Technology Conference (VTC), 2009 May.

"High Resolution Time of Arrival Estimation for a Cooperative Sensor System," C. Morhart and E. M. Biebl, Advances in Radio Science, Vol. 8, pp. 61-66, 2010.

"Use of Super Resolution Algorithms for Indoor Positioning Keeping Novel Designed WLAN Signal Structure," Tariq J. S. Khanzada, Ali R. Ali, and Sameh A. Napoleon, ACM IWDE, 2010

"Super-Resolution Time of Arrival Estimationm Using Random Resampling in Compressed Sensing," Masanari Noto, Fang Shang, Shoukei Kidera, and Tetsuo Kirimiti, IEICE Trans. Commun., Vol E101-B, No. 6, 2018 June.

The foregoing references are expressly incorporated by reference in their entirety.

The proximity detector can obtain data about signals formatted according to such protocols using application programming interfaces for components running in the intelligent speaker device. As one example, the strength of a Bluetooth® signal between two devices can be used as an indicator of proximity between the devices. A lookup table may be used in a general case to estimate distance from RSSI value. In using data such as Bluetooth® signal strength to estimate device distance, operations may be performed on the data to improve performance. For example, a smoothing operation may be performed on the signal strength values, such as using a moving average of the signal strength values to estimate distance. A Kalman filter may also be employed based on trajectory presumptions. The resulting processed values can be monitored to provide an indication that smartphones are proximate, and the duration thereof. For example, a threshold value for received signal strength indication between two devices may be monitored to determine whether it rises above a threshold value, indicating proximity Additionally, such proximity values may be monitored for other indicators of a likelihood of disease transmission. For example, the proximity values prior to the threshold being reached may be monitored. For example, a speed of approach (indicated by a rate of change of the signal strength, or simply calculated from sequential positions) may be analyzed. Other features, such as the environment, room topology, time of day, and/or other features may also be used in conjunction with proximity to indicate an intent disease contagion potential.

While the presence of respiratory sounds is more generally used to indicate disease, a user or nearby person classification, the process may also be used to estimate the presence of contagion events, such as a cough or sneeze, or significant forced exhalation, such as loud talking, shouting, or singing, which exacerbate contagion, and therefore dramatically increase proximate risk.

The itinerary or path of a user may also be used to determine locations which may have been contaminated by a user, even retrospectively. Thus, it is not necessary for two people to be contemporaneously present in the same location in order for a contagion event to occur; rather, an infected person may leave infectious particles for minutes or hours after departing, and surfaces may remain infectious for significant periods. Therefore, by reporting likely contagious persons to a server, and then correlating contemporaneous or subsequent contacts by others with the contagious person or lingering contagious material, an automated contact tracing system may be affected. Where the smartphones are in proximity, a direct information transfer may occur.

In some cases, a person who is possibly contagious may be forced to be in public, such as when travelling for medical care. In such cases, the smartphone may serve as a warning beacon to alter others that they should remain distant and avoid contact.

In the more general case, the proximity system may also serve to remind people to remain socially distant, even where contagion risk is not apparent or elevated. That is, by sensing distances between smartphones, and through analysis of smartphone interaction and audio, the smartphone can determine when people are nearby and/or interacting, and estimate their distance. When the distance is less than 2 meters, an alert may be issued to one or both participants. Likewise, a separate cumulative risk may be assessed, e.g., more that 10 people in a closed room. Given the historical data, this may be extended to encompass warnings that a person is entering an environment that recently had a group of people (who may no longer be present), without proper time for natural decay in infectious particles, and/or lack of intervening sanitization.

The system may also provide reminders to users to sanitize hands, especially after entering elevated risk regions, such as public spaces with likely infectious surfaces. The smartphone may automatically detect sounds associated with sanitization process, to avoid unnecessary alerts or reminders, and therefore permit acceptability of aggressive reminders when actually due. Similarly, contact risk is lower when both parties to an encounter have recently sanitized their hands, and such information may be automatically passed between smartphones.

The present technology labels the commencement and termination of the events associated with pathological respiratory sounds automatically using weakly labeling data. Therefore, the method can be scaled to a larger data volume. The technology of identification by cough sound may be applied to exclude or differentiate the assessment of coughing by others. The technology therefore employs both environmental differences between the subject user and others within range of the microphone(s), and also biometric analysis to determine and identify the person who emitted the sound by non-speech sounds. In addition to assessing the characteristics of the phases of the cough, the method is preferably able to identify dry/wet coughs.

As noted above, the sound classification is not limited to cough, and may characterize and classify a variety of sounds, which even retrospectively may be determined as risk factors, or indicia of other events that may be distinct from a primary purpose of cough detection. For example, with continuously operative sound analysis, the system may also implement a natural language speech assistant technology, similar to Amazon Alexa, Microsoft Cortana, Google speech assistant, Samsung Bixby, etc. Therefore, while analyzing ambient sounds for respiratory keys, the system may also listen for "wake words", or even provide continuous interaction without preceding trigger wake words. See, US 20200251104; 20200227161; 20200227160; 20200077942; 20200020329; and 20200020328. The foregoing references are expressly incorporated by reference in their entirety.

The present technology addresses the following issues:

1. Separation of sound into the sound of coughing (or other sounds associated with respiratory pathology-associated events) and other sounds. Note that the technology may also be employed to analyze other biological sounds from the user, distinct from cough and pathological respiratory sounds.

2. Using a model architecture that is capable of determining the beginning and end of a coughing segment without manually marking the segments in sound. This allows rapid and low-cost scaling as the data volume grows.

3. Identification of coughing by sound, to exclude the analysis of coughing by surrounding people.

4. Characterization of coughing the characteristics, by both phase and type, e.g., a dry or wet cough.

The first model provides Sound Event Detection (SED), and recognizes the beginning and end of such events in sound as Cough, Sneeze, Clear throat (hereinafter CSC). The first model is the primary filter and allows the system to work only with segments in the sound that contain sounds CSC, the rest of the sound is not used, this improves the quality of recognition characteristics of CSC, and may also reduce power consumption, computational complexity, and limit processing overhead. The architecture of this model allows it to be taught using only the fact of coughing in the sound. The data for teaching this model (training data) may not have information about the beginning and end of the coughing epoch (FIG. 6), but the model can automatically detect the beginning and end of a segment.

The second model is Sound Source Separation (SSS), which separates CSC sound from background environment noise. The second model is designed to clear the CSC of extraneous sounds that occurred at the time of (concurrently with) the CSC. SSS removes any sounds other than CSC from the recording for better evaluation by both the specialist and machine learning methods. This model guarantees the user the removal of any confidential information that could have been recorded, even if this information was present at the time of coughing. And the quality of this model allows a qualified specialist to evaluate the sound of the cough.

The third model, Non Speech Sound Identification (NSSI), identifies the user by the cough, to exclude the evaluation of a cough that does not belong to the user. For example, if an adjacent person is coughing, this model can prevent this sample from being analyzed as the user's cough. Such a mechanism also allows contagion risk estimation by counting how often people are coughing around the user.

The fourth Cough Characteristics Description (CCD) model recognizes cough characteristics and parameters (dry, wet, heavy, duration, number of spasms, etc.). The CCD model is fed with the cough sound cleaned by the SSS model from extraneous noise. The model also estimates the length of coughing phases.

The methods described above can work both on the user's device to maintain confidentiality and on servers. The incoming sound source can be the sound of a mobile device or microphone of a stationary computer or any other microphone.

The models may be used together, or in some cases, with other processing techniques.

This technology was validated for ~200 participants. The participants installed a mobile application on their smartphone, that during the whole experiment listened to the incoming sound through the microphone of the smartphone. The SED model determined the presence of cough sounds in the incoming sound, with a probability value close to 0.5. The sound was sent for manual analysis. Approximately 2000 sounds were tested and the most complex sounds were selected as a test sample for analysis.

A computing system may include one or more input devices, one or more processors, one or more output devices, one or more storage devices, and one or more communication units. One or more of the devices, modules, storage areas, or other components of computing system may be interconnected to enable inter-component communications (physically, communicatively, and/or operatively). In some examples, such connectivity may be provided through communication channels, a system bus, a network connection, an inter-process communication data structure, or any other method for communicating data.

One or more processors of a computing system may implement functionality and/or execute instructions associated with computing system or associated with one or more modules. One or more processors may be, may be part of, and/or may include processing circuitry that performs operations in accordance with one or more aspects of the present disclosure. Examples of processors include microprocessors, application processors, display controllers, auxiliary processors, one or more sensor hubs, and any other hardware configured to function as a processor, a processing unit, or a processing device. The computing system may use one or more processors to perform operations in accordance with one or more aspects of the present disclosure using software, hardware, firmware, or a mixture of hardware, software, and firmware residing in and/or executing at computing system.

One or more communication units of the computing system may communicate with devices external to the computing system by transmitting and/or receiving data, and may operate, in some respects, as both an input device and an output device. In some examples, communication unit may communicate with other devices over a network. In other examples, communication units may send and/or receive radio signals on a radio network such as a cellular radio network. In other examples, communication units of computing system may receive satellite signals on a satellite network such as a Global Positioning System (GPS) network. Examples of communication units include a wireless network interface, an optical transceiver, a radio frequency transceiver, a GPS receiver, or any other type of device that can send and/or receive information. Other examples of communication units may include devices capable of communicating over Bluetooth®, GPS, NFC, RFID, WiFi, ZigBee, Zwave, UWB, and cellular networks (e.g., 3G, 4G/LTE, 5G), and Wi-Fi® radios found in mobile devices as well as Universal Serial Bus (USB) controllers and the like. Such communications may adhere to, implement, or abide by appropriate protocols, including Transmission Control Protocol/Internet Protocol (TCP/IP), Ethernet, Bluetooth, NFC, or other technologies or protocols.

One or more input devices, e.g., a microphone, may represent any input devices of computing system. One or more input devices may generate, receive, and/or process input from any type of device capable of detecting input from a human or machine. For example, one or more input devices may generate, receive, and/or process input in the form of electrical, physical, audio, image, and/or visual input (e.g., peripheral device, keyboard, microphone, camera).

One or more output devices may represent any output devices of computing system. One or more output devices may generate, receive, and/or process input from any type of device capable of detecting input from a human or machine. For example, one or more output devices may generate, receive, and/or process output in the form of electrical and/or physical output (e.g., speaker, display, haptic device, peripheral device, actuator).

One or more storage devices within the computing system may store information for processing during operation of the computing system. Storage devices may store program instructions and/or data associated with one or more of the modules described in accordance with one or more aspects of this disclosure. One or more processors and one or more storage devices may provide an operating environment or platform for such modules, which may be implemented as software, but may in some examples include any combination of hardware, firmware, and software. One or more processors may execute instructions and one or more storage devices may store instructions and/or data of one or more modules. For traditional processors, the instructions are non-transitory, and stably reside in a memory storage medium, though the memory storage medium itself may be non-volatile or volatile. In the case of quantum computing, the "instructions" themselves may represent quantum states of cubits, which are harder to fit into the traditional computational architecture paradigm. The combination of processors and storage devices may retrieve, store, and/or execute the instructions and/or data of one or more applications, modules, or software. Processors and/or storage devices may also be operably coupled to one or more other software and/or hardware components, including, but not limited to, one or more of the components of computing system and/or one or more devices or systems illustrated as being connected to the computing system.

In some examples, one or more storage devices are temporary memories, meaning that a primary purpose of the one or more storage devices is not long-term storage. Storage devices of the computing system may be configured for short-term storage of information as volatile memory and therefore not retain stored contents if deactivated. Examples of volatile memories include random access memories (RAM), dynamic random-access memories (DRAM), static random-access memories (SRAM), and other forms of volatile memories known in the art. Storage devices 320, in some examples, also include one or more computer-readable storage media. Storage devices may be configured to store larger amounts of information than volatile memory. Storage devices may further be configured for long-term storage of information as non-volatile memory space and retain information after activate/off cycles. Examples of non-volatile memories include magnetic hard disks, optical discs, Flash memories, or forms of electrically programmable memories (EPROM) or electrically erasable and programmable (EEPROM) memories.

A speech analysis module may analyze the audio input received from user device. For example, speech analysis mode may perform speech recognition on the audio input and transcribe the audio input into text. In some examples, machine learning engine applies a machine learning (ML) model (e.g., a Hidden Markov Model or neural networks) trained to recognize speech in the audio input. In some examples, speech analysis mode may transmit, via one or more communication units, the transcription of the audio input to one or more servers. The speech analysis module may comprise any commercial off-the-shelf or open-source speech analysis, audio processing, and/or language analysis software, such as Automatic Requirements Specification Extraction from Natural Language (ARSENAL), Very Agile Language Extraction Toolkit (VALET), and/or SenSay Analytics™ software. In some examples, speech analysis module applies audio processing software to audio input to produce text input. Speech analysis module may then apply ARSENAL or VALET to text generated from audio input to produce machine understandable specifications, formulas, models, or expressions. The speech analysis module may also apply SenSay Analytics™ software to perform speaker state classifications from the audio input, including emotion (e.g., emotional state), sentiment, cognition, health, mental health, health state, and communication quality.

A machine learning engine may include one or more neural networks, such as one or more of a Deep Neural Network (DNN) model, Recurrent Neural Network (RNN) model, and/or a Long Short-Term Memory (LSTM) model. In general, DNNs and RNNs learn from data available as feature vectors, and LSTMs learn from sequential data. The machine learning engine may apply other types of machine learning to train any of the ML models described herein. For example, machine learning engine may apply one or more of nearest neighbor, naive Bayes, decision trees, linear regression, support vector machines, neural networks, k-Means clustering, Q-learning, temporal difference, deep adversarial networks, or other supervised, unsupervised, semi-supervised, or reinforcement learning algorithms to train ML models.

Data clustering is a process of grouping together data points having common characteristics. In automated processes, a cost function or distance function is defined, and data is classified is belonging to various clusters by making decisions about its relationship to the various defined clusters (or automatically defined clusters) in accordance with the cost function or distance function. Therefore, the clustering problem is an automated decision-making problem. The science of clustering is well established, and various different paradigms are available. After the cost or distance function is defined and formulated as clustering criteria, the clustering process becomes one of optimization according to an optimization process, which itself may be imperfect or provide different optimized results in dependence on the particular optimization employed. For large data sets, a complete evaluation of a single optimum state may be infeasible, and therefore the optimization process subject to error, bias, ambiguity, or other known artifacts.

The ultimate goal of clustering is to provide users with meaningful insights from the original data, so that they can effectively solve the problems encountered. Clustering acts to effectively reduce the dimensionality of a data set by treating each cluster as a degree of freedom, with a distance from a centroid or other characteristic exemplar of the set. In a non-hybrid system, the distance is a scalar, while in systems that retain some flexibility at the cost of complexity, the distance itself may be a vector. Thus, a data set with 10,000 data points, potentially has 10,000 degrees of freedom, that is, each data point represents the centroid of its own cluster. However, if it is clustered into 100 groups of 100 data points, the degrees of freedom is reduced to 100, with the remaining differences expressed as a distance from the cluster definition. Cluster analysis groups data objects based on information in or about the data that describes the objects and their relationships. The goal is that the objects within a group be similar (or related) to one another and different from (or unrelated to) the objects in other groups. The greater the similarity (or homogeneity) within a group and the greater the difference between groups, the "better" or more distinct is the clustering.

In some cases, the dimensionality may be reduced to one, in which case all of the dimensional variety of the data set is reduced to a distance according to a distance function. This distance function may be useful, since it permits dimensionless comparison of the entire data set, and allows a user to modify the distance function to meet various constraints. Likewise, in certain types of clustering, the distance functions for each cluster may be defined independently, and then applied to the entire data set. In other types of clustering, the distance function is defined for the entire data set, and is not (or cannot readily be) tweaked for each cluster. Similarly, feasible clustering algorithms for large data sets preferably do not have interactive distance functions in which the distance function itself changes depending on the data. Many clustering processes are iterative, and as such produce a putative clustering of the data, and then seek to produce a better clustering, and when a better clustering is found, making that the putative clustering. However, in complex data sets, there are relationships between data points such that a cost or penalty (or reward) is incurred if data points are clustered in a certain way. Thus, while the clustering algorithm may split data points which have an affinity (or group together data points, which have a negative affinity, the optimization becomes more difficult.

In supervised classification, the mapping from a set of input data vectors to a finite set of discrete class labels is modeled in terms of some mathematical function including a vector of adjustable parameters. The values of these adjustable parameters are determined (optimized) by an inductive learning algorithm (also termed inducer), whose aim is to minimize an empirical risk function on a finite data set of input. When the inducer reaches convergence or terminates, an induced classifier is generated. In unsupervised classification, called clustering or exploratory data analysis, no labeled data are available. The goal of clustering is to separate a finite unlabeled data set into a finite and discrete set of "natural," hidden data structures, rather than provide an accurate characterization of unobserved samples generated from the same probability distribution. In semi-supervised classification, a portion of the data are labeled, or sparse label feedback is used during the process.

Non-predictive clustering is a subjective process in nature, seeking to ensure that the similarity between objects within a cluster is larger than the similarity between objects belonging to different clusters. Cluster analysis divides data into groups (clusters) that are meaningful, useful, or both. If meaningful groups are the goal, then the clusters should capture the "natural" structure of the data. In some cases, however, cluster analysis is only a useful starting point for other purposes, such as data summarization. However, this often begs the question, especially in marginal cases; what is the natural structure of the data, and how do we know when the clustering deviates from "truth" ?

Many data analysis techniques, such as regression or principal component analysis (PCA), have a time or space complexity of $O(m^2)$ or higher (where m is the number of objects), and thus, are not practical for large data sets. However, instead of applying the algorithm to the entire data set, it can be applied to a reduced data set consisting only of cluster prototypes. Depending on the type of analysis, the number of prototypes, and the accuracy with which the prototypes represent the data, the results can be comparable to those that would have been obtained if all the data could have been used. The entire data set may then be assigned to the clusters based on a distance function.

Clustering algorithms partition data into a certain number of clusters (groups, subsets, or categories). Important considerations include feature selection or extraction (choosing distinguishing or important features, and only such features); Clustering algorithm design or selection (accuracy and precision with respect to the intended use of the classification result; feasibility and computational cost; etc.); and to the extent different from the clustering criterion, optimization algorithm design or selection. Finding nearest neighbors can require computing the pairwise distance between all points. However, clusters and their cluster prototypes might be found more efficiently. Assuming that the clustering distance metric reasonably includes close points, and excludes far points, then the neighbor analysis may be limited to members of nearby clusters, thus reducing the complexity of the computation.

There are generally three types of clustering structures, known as partitional clustering, hierarchical clustering, and individual clusters. The most commonly discussed distinction among different types of clusterings is whether the set of clusters is nested or unnested, or in more traditional terminology, hierarchical or partitional. A partitional clustering is simply a division of the set of data objects into non-overlapping subsets (clusters) such that each data object is in exactly one subset. If the clusters have sub-clusters, then we obtain a hierarchical clustering, which is a set of nested clusters that are organized as a tree. Each node (cluster) in the tree (except for the leaf nodes) is the union of its children (sub-clusters), and the root of the tree is the cluster containing all the objects. Often, but not always, the leaves of the tree are singleton clusters of individual data objects. A hierarchical clustering can be viewed as a sequence of partitional clusterings and a partitional clustering can be obtained by taking any member of that sequence; i.e., by cutting the hierarchical tree at a particular level.

There are many situations in which a point could reasonably be placed in more than one cluster, and these situations are better addressed by non-exclusive clustering. In the most general sense, an overlapping or non-exclusive clustering is used to reflect the fact that an object can simultaneously belong to more than one group (class). A non-exclusive clustering is also often used when, for example, an object is "between" two or more clusters and could reasonably be assigned to any of these clusters. In a fuzzy clustering, every object belongs to every cluster with a membership weight. In other words, clusters are treated as fuzzy sets. Similarly, probabilistic clustering techniques compute the probability with which each point belongs to each cluster. In many cases, a fuzzy or probabilistic clustering is converted to an exclusive clustering by assigning each object to the cluster in which its membership weight or probability is highest. Thus, the inter-cluster and intra-cluster distance function is symmetric. However, it is also possible to apply a different function to uniquely assign objects to a particular cluster.

A well-separated cluster is a set of objects in which each object is closer (or more similar) to every other object in the cluster than to any object not in the cluster. Sometimes a threshold is used to specify that all the objects in a cluster must be sufficiently close (or similar) to one another. The distance between any two points in different groups is larger than the distance between any two points within a group. Well-separated clusters do not need to be spherical, but can have any shape.

If the data is represented as a graph, where the nodes are objects and the links represent connections among objects, then a cluster can be defined as a connected component; i.e., a group of objects that are significantly connected to one another, but that have less connected to objects outside the group. This implies that each object in a contiguity-based cluster is closer to some other object in the cluster than to any point in a different cluster.

A density-based cluster is a dense region of objects that is surrounded by a region of low density. A density-based definition of a cluster is often employed when the clusters are irregular or intertwined, and when noise and outliers are present. DBSCAN is a density-based clustering algorithm that produces a partitional clustering, in which the number of clusters is automatically determined by the algorithm. Points in low-density regions are classified as noise and omitted; thus, DBSCAN does not produce a complete clustering.

A prototype-based cluster is a set of objects in which each object is closer (more similar) to the prototype that defines the cluster than to the prototype of any other cluster. For data with continuous attributes, the prototype of a cluster is often a centroid, i.e., the average (mean) of all the points in the cluster. When a centroid is not meaningful, such as when the data has categorical attributes, the prototype is often a medoid, i.e., the most representative point of a cluster. For many types of data, the prototype can be regarded as the most central point. These clusters tend to be globular. K-means is a prototype-based, partitional clustering technique that attempts to find a user-specified number of clusters (K), which are represented by their centroids. Prototype-based clustering techniques create a one-level partitioning of the data objects. There are a number of such techniques, but two of the most prominent are K-means and K-medoid. K-means defines a prototype in terms of a centroid, which is usually the mean of a group of points, and is typically applied to objects in a continuous n-dimensional space. K-medoid defines a prototype in terms of a medoid, which is the most representative point for a group of points, and can be applied to a wide range of data since it requires only a proximity measure for a pair of objects. While a centroid almost never corresponds to an actual data point, a medoid, by its definition, must be an actual data point.

In the K-means clustering technique, we first choose K initial centroids, the number of clusters desired. Each point in the data set is then assigned to the closest centroid, and each collection of points assigned to a centroid is a cluster. The centroid of each cluster is then updated based on the points assigned to the cluster. We iteratively assign points and update until convergence (no point changes clusters), or equivalently, until the centroids remain the same. For some combinations of proximity functions and types of centroids, K-means always converges to a solution; i.e., K-means reaches a state in which no points are shifting from one cluster to another, and hence, the centroids don't change. Because convergence tends to b asymptotic, the end condition may be set as a maximum change between iterations. Because of the possibility that the optimization results in a local minimum instead of a global minimum, errors may be maintained unless and until corrected. Therefore, a human assignment or reassignment of data points into classes, either as a constraint on the optimization, or as an initial condition, is possible.

To assign a point to the closest centroid, a proximity measure is required. Euclidean (L2) distance is often used for data points in Euclidean space, while cosine similarity may be more appropriate for documents. However, there may be several types of proximity measures that are appropriate for a given type of data. For example, Manhattan (L1) distance can be used for Euclidean data, while the Jaccard measure is often employed for documents. Usually, the similarity measures used for K-means are relatively simple since the algorithm repeatedly calculates the similarity of each point to each centroid, and thus complex distance functions incur computational complexity. The clustering may be computed as a statistical function, e.g., mean square error of the distance of each data point according to the distance function from the centroid. Note that the K-means may only find a local minimum, since the algorithm does not test each point for each possible centroid, and the starting presumptions may influence the outcome. The typical distance functions for documents include the Manhattan (L1) distance, Bregman divergence, Mahalanobis distance, squared Euclidean distance and cosine similarity.

An optimal clustering will be obtained as long as two initial centroids fall anywhere in a pair of clusters, since the centroids will redistribute themselves, one to each cluster. As the number of clusters increases, it is increasingly likely that at least one pair of clusters will have only one initial centroid, and because the pairs of clusters are further apart than clusters within a pair, the K-means algorithm will not redistribute the centroids between pairs of clusters, leading to a suboptimal local minimum. One effective approach is to take a sample of points and cluster them using a hierarchical clustering technique. K clusters are extracted from the hierarchical clustering, and the centroids of those clusters are used as the initial centroids. This approach often works well, but is practical only if the sample is relatively small, e.g., a few hundred to a few thousand (hierarchical clustering is expensive), and K is relatively small compared to the sample size. Other selection schemes are also available.

The space requirements for K-means are modest because only the data points and centroids are stored. Specifically, the storage required is $O((m+K)n)$, where m is the number of points and n is the number of attributes. The time requirements for K-means are also modest—basically linear in the number of data points. In particular, the time required is $O(I \times K \times m \times n)$, where I is the number of iterations required for convergence. As mentioned, I is often small and can usually be safely bounded, as most changes typically occur in the first few iterations. Therefore, K-means is linear in m, the number of points, and is efficient as well as simple provided that K, the number of clusters, is significantly less than m.

Outliers can unduly influence the clusters, especially when a squared error criterion is used. However, in some clustering applications, the outliers should not be eliminated or discounted, as their appropriate inclusion may lead to important insights. In some cases, such as financial analysis, apparent outliers, e.g., unusually profitable investments, can be the most interesting points.

Hierarchical clustering techniques are a second important category of clustering methods. There are two basic approaches for generating a hierarchical clustering: Agglomerative and divisive. Agglomerative clustering merges close clusters in an initially high dimensionality space, while divisive splits large clusters. Agglomerative clustering relies upon a cluster distance, as opposed to an object distance. For example, the distance between centroids or medioids of the clusters, the closest points in two clusters, the further points in two clusters, or some average distance metric. Ward's method measures the proximity between two clusters in terms of the increase in the sum of the squares of the errors that results from merging the two clusters.

Agglomerative Hierarchical Clustering refers to clustering techniques that produce a hierarchical clustering by starting with each point as a singleton cluster and then repeatedly merging the two closest clusters until a single, all-encompassing cluster remains. Agglomerative hierarchical clustering cannot be viewed as globally optimizing an objective function. Instead, agglomerative hierarchical clustering techniques use various criteria to decide locally, at each step, which clusters should be merged (or split for divisive approaches). This approach yields clustering algorithms that avoid the difficulty of attempting to solve a hard combinatorial optimization problem. Furthermore, such approaches do not have problems with local minima or difficulties in choosing initial points. Of course, the time complexity of $O(m^2 \log m)$ and the space complexity of O(m2) are prohibitive in many cases. Agglomerative hierarchical clustering algorithms tend to make good local decisions about combining two clusters since they can use information about the pair-wise similarity of all points. However, once a decision is made to merge two clusters, it cannot be undone at a later time. This approach prevents a local optimization criterion from becoming a global optimization criterion.

In supervised classification, the evaluation of the resulting classification model is an integral part of the process of developing a classification model. Being able to distinguish whether there is non-random structure in the data is an important aspect of cluster validation.

Abraham, Ittai, et al. "Low-distortion inference of latent similarities from a multiplex social network." SIAM Journal on Computing 44.3 (2015): 617-668.

Aldenderfer, M. S., and R. K. Blashfield. Cluster Analysis. Sage Publications, Los Angeles, 1985.

Anderberg, M. R. (1973). Cluster Analysis for Applications. Academic Press, New York.

Anderson, E. (1957). A semi-graphical method for the analysis of complex problems. Proc. Nat. Acad. Sci. USA 43923-927.

Anderson, T. W. (1958). An Introduction to Multivariate Statistical Analysis. Wiley, New York.

Anderson, T. W., and Bahadur, R. R. (1962). classification into two multivariate normal distributions with different covariance matrices. Ann. Math. Statist. 33420-431.

Andrews, D. F. (1972). Plots of high-dimensional data. Biometrics 28 125-136.

Ankerst, M., M. M. Breunig, H.-P. Kriegel, and J. Sander. OPTICS: Ordering Points To Identify the Clustering Structure. In Proc. of 1999 ACM-SIGMOD Intl. Conf. on Management of Data, pages 49-60, Philadelphia, Pennsylvania, June 1999. ACM Press.

Arabie, P. (1977). clustering representations of group overlap. J. Math. Soc. 5 112-128.

Arabie, P. and Carroll, J. D. (1980). MAPCLUS: A mathematical programming approach to fitting to ADCLUS model. Psychometrika 45211-235.

Arabie, P., L. Hubert, and G. D. Soete. An overview of combinatorial data analysis. In P. Arabie, L. Hubert, and G. D. Soete, editors, Clustering and Classification, pages 188-217. World Scientific, Singapore, January 1996.

Art, D., Gnanadesikan, R., and Kettenring, J. R. (1982). Data-based metrics for cluster analysis. Utilitas Mathematica 31A 75-99.

Asimov, D. (1985). The grand tour. SLAM J. Sci. Statist. Corn-put. 6 128-143.

Auffarth, Benjamin, Yasumasa Muto, and Yasuharu Kunii. "An artificial system for visual perception in autonomous Robots." Proceedings of the IEEE International Conference on Intelligent Engineering Systems. 2005.

Babu, B. Hari, N. Subash Chandra, and T. Venu Gopal. "Clustering Algorithms For High Dimensional Data—A Survey Of Issues And Existing Approaches."

Baker, F. B. (1974). Stability of two hierarchical grouping techniques, Case I: Sensitivity to data errors. J. Amer. Statist. Assoc. 69440-445.

Ball, G., and D. Hall. A Clustering Technique for Summarizing Multivariate Data. Behavior Science, 12:153-155, March 1967.

Banerjee, A., S. Merugu, I. S. Dhillon, and J. Ghosh. Clustering with Bregman Divergences. In Proc. of the 2004 SIAM Intl. Conf. on Data Mining, pages 234-245, Lake Buena Vista, FL, April 2004.

Baraglia, R., Dazzi, P., Mordacchini, M., & Ricci, L. (2013). A peer-to-peer recommender system for self-emerging user communities based on gossip overlays. Journal of Computer and System Sciences, 79(2), 291-308.

Baragliaa, R., Dazzia, P., Mordacchinib, M., & Riccic, L. A Peer-to-Peer Recommender System for self-emerging user communities based on Gossip Overlays. (2012)

Beck, Carolyn, et al. "Dynamic Coverage and Clustering: A Maximum Entropy Approach." Distributed Decision Making and Control. Springer London, 2012. 215-243.

Becker, P. (1968). Recognitions of Patterns. Polyteknisk, Copenhagen.

Bell, P. A. and Korey, J. L. (1975). QUICLSTR: A FOR'TRAN program for hierarchical cluster analysis with a large number of subjects. Behavioral Research Methods and Instrumentation 7575.

Berg, Mikko. "Human abilities to perceive, understand, and manage multi-dimensional information with visualizations." (2012).

Berkhin, P. Survey Of Clustering Data Mining Techniques. Technical report, Accrue Software, San Jose, CA, 2002.

Bhat, Sajid Yousuf, and Muhammad Abulaish. "A density-based approach for mining overlapping communities from social network interactions." Proceedings of the 2nd International Conference on Web Intelligence, Mining and Semantics. ACM, 2012.

Binder, D. A. (1978). Comment on 'Estimating mixtures of normal distributions and switching regressions'. j Amer. Statist. Assoc. 73746-747.

Blashfield, R. K., Aldenderfer, M. S. and Morey, L. C. (1982). cluster analysis literature on validation. In Classifying Social Data. (H. Hudson, ed.) 167-176. Jossey-Bass, San Francisco.

Bock, H. H. (1985). On significance tests in cluster analysis. J. Classification 277-108.

Boley, D. Principal Direction Divisive Partitioning. Data Mining and Knowledge Discovery, 2(4):325-344, 1998.

Boley, Daniel, and Vivian Borst. "A General Unsupervised Clustering Tool for Unstructured Data." matrix 100: 2.

Boratto, Ludovico. "Group recommendation with automatic detection and classification of groups." (2012).

Bradley, P. S. and U. M. Fayyad. Refining Initial Points for K-Means Clustering. In Proc. of the 15th Intl. Conf. on Machine Learning, pages 91-99, Madison, WI, July 1998. Morgan Kaufmann Publishers Inc.

Breiman, L. Meisel, W. S., and Purcell, E. (1977). Variable kernel estimates of multivariate densities and their calibration. Technometrics 19 135-144.

Brieman, L., Friedman, J. H., Olshen, R. A., and Stone, C. J. (1984). Classification and Regression Trees. Wadsworth, Belmont, CA Broadbent, S. R. and Hammersley, J. M. (1957). Percolation Processes, I: Crystals and Mazes. Proc. Cambridge Philos. Soc. 53629-641

Bu, Yingyi, et al. "The HaLoop approach to large-scale iterative data analysis." The VLDB Journal—The International Journal on Very Large Data Bases 21.2 (2012): 169-190.

Buja, A., Hurify, C. and Mcdonald, J. A. (1986). A data viewer for multivariate data. Computer Science and Statistics: Proceedings of the 18th Symposium on the Interface 171-174.

Cacoullos, T. (1966). Estimation of a multivariate density. Ann. Math. Statist. 18 179-189.

Cai, Rui, et al. "Scalable music recommendation by search." Proceedings of the 15th international conference on Multimedia. ACM, 2007.

Carrizosa, Emilio, and Dolores Romero Morales. "Supervised classification and mathematical optimization." Computers & Operations Research 40.1 (2013): 150-165.

Chang, Chin-Chun, and Hsin-Yi Chen. "Semi-supervised clustering with discriminative random fields." Pattern Recognition 45.12 (2012): 4402-4413.

Chen, H., Gnanadesikan, R., and Kettenring, J. R. (1974). Statistical methods for grouping corporations. Sankhya B 36 1-28.

Chen, Yen Hung. "The k Partition-Distance Problem." Journal of Computational Biology 19.4 (2012): 404-417.

Cheng, Hong, et al. "Clustering large attributed information networks: an efficient incremental computing approach." Data Mining and Knowledge Discovery 25.3 (2012): 450-477.

Chernoff, H. (1972). The selection of effective attributes for deciding between hypotheses using linear discriminant functions. In Frontiers of Pattern Recognition. (S. Watanabe, ed.) 55-60. Academic Press, New York.

Chernoff, H. (1973a). Some measures for discriminating between normal multivariate distributions with unequal covariance matrices. In Multivariate Analysis Ill. (P. R. Krishnaiah, ed.) 337-344. Academic Press, New York.

Chernoff, H. (1973b). The use of faces to represent points in k-dimensional space graphically. J Amer. Statist. Assoc. 68 361-368.

Cherubini, Umberto, and Agnese Sironi. Bond Trading, Market Anomalies and Neural Networks: An Application with Kohonen Nets. No. 012. Society for Computational Economics.

Christou, Ioannis T., George Gekas, and Anna Kyrikou. "A classifier ensemble approach to the TV-viewer profile adaptation problem." International Journal of Machine Learning and Cybernetics 3.4 (2012): 313-326.

Clunies-Ross, C. W. and Riffenburgh, R. H. (1960). Geometry and linear discrimination. Biometrika 47185-189.

Cormack, R. M. (1971). A review of classification (with discussion). J Roy. Statist. Soc. A 134321-367.

Cornfield, J. (1962). Joint dependence of rish of coronary heart disease on serum cholesterol and systolic blood pressure: a discriminant function analysis. Federal Proceedings 21 58-61.

Cover, T. M. (1968). Estimation by the nearest neighbor rule. IEEE Transactions Information Theory IT-14 50-55.

Cover, T. M. and Hart, P. E. (1967). Nearest neighbor pattern classification. IEEE Transactions, Information Theory IT-13 21-27.

Dallal, G. E. (1975) A user's guide to J. A. Hartigan's clustering algorithms. (unpublished manuscript) Yale University.

Day, N. E. (1969). Estimating the components of a mixture of normal distributions. Biometrika 56463-474.

Day, N. E., and Kerridge, D. F., (1967). A general maximum likelihood discriminant. Biometrics 23313-323. 94 de Máster, Trabajo Fin. "Novelty and Diversity Enhancement and Evaluation in Recommender Systems." (2012).

Defays, D. (1977). An efficient algorithm for a complete link method. Computer Journal 20364-366.

Derrac, Joaquín, Isaac Triguero, Salvador García, and Francisco Herrera. "Integrating instance selection, instance weighting, and feature weighting for nearest neighbor classifiers by coevolutionary algorithms." Systems, Man, and Cybernetics, Part B: Cybernetics, IEEE Transactions on 42, no. 5 (2012): 1383-1397.

Devi, B. Naveena, et al. "Design and implementation of web usage mining intelligent system in the field of e-commerce." Procedia Engineering 30 (2012): 20-27.

Dhillon, I. S., and D. S. Modha. Concept Decompositions for Large Sparse Text Data Using Clustering. Machine Learning, 42(1/2):143-175, 2001.

Dhillon, I. S., Y. Guan, and J. Kogan. Iterative Clustering of High Dimensional Text Data Augmented by Local Search. In Proc. of the 2002 IEEE Intl. Conf. on Data Mining, pages 131-138. IEEE Computer Society, 2002.

Dick, N. P. and Bowden, D. C. (1973). Maximum likelihood estimation for mixtures of two normal distributions. Biometrics 29781-790

Dixon, W. J. (ed.) (1981). BMDP Statistical Software. University of California Press, Berkeley.

Donoho, A. W., Donoho, D. L. and Gasko, M. (1985). MacS-pin graphical data analysis software. D2 Software, Austin.

Dragut, Andreea B. "Stock Data Clustering and Multiscale Trend Detection." Methodology and Computing in Applied Probability 14.1 (2012): 87-105.

Dragut, Eduard C., Weiyi Meng, and Clement T. Yu. "Deep Web Query Interface Understanding and Integration." Synthesis Lectures on Data Management 7.1 (2012): 1-168.

Drosou, Marina, and Evaggelia Pitoura. "Dynamic diversification of continuous data." Proceedings of the 15th International Conference on Extending Database Technology. ACM, 2012.

Duda, R. O. and Hart, P. E. (1973). Pattern Classification and Scene Analysis. Wiley, New York.

Duda, R. O., P. E. Hart, and D. G. Stork. Pattern Classification. John Wiley & Sons, Inc., New York, second edition, 2001.

Edmonston, B. (1985). MICRO-CLUSTER: Cluster analysis software for microcomputers. Journal of Classification 2 127-130.

Efron, B. (1975). The efficiency of logistic regression compared to normal discriminant analysis. j Amer. Statist. Assoc. 70 892-898.

Efron, B. (1979). Bootstrap methods: Another look at the jack-knife. Ann. Statist. 7 1-26.

Efron, B. (1982). The Jackknife, The Bootstrap, and Other Resampling Plans, SIAM NSF-CBMS, Monograph #38.

Efron, B. (1983). Estimating the error rate of a prediction rule: Improvements on cross-validation. J. Amer. Statist. Assoc. 78 316-331.

Ehmke, Jan Fabian. "Knowledge Discovery and Data Mining." Integration of Information and Optimization Models for Routing in City Logistics. Springer US, 2012. 37-57.

Ester, M., H.-P. Kriegel, J. Sander, and X. Xu. A Density-Based Algorithm for Discovering Clusters in Large Spatial Databases with Noise. In Proc. of the 2nd Intl. Conf. on Knowledge Discovery and Data Mining, pages 226-231, Portland, Oregon, August 1996. AAAI Press.

Ester, M., H.-P. Kriegel, J. Sander, M. Wimmer, and X. Xu. Incremental Clustering for Mining in a Data Warehousing Environment. In Proc. of the 24th VLDB Conf., pages 323-333, New York City, August 1998. Morgan Kaufmann.

Everitt, B. (1980). Cluster Analysis. 2nd ed. Halsted, New York

Everitt, B. S. and Hand, D. J. (1981). Finite Mixture Distributions. Chapman and Hall, London.

Everitt, B. S., S. Landau, and M. Leese. Cluster Analysis. Arnold Publishers, London, fourth edition, May 2001.

Farver, T. B. and Dunn, O. J. (1979). Stepwise variable selection in classification problems. Biom. J. 21 145-153.

Fisher, D. Iterative Optimization and Simplification of Hierarchical Clusterings. Journal of Artificial Intelligence Research, 4:147-179, 1996.

Fisher, R. A. (1936). The use of multiple measurements in taxonomic problems. Ann. Eugenics 7 (part 2) 179-188.

Fisherkeller, M. A., Friedman, J. H., and Tukey, J. W. (1974). Prim-9: An interactive multidimensional data display and analysis system. SLAC-Pub. 1408, Stanford Linear Accelerator Center, Stanford, California.

Fitch, W. M. and Marcouash, E. (1967). Construction of phylogenetic trees. Science 155279-284.

Fix, E. and Hodges, J. (1951). Discriminatory analysis, non-parametric discrimination: consistency properties. Technical Report. Randolph Field, Texas: USAF School of Aviation Medicine.

Fouad, Khaled M., et al. "Web-based Semantic and Personalized Information Retrieval Semantic and Personalized Information Retrieval Semantic and Personalized Information Retrieval." (2012).

Fournier, Chris, and Diana Inkpen. "Segmentation similarity and agreement." Proceedings of the 2012 Conference of the North American Chapter of the Association for Computational Linguistics: Human Language Technologies. Association for Computational Linguistics, 2012.

Fowixes, E. B. (1987). Some diagnostics for binary logistic regression via smoothing. Biometrika to appear.

Fowlkes, E. B. and Mallows, C. L. (1983). A method for comparing two hierarchical clusterings (with discussion). J Amer. Statist. Assoc. 78553-583.

Fowlkes, E. B., Gnanadesikan, R. and Kettenring, J. R. (1987). Variable selection in clustering and other contexts. In Design, Data, and Analysis, by Some Friends of Cuthbert Daniel (C. L. Mallows, ed.). Wiley, New York, to appear.

Friedman, H. P. and Rubin, J. (1967). On some invariant criteria for grouping data. Journal of American Statistical Association 62 1159-1178.

Friedman, J. H. and Tukey, J. W. (1974). A projection pursuit algorithm for exploratory data analysis. IEEE Trans. Comput. C-23 881-889.

Ganu, Gayatree, Yogesh Kakodkar, and AméLie Marian. "Improving the quality of predictions using textual information in online user reviews." Information Systems 38.1 (2013): 1-15.

Gao, J., Hu, W., Zhang, Z. M., & Wu, O. (2012). Unsupervised ensemble learning for mining top-n outliers. In Advances in Knowledge Discovery and Data Mining (pp. 418-430). Springer Berlin Heidelberg.

Ghaemi, Reza, et al. "A novel fuzzy C-means algorithm to generate diverse and desirable cluster solutions used by genetic-based clustering ensemble algorithms." Memetic Computing 4.1 (2012): 49-71.

Gnanadesikan, R. (1977). Methods for Statistical Data Analysis of Multivariate Observations. Wiley, New York.

Gnanadesikan, R. and Kettenring, J. R. (1984). A pragmatic review of multivariate methods in applications. In Statistics: An Appraisal. (H. A. David and H. T. David, eds.).

Gnanadesikan, R., Kettenring, J. R. and Landwehr, J. M. (1982). Projection plots for displaying clusters. In Statistics and Probability: Essays in Honor of C. R. Rao. (G. Kallianpur, P. R. Krishnaiah and J. K. Ghosh, eds.) 281-294. North-Holland, Amsterdam.

Gnanadesikan, R., Kettenring, J. R., and Landwehr, J. M. (1977). Interpreting and assessing the results of cluster analyses. Bull Int. Statis. Inst. 47451-463.

Goldman, L., Weinberg, M., Weisberg, M., Olshen, R., Cook, F., Sargent, R. K., Lamas, G. A., Dennis, C., Deckelbam, L., Fineberg, H., Stiratelu, R. and the Medical Housestaffs At Yale-New Haven Hospital and Brigham and Women's Hospital (1982). A computer-derived protocol to aid in the diagnosis of emergency room patients with acute chest pain. The New England Journal of Medicine 307588-596.

Gong, G. (1982). Cross-validation, the jackknife, and the bootstrap: excess error estimation in forward logistic regression. Ph.D. dissertation. Stanford University Technical Report No. 80. Department of Statistics.

Gordon, L. and Olshen, R. A. (1978). Asymptotically efficient solutions to the classification problem. Ann. Statist. 6 515-533.

Gordon, L. and Olshen, R. A. (1980). Consistent nonparametric regression from recursive partitioning schemes. J. Mult. Anal. 10 611-627.

Gordon, L. and Olshen, R. A. (1984). Almost surely consistent nonparametric regression from recursive partitioning schemes. J. Mult. Anal. 15 147-163.

Gower, J. C. and Ross, G. J. S. (1969). Minimum spanning trees and single linkage cluster analysis. Appl. Statist. 18 54-65.

Gray, J. B. and Ling, R. F. (1984). K-clustering as a detection tool for influential subsets regression (with discussion). Technometrics 26 305-330.

Gulhane, Ashwini, Prashant L. Paikrao, and D. S. Chaudhari. "A review of image data clustering techniques." International Journal of Soft Computing and Engineering 2.1 (2012): 212-215.

Gulten, Sitki, and Andrzej Ruszczynski. "Two-stage portfolio optimization with higher-order conditional measures of risk." Annals of Operations Research 229.1 (2015): 409-427.

Haff, L. R. (1986). On linear log-odds and estimation of discriminant coefficients. Commun. Statist.—Theor. Meth. 15 2131-2144.

Halkidi, M., Y. Batistakis, and M. Vazirgiannis. Cluster validity methods: part I. SIGMOD Record (ACM Special Interest Group on Management of Data), 31(2):40-45, June 2002.

Halkidi, M., Y. Batistakis, and M. Vazirgiannis. Clustering validity checking methods: part II. SIGMOD Record (ACM Special Interest Group on Management of Data), 31 (3):19-27, September 2002.

Hall, D. J. and Khanna, D. (1977). The ISODATA method of computation for relative perception of similarities and differences in complex and real data. In Statistical Methods for Digital Computers (Vol. 3). (K Enslein, A. Ralston, and H. W. Wilf, eds.) New York: John Wiley.

Hamerly, G. and C. Elkan. Alternatives to the k-means algorithm that find better clusterings. In Proc. of the 11th Intl. Conf. on Information and Knowledge Management, pages 600-607, McLean, Virginia, 2002. ACM Press.

Han, J., M. Kamber, and A. Tung. Spatial Clustering Methods in Data Mining: A review. In H. J. Miller and J. Han, editors, Geographic Data Mining and Knowledge Discovery, pages 188-217. Taylor and Francis, London, December 2001.

Hand, D. J. (1981). Discrimination and Classification. Wiley, New York.

Hartigan, J. A. (1967). Representation of similarity matrices by trees. J Amer. Statist. Assoc. 62 1140-1158.

Hartigan, J. A. (1975). Clustering Algorithms. Wiley, New York.

Hartigan, J. A. (1977). Distribution problems in clustering. In Classification and Clustering (J. Van Ryzin, ed.) 45-71. Academic Press, New York.

Hartigan, J. A. (1978). Asymptotic distributions for clustering criteria. Ann. Statist. 6 117-131.

Hartigan, J. A. (1981). Consistency of single linkage for high density clusters. J. Amer. Statist Assoc. 76388-394.

Hartigan, J. A. and Hartigan, P. M. (1985). The dip test of multimodality. Ann. of Statist. 1370-84.

Hastie, T., R. Tibshirani, and J. H. Friedman. The Elements of Statistical Learning: Data Mining, Inference, Prediction. Springer, New York, 2001.

Hermans, J., Habbema, J., and Schaefer, R. (1982). The ALLOC80 package for discriminant analysis, Stat. Software Newsletter, 8 15-20.

Hodge, V., Tom Jackson, and Jim Austin. "Intelligent decision support using pattern matching." Proceedings of the 1st International Workshop on Future Internet Applications for Traffic Surveillance and Management (FIATS-M 2011), Sofia, Bulgaria. 2011.

Hodson, F. R., Sneath, P. H. A. and Doran, J. E. (1966). Some experiments in the numerical analysis of archaeological data. Biometrika 53311-324.

Hosmer, D. W. (1973). A comparison of iterative maximum likelihood estimates of the parameters of a mixture of two normal distributions under three different typos of sample. Biometrics 29761-770.

Huber, P. J. (1985). Projection pursuit (with discussion). Ann. Statist. 6701-726. International Mathematical and Statistical Library (1977). Reference manual library 1, ed. 6. Vol. 1. Houston.

Ilango, V., R. Subramanian, and V. Vasudevan. "A Five Step Procedure for Outlier Analysis in Data Mining." European Journal of Scientific Research 75.3 (2012): 327-339.

Jain, A. K. and R. C. Dubes. Algorithms for Clustering Data. Prentice Hall Advanced Reference Series. Prentice Hall, March 1988. www.cse.msu.edu/~jain/Clustering Jain Dubes.pdf.

Jain, A. K., M. N. Murty, and P. J. Flynn. Data clustering: A review. ACM Computing Surveys, 31(3):264-323, September 1999.

Jambu, M. and Lebeaux, M. O. (1983). Cluster Analysis and Data Analysis. North-Holland Publishing Company, Amsterdam.

James, W. and Stein, C. (1961). Estimation with quadratic loss. Proc. Fourth Berkeley Symp. Math. Statist. Prob. 1 311-319.

Jardine, C. J., Jardine, N. and Sibson, R. (1967). The structure and construction of taxonomic hierarchies. Math. Biosci. 1 173-179.

Jardine, N. and R. Sibson. Mathematical Taxonomy. Wiley, New York, 1971.

Jayasimhan, Anusha, and Jayant Gadge. "Anomaly Detection using a Clustering Technique." International Journal of Applied Information Systems (IJAIS)-ISSN (2012): 2249-0868.

Jennrich, R. and Moore, R. H. (1975). Maximum likelihood estimation by means of nonlinear least squares. Proceedings of the Statistical Computing Section, American Statistical Association, 57-65.

Jennrich, R. I. (1962). Linear Discrimination in the Case of Unequal Covariance Matrices. Unpublished manuscript.

Joenväärä, Juha, Robert Kosowski, and Pekka Tolonen. "Revisiting "stylized facts" about hedge funds." Imperial College Business School (2012).

Johnson, S. C. (1967). Hierarchical clustering schemes. Psychometrika 32241-254.

Jouis, Christophe; Biskri, Ismail; Ganascia, Jean-Gabriel; Roux, Magali, "Next Generation Search Engines", IGI GlobalPub, Mar. 31, 2012 (ISBN-10: 1-4666-0330-5).

Karypis, G., CLUTO 2.1.1: Software for Clustering High-Dimensional Datasets. www.cs.umn.edu/~karypis, November 2003.

Karypis, G., E.-H. Han, and V. Kumar. Multilevel Refinement for Hierarchical Clustering. Technical Report TR 99-020, University of Minnesota, Minneapolis, MN, 1999.

Kaufman, L. and P. J. Rousseeuw. Finding Groups in Data: An Introduction to Cluster Analysis. Wiley Series in Probability and Statistics. John Wiley and Sons, New York, November 1990.

Keshavarzi, M., M. A. Dehghan, and M. Mashinchi. "Applications of classification based on similarities and dissimilarities." Fuzzy Information and Engineering 4.1 (2012): 75-91.

Kettenring, J. R., Rogers, W. H., Smith, M. E., and Warner, J. L. (1976). Cluster analysis applied to the validation of course objectives. J. Educ. Statist. 1 39-57.

Kitto, Kirsty, and Fabio Boschetti. "Attitudes, ideologies and self-organisation: Information load minimisation in multi-agent decision making." Advances in Complex Systems 16.2 (2013).

Kleinberg, J. M. An Impossibility Theorem for Clustering. In Proc. of the 16th Annual Conf. on Neural Information Processing Systems, December 9-14, 2002.

Kleiner, B. and Hartigan, J. A. (1981). Representing points in many dimensions by trees and castles (with discussion). j Amer. Statist. Assoc. 76260-276.

Krulis̆, Martin, Tomis̆ Skopal, Jakub Lokoc̆, and Christian Beecks. "Combining CPU and GPU architectures for fast similarity search." Distributed and Parallel Databases 30, no. 3-4 (2012): 179-207.

Kumar, B. Santhosh, V. Vijayaganth, Data Clustering Using K-Means Algorithm For High Dimensional Data, International Journal of Advanced Research In Technology (ijart.org); 2(1)22-32, February 2012

Lachenbruch P. A. (1975) Discriminant Analysis. Hafner Press, New York.

Lachenbruch, P. A. (1982). Robustness of discriminant flirictions. SUGI-SAS Group Proceedings 7626-632.

Landwehr J. M., Pregibon, D., and Shoemaker, K C. (1984). Graphical methods for assessing logistic regression models (with discussion). J Amer. Statist. Assoc. 7961-83.

Larsen, B. and C. Aone. Fast and Effective Text Mining Using Linear-Time Document Clustering. In Proc. of the 5th Intl. Conf. on Knowledge Discovery and Data Mining, pages 16-22, San Diego, California, 1999. ACM Press.

Le Capitaine, Hoel. "A relevance-based learning model of fuzzy similarity measures." IEEE Transactions on Fuzzy Systems 20, no. 1 (2012): 57-68.

Le, Hai-Son Phuoc. "Probabilistic Models for Collecting, Analyzing, and Modeling Expression Data." (2013).

Lee, Kwangchun, and Dan Hyung Lee. "A Market-Driven Product Line Scoping." Software Engineering Research, Management and Applications 2011. Springer Berlin Heidelberg, 2012. 27-46.

Lennington, R. K. and Rossbach, M. E. (1978). CLASSY: An adaptive maximum likelihood clustering algorithm. Paper presented at 1978 meeting of the Classification Society.

Levisohn, J. R. and Funk, S. G. (1974). CLUSTER: A hierarchical clustering program for large data sets (n>100). Research Memo #40, Thurstone Psychometric Laboratory, University of North Carolina.

Li, Youguo, and Haiyan Wu. "A clustering method based on K-means algorithm." Physics Procedia 25 (2012): 1104-1109.

Ling, R. F. (1973). A probability theory of cluster analysis. J. Amer. Statist. Assoc. 68159-169.

Liu, Keke Chen Ling. "Vista: Looking Into the Clusters in Very Large Multidimensional Datasets." Technical; Report GIT-CC-02-30 (2002).

Lloret, Elena, et al. "Towards a unified framework for opinion retrieval, mining and summarization." Journal of Intelligent Information Systems 39.3 (2012): 711-747.

Loohach, Richa, and Kanwal Garg. "An Insight Overview Of Issues And Challenges Associated With Clustering Algorithms." mairec.org Lou, Xiaojun, Junying Li, and Haitao Liu. "Improved Fuzzy C-means Clustering Algorithm Based on Cluster Density Related Work." Journal of Computational Information Systems 2 (2012): 72.

Macqueen, J. (1967). Some methods for classification and analysis of multivariate observations. Proc. Fifth Berkeley Symp. Math. Statist. Prob. 1281-297.

MacQueen, J. Some methods for classification and analysis of multivariate observations. In Proc. of the 5th Berkeley Symp. on Mathematical Statistics and Probability, pages 281-297. University of California Press, 1967.

Madhulatha, T. Soni. "An overview on clustering methods." arXiv preprint arXiv:1205.1117 (2012).

Marks, S. and Dunn, O. J. (1974). Discriminant functions when covariance matrices are unequal. J. Amer. Statist. Assoc. 69, 555-559.

Martinez, Sergio, Aida Valls, and David SáNchez. "Semantically-grounded construction of centroids for datasets with textual attributes." Knowledge-Based Systems 35 (2012): 160-172.

Mccullagh, P. and Nelder, J. A. (1983). Generalized Linear Models. Chapman and Hall, London.

Mckay, R. J. (1978). A graphical aid to selection of variables in two-group discriminant analysis. Appl. Statist. 27259-263.

Mckay, R. J. and Campbell, N. A. (1982a). Variable selection techniques in discriminant analysis. 1. Description. Br. J. Math. Stat. Psychol. 351-29.

Mckay, R. J. and Campbell, N. A. (1982b). Variable selection techniques in discriminant analysis. II. Allocation. Br. J. Math. Stat. Psychol. 353041.

Mianowska, Bernadetta, and Ngoc Thanh Nguyen. "Tuning user profiles based on analyzing dynamic preference in document retrieval systems." Multimedia tools and applications 65.1 (2013): 93-118.

Michener, C. D. and Sokal R. R. (1957). A quantitative approach to a problem in classification. Evolution ii 130-162.

Milligan, G. W. Clustering Validation: Results and Implications for Applied Analyses. In P. Arabie, L. Hubert, and G.

D. Soete, editors, Clustering and Classification, pages 345-375. World Scientific, Singapore, January 1996.

Mirkin, B. Mathematical Classification and Clustering, volume 11 of Nonconvex Optimization and Its Applications. Kluwer Academic Publishers, August 1996.

Mitchell, T. Machine Learning. McGraw-Hill, Boston, MA, 1997.

Mojena, R. (1977). Hierarchical grouping methods and stopping rules—An evaluation. Computer Journal 20359-363.

Mojena, R. and Wishart, D. (1980). Stopping rules for Ward's clustering method. Proceedings of COMPSTAT. Physica Verlag 426-432.

Morgan, J. N. and Messenger, R. C. (1973). THMD: a sequential search program for the analysis of nominal scale dependent variables. Institute for Social Research, U of Michigan, Ann Arbor.

Morgan, J. N. and Sonquist, J. A. (1963). Problems in the analysis of survey data, and a proposal. J. Amer. Statist. Assoc. 58415-435.

Murtagh, F. Multidimensional Clustering Algorithms. Physica-Verlag, Heidelberg and Vienna, 1985.

Naresh, Tangudu, G. Ramesh Naidu, and S. Vishnu Murty. "Learning Subject Areas by Using Unsupervised Observation of Most Informative Terms in Text Databases." International Journal of Computer Science 1.1-2 (2012).

Navarro-Arribas, Guillermo, and Vicenç Torra. "Information fusion in data privacy: A survey." Information Fusion 13.4 (2012): 235-244.

Nelder, J. A. and Wedderburn, R. W. M. (1972). Generalized linear models. J Roy. Statist. Soc. A 135 370-384.

Olshen, R. A., Gilpin, E., Henning, H. Lewinter, M., Collins, D., and Ross, J., Jr. (1985). Twelve month prognosis following myocardial infarction: classification trees, logistic regression, and stepwise linear discrimination. Proceedings of the Berkeley Conference in Honor of Jerzy Neyman and Jack Kiefer. (L. LeCam and R. Olshen, eds.) 1 245-267. Wadsworth Advanced Books and Software, Monterey, California and the Institute of Mathematical Statistics, Hayward, California Pedronette, Daniel Carlos Guimarães, and Ricardo da S. Torres. "Exploiting pairwise recommendation and clustering strategies for image re-ranking." Information Sciences 207 (2012): 19-34.

Pelleg, D. and A. W. Moore. X-means: Extending K-means with Efficient Estimation of the Number of Clusters. In Proc. of the 17th Intl. Conf. on Machine Learning, pages 727-734. Morgan Kaufmann, San Francisco, California, 2000.

Peters, Georg, and Richard Weber. "Dynamic clustering with soft computing." Wiley Interdisciplinary Reviews: Data Mining and Knowledge Discovery 2.3 (2012): 226-236.

Pivovarov, Rimma, and Noémie Elhadad. "A hybrid knowledge-based and data-driven approach to identifying semantically similar concepts." Journal of biomedical informatics 45.3 (2012): 471-481.

Pollard, D. (1982). A central limit theorem for k-means clustering. Ann. Prob. 10919-926.

Pregibon, D. (1981). Logistic regression diagnostics. Ann. Statist. 9 705-724.

Rabiner, L. R., Levinson, S. E., Rosenberg, A. E. and Wilpon, J. G. (1979). Speaker independent recognition of isolated words using clustering techniques. IEEE Trans. Accoust. Speech Signal Process. 27336-349.

Rao, C. R. (1948). The utilization of multiple measurements in problems of biological classification. J. Roy. Statist. Soc. Ser. B 10159-203.

Rao, C. R. (1952). Advanced Statistical Methods in Biometric Research. Wiley, New York.

Rao, C. R. (1960). Multivariate analysis: an indispensable statistical aid in applied research. Sankhya 22317-338.

Rao, C. R. (1962). Use of discriminant and allied functions in multivariate analysis.

Sankhya A24 149-154.

Rao, C. R. (1965). Linear Statistical Inference and Its Applications. Wiley, New York.

Richhariya, Pankaj, et al. "A Survey on Financial Fraud Detection Methodologies." International Journal of Computer Applications 45.22 (2012).

Riffenburgh, R. H. and Clunies-Ross, C. W. (1960). Linear discriminant analysis. Pacific Science 14 251-256.

Ríos, Sebastián A., Roberto A. Silva, and Felipe Aguilera. "A dissimilarity measure for automate moderation in online social networks." Proceedings of the 4th International Workshop on Web Intelligence & Communities. ACM, 2012.

Robinson, Lucy F., and Carey E. Priebe. "Detecting time-dependent structure in network data via a new class of latent process models." arXiv preprint arXiv:1212.3587 (2012).

Rohlf, F. J. (1977). Computational efficacy of agglomerative clustering algorithms. Technical Report RC-6831. IBM Watson Research Center Rohlf, F. J. (1982). Single-link clustering algorithms. In Handbook of Statistics: Vol. 2, (P. R. Krishnaiah and L. N. Kanal, eds.) 267-284. North-Holland Publishing Company, Amsterdam.

Romesburg, C. Cluster Analysis for Researchers. Life Time Learning, Belmont, C A, 1984.

Roshchina, Alexandra, John Cardiff, and Paolo Rosso. "Evaluating the Similarity Estimator Component of the TWIN Personality-based Recommender System." (2012).

Rotman, S. R., Fisher, A. D., and Staelin, D. H. (1981). Analysis of multiple-angle microwave observations of snow and ice using cluster analysis techniques. J. Glaciology 27 89-97.

Rousu, Juho. "Efficient range partitioning in classification learning." Department of Computer Science, University of Helsinki. 2001.

Ryan, T., Joiner, B., and Ryan, B. (1982). Minitab Reference Manual. Duxbury Press, Boston.

Rybina, Kateryna. Sentiment analysis of contexts around query terms in documents. Diss. Master's thesis, 2012.

Salman, Raied. "Contributions to K-means clustering and regression Via classification algorithms." (2012).

Sander, J., M. Ester, H.-P. Kriegel, and X. Xu. Density-Based Clustering in Spatial Databases: The Algorithm GDBSCAN and its Applications. Data Mining and Knowledge Discovery, 2(2):169-194, 1998.

SAS Institute, Inc. (1985). SAS User's Guide: Statistics, Version S Edition. Sas Institute, Inc., Cary, NC Savaresi, S. M. and D. Boley. A comparative analysis on the bisecting K-means and the PDDP clustering algorithms. Intelligent Data Analysis, 8(4):345-362, 2004.

Schifanella, Claudio, Maria Luisa Sapino, and K. Selçuk Candan. "On context-aware co-clustering with metadata support." Journal of Intelligent Information Systems 38.1 (2012): 209-239.

Schlüter, Tim, and Stefan Conrad. "Hidden markov model-based time series prediction using motifs for detecting inter-time-serial correlations." Proceedings of the 27th Annual ACM Symposium on Applied Computing. ACM, 2012.

Seber, G. A. F. (1984). Multivariate Observations. Wiley, New York.

Sharma, Puneet, Srinivasa M. Salapaka, and Carolyn L. Beck. "Entropy-based framework for dynamic coverage and clustering problems." Automatic Control, IEEE Transactions on 57.1 (2012): 135-150.

Shepard, R. N. and Arabie, P. (1979). Additive clustering: representation of similarities as combinations of discrete overlapping properties. Psychological Review 8687-123.

Shibata, R. (1981). An optimal selection of regression variables. Biometrika 6845-54.

Sibson, R. (1973). SLINK: An optimally efficient algorithm for single-link cluster methods. Computer Journal 1630-34.

Siegel, J. H., Goldwyn, R. M., and Friedman, H. P. (1971). Pattern and process in the evolution of human septic shock. Surgery 70232-245.

Silverman, B. W. (1986). Density Estimation for Statistics and Data Analysis. Chapman and Hall, London.

Smythe, R. T. and Wierman, J. C. (1978). First passage percolation on the square lattice. Lecture Notes in Mathematics 671. Springer-Verlag, Berlin.

Sneath, P. H. A. and R. R. Sokal. Numerical Taxonomy. Freeman, San Francisco, 1971.

Sneath, P. H. A. and Sokal, R. R. (1973). Numerical Taxonomy. Freeman, San Francisco.

Sokal, R. R. (1974). Classification: purposes, principles, progress, prospects. Science 185 1115-1123.

Späth, H. Cluster Analysis Algorithms for Data Reduction and Classification of Objects, volume 4 of Computers and Their Application. Ellis Horwood Publishers, Chichester, 1980. ISBN 0-85312-141-9.

SPSS, INC. (1986). SPSSX (a computer program). McGraw-Hill, New York.

Stahl, Frederic, and Ivan Jordanov. "An overview of the use of neural networks for data mining tasks." Wiley Interdisciplinary Reviews: Data Mining and Knowledge Discovery 2.3 (2012): 193-208.

Stein, C. (1956). Inadmissibility of the usual estimator for the mean of a multivariate normal distribution. Third Berkeley Symp. Math. Statist. Prob. 1 197-206.

Steinbach, M., G. Karypis, and V. Kumar. A Comparison of Document Clustering Techniques. In Proc. of KDD Workshop on Text Mining, Proc. of the 6th Intl. Conf. on Knowledge Discovery and Data Mining, Boston, MA, August 2000.

Stone, C. J. (1977). Consistent nonparametric regression (with discussion). Ann. Statist. 5595-645.

Stone, M. (1977). Cross-validation: a review. Math. Operationforsch. Statist. Ser. Statist. 9 127-139.

Streib, Amanda Pascoe. "Markov chains at the interface of combinatorics, computing, and statistical physics." (2012).

Su, Yu, and Frédéric Jurie. "Improving image classification using semantic attributes." International journal of computer vision 100.1 (2012): 59-77.

Sundaram, Hari, et al. "Understanding community dynamics in online social networks: a multidisciplinary review." Signal Processing Magazine, IEEE 29.2 (2012): 33-40.

Swamy, G. M., P. McGeer, R. Brayton, In the Pro¬ceedings of the International Workshop on Logic Synthesis, Tahoe CA, May 1993 "A Fully Implicit Quine-McClusky Procedure using BDDs".

Swamy, G. M., S. Edwards, R. Brayton, In the Proceedings of the IEEE International Conference on VLSI Design, Hyderabad, January 1998. "Efficient Verification and Synthesis using Design Commonalities".

Swamy, Gitanjali, R, Brayton, ISBN:0-591-32212-9, University of California, Berkeley, 1996 Incremental methods for formal verification and logic synthesis".

Tarter, M. and Kronmal, R. (1970). On multivariate density estimates based on orthogonal expansions. Ann. Math. Statist. 4 718-722.

Thuett, J., Cornfield, J. and Kannel, W. (1967). A multivariate analysis of the risk of coronary heart disease in Framingham. J of Chronic Diseases 20511-524.

Thyon, R. C. (1939). Cluster Analysis. Edwards Brothers, Ann Arbor, MI

Tidke, B. A., R. G. Mehta, and D. P. Rana. "A novel approach for high dimensional data clustering." Int J Eng Sci Adv Technology 2.3 (2012): 645-51.

Tilak, Gayatri, et al. "Study of statistical correlations in intraday and daily financial return time series." Econophysics of Systemic Risk and Network Dynamics. Springer Milan, 2013. 77-104.

Toussaint, G. T. (1974). Bibliography on estimation of misclassification. IEEE Transactions on Information Theory IT-20 472A79.

Treerattanapitak, Kiatichai, and Chuleerat Jaruskulchai. "Exponential fuzzy C-means for collaborative filtering." Journal of Computer Science and Technology 27.3 (2012): 567-576.

Tu, Chunhao, Shuo Jiao, and Woon Yuen Koh. "Comparison of clustering algorithms on generalized propensity score in observational studies: a simulation study." Journal of Statistical Computation and Simulation 83.12 (2013): 2206-2218.

Van Giessen, A. N. O. U. K. H. Dimension reduction methods for classification; MRI-based automatic classification of Alzheimer's disease. Diss. TU Delft, Delft University of Technology, 2012.

Vandic, Damir, Jan-Willem Van Dam, and Flavius Frasincar. "Faceted product search powered by the Semantic Web." Decision Support Systems 53.3 (2012): 425-437.

Vapnik, V. N. and Chervonenkis, A. YA. (1971). On the uniform convergence of relative frequencies of events to their probabilities. Theor. Prob. Appl. 16264-280.

Vapnik, V. N. and Chervonenkis, A. YA. (1974). Theory of Pattern Recognition (in Russian). Nauka, Moscow.

Vasconcelos, Cristina Nader, et al. "Photo Tagging by Collection-Aware People Recognition." (2012).

Vasileios, Efthymiou, and Grigoris Antoniou. "A real-time semantics-aware activity recognition system." (2012).

Veldman, D. J. (1967). FORTRAN Programming for the Behavioral Sciences. Holt, Rinehart and Winston, New York.

Vlachos, Michail, and Daniel Svonava. "Recommendation and visualization of similar movies using minimum spanning dendrograms." Information Visualization (2012): 1473871612439644.

Volkovich, Zeev, Dvora Toledano-Kitai, and G-W. Weber. "Self-learning K-means clustering: a global optimization approach." Journal of Global Optimization (2013): 1-14.

Volkovich, Zeev, et al. "On an adjacency cluster merit approach." International Journal of Operational Research 13.3 (2012): 239-255.

Vrijenhoek, R. C., Douglas, M. E., and Meffe, G. K— (1985). Conservation genetics of endangered fish populations in Arizona. Science 229 100-402.

Wald, A. (1944). On a statistical problem arising in the classification of an individual into one of two groups. Ann. Math. Statist. 15145-162.

Walker, S. B. and Duncan, D. B. (1967). Estimation of the probability of an event as a function of several independent variables. Biometrika 54 167-179.

Wan, Chin Heng, et al. "A hybrid text classification approach with low dependency on parameter by integrating K-nearest neighbor and support vector machine." Expert Systems with Applications 39.15 (2012): 11880-11888.

Wang, Baohua, and Xiaolong Wang. "Deceptive Financial Reporting Detection: A Hierarchical Clustering Approach Based on Linguistic Features." Procedia Engineering 29 (2012): 3392-3396.

Wang, Jinlong, Shunyao Wu, and Gang Li. "Clustering with instance and attribute level side information." International journal of computational intelligence systems 3.6 (2010): 770-785.

Wang, Ziqiang, Xia Sun, and Xu Qian. "Efficient Kernel Discriminative Geometry Preserving Projection for Document Classification." Przegląd Elektrotechniczny 88.5b (2012): 56-59.

Watve, Alok. Data Transformation for Improved Query Performance. Diss. Michigan State University, 2012.

Wishart, D. (1969). Mode Analysis: A generalization of nearest neighbor which reduces chaining effects in Numerical Taxonomy, (A. J. Cole, ed.), Academic Press, London.

Wolfe, J. H. (1970). Pattern clustering by multivariate mixture analysis. Multivariate Behavioral Research S 329-350.

Wolfe, J. H. (1971). A Monte-Carlo study of the sampling distribution of the likelihood ratio for mixtures of multinormal distributions. Research Memorandum 72-2, Naval Personnel and Research Training Laboratory, San Diego.

Wu, H. C., et al. "A split-list approach for relevance feedback in information retrieval." Information Processing & Management 48.5 (2012): 969-977.

Xu, Rui, Jie Xu, and Donald C. Wunsch. "A comparison study of validity indices on swarm-intelligence-based clustering." Systems, Man, and Cybernetics, Part B: Cybernetics, IEEE Transactions on 42.4 (2012): 1243-1256.

Yang, Di. Mining and Managing Neighbor-Based Patterns in Data Streams. Diss. Worcester Polytechnic Institute, 2012.

Zahn, C. T. Graph-Theoretical Methods for Detecting and Describing Gestalt Clusters. IEEE Transactions on Computers, C-20(1):68-86, January 1971.

Zhang, B., M. Hsu, and U. Dayal. K-Harmonic Means—A Data Clustering Algorithm. Technical Report HPL-1999-124, Hewlett Packard Laboratories, Oct. 29 1999.

Zhang, Yi. Learning with Limited Supervision by Input and Output Coding. Diss. University of Wisconsin-Madison, 2012.

Zhao, Y. and G. Karypis. Empirical and theoretical comparisons of selected criterion functions for document clustering. Machine Learning, 55(3):311-331, 2004.

Zheng, H. T. and Jiang, Y., 2012. Towards group behavioral reason mining. Expert Systems with Applications, 39(16), pp. 12671-12682.

Zhou, Xueyuan. Learning functions on unknown manifolds. The University of Chicago, 2011.

Zuccolotto, Paola. "Principal component analysis with interval imputed missing values." AStA Advances in Statistical Analysis 96.1 (2012): 1-23.

Each of the following is expressly incorporated herein by reference in its entirety, for example, for its disclosure of clustering technology, applications of that technology, and implementations: 20120137182; 20120136860; 20120131701; 20120125178; 20120123279; 20120109778; 20120089341; 20120088981; 20120084251; 20120078927; 20120078906; 20120078858; 20120076372; 20120072124; 20120070452; 20120054133; 20120047098; 20120045119; 20120041955; 20120039541; 20120036096; 20120030185; 20120030165; 20120021710; 20120015841; 20120014560; 20120011135; 20120005238; 20110320396; 20110306354; 20110304619; 20110301860; 20110299765; 20110295773; 20110288890; 20110282877; 20110282828; 20110269479; 20110264432; 20110261049; 20110255748; 20110255747; 20110251081; 20110246483; 20110246409; 20110246200; 20110231414; 20110225158; 20110221767; 20110218990; 20110206246; 20110205399; 20110202540; 20110191353; 20110191283; 20110191076; 20110185234; 20110179019; 20110178965; 20110175905; 20110173189; 20110173173; 20110172501; 20110166949; 20110161205; 20110144914; 20110144480; 20110143650; 20110142318; 20110142287; 20110124525; 20110119108; 20110116690; 20110115787; 20110106801; 20110105350; 20110105340; 20110103613; 20110097001; 20110093492; 20110093482; 20110091083; 20110091074; 20110091073; 20110086349; 20110081066; 20110081056; 20110080490; 20110078144; 20110078143; 20110060717; 20110060716; 20110055192; 20110052076; 20110048731; 20110047172; 20110040192; 20110029657; 20110022599; 20110022354; 20110020779; 20110015869; 20110013840; 20110008805; 20110004578; 20110004415; 20110004115; 20110002194; 20110002028; 20100332475; 20100332474; 20100332425; 20100332242; 20100332210; 20100322525; 20100318492; 20100313157; 20100305930; 20100305868; 20100299128; 20100296748; 20100284915; 20100280987; 20100278425; 20100268512; 20100268476; 20100257092; 20100254614; 20100250527; 20100250477; 20100239147; 20100232718; 20100228731; 20100228625; 20100221722; 20100217763; 20100216660; 20100215903; 20100205213; 20100204061; 20100199186; 20100198864; 20100191722; 20100191532; 20100189333; 20100183555; 20100174985; 20100174983; 20100174982; 20100174980; 20100174979; 20100174978; 20100174977; 20100174976; 20100174732; 20100174492; 20100169025; 20100166339; 20100161590; 20100161232; 20100157340; 20100157089; 20100150453; 20100149917; 20100138894; 20100136553; 20100135597; 20100135582; 20100125594; 20100121638; 20100117978; 20100114929; 20100114928; 20100112234; 20100111396; 20100111370; 20100106713; 20100100515; 20100085358; 20100082614; 20100082367; 20100081661; 20100080439; 20100076981; 20100067745; 20100057534; 20100057399; 20100057391; 20100055678; 20100054278; 20100050260; 20100049431; 20100042563; 20100036647; 20100034422; 20100033182; 20100017487; 20100005105; 20100004923; 20100004898; 20090327185; 20090326383; 20090319526; 20090319454; 20090318815; 20090313294; 20090311786; 20090299990; 20090299822; 20090299705; 20090297048; 20090292802; 20090292695; 20090292694; 20090292482; 20090290778; 20090287689; 20090277322; 20090276705; 20090271694; 20090271424; 20090271405; 20090271404; 20090271397; 20090271363; 20090271359; 20090271246; 20090265024; 20090252046; 20090248399; 20090234876; 20090226081; 20090222430; 20090220488; 20090204609; 20090204574; 20090204333; 20090199099; 20090190798; 20090175545; 20090175544; 20090169065; 20090164192; 20090154795; 20090150340; 20090132347; 20090125916; 20090125482; 20090124512; 20090104605; 20090097728; 20090094265; 20090094233; 20090094232;

20090094231; 20090094209; 20090094208; 20090094207; 20090094021; 20090094020; 20090093717; 20090083211; 20090081645; 20090080777; 20090077093; 20090070346; 20090063537; 20090060042; 20090055257; 20090055147; 20090048841; 20090043714; 20090028441; 20090024555; 20090022472; 20090022374; 20090012766; 20090010495; 20090006378; 20080319973; 20080310005; 20080302657; 20080300875; 20080300797; 20080275671; 20080267471; 20080263088; 20080261820; 20080261516; 20080260247; 20080256093; 20080249414; 20080243839; 20080243817; 20080243816; 20080243815; 20080243638; 20080243637; 20080234977; 20080232687; 20080226151; 20080222225; 20080222075; 20080221876; 20080215510; 20080212899; 20080208855; 20080208828; 20080201397; 20080198231; 20080198160; 20080191035; 20080189306; 20080188964; 20080183546; 20080182282; 20080181479; 20080177640; 20080177538; 20080162541; 20080155335; 20080152231; 20080147655; 20080147591; 20080147441; 20080147440; 20080147438; 20080146334; 20080144943; 20080126464; 20080123940; 20080114800; 20080114756; 20080114710; 20080114564; 20080112684; 20080109288; 20080101705; 20080097820; 20080091423; 20080082426; 20080077570; 20080069437; 20080057590; 20080037872; 20080037536; 20080033658; 20080030836; 20080010605; 20080010273; 20080010272; 20080010262; 20080010045; 20080005137; 20070291958; 20070288465; 20070286489; 20070285575; 20070276723; 20070275108; 20070269804; 20070263900; 20070255707; 20070250522; 20070244768; 20070239982; 20070239741; 20070239694; 20070233711; 20070231921; 20070217676; 20070198553; 20070192063; 20070192034; 20070185946; 20070180980; 20070179784; 20070174335; 20070172803; 20070156516; 20070154931; 20070154066; 20070150443; 20070141527; 20070129991; 20070129011; 20070128573; 20070111316; 20070106405; 20070093966; 20070092905; 20070092888; 20070078846; 20070067212; 20070064627; 20070054266; 20070050708; 20070044010; 20070038612; 20070033533; 20070033521; 20070033515; 20070033292; 20070033221; 20070033214; 20070033170; 20070025637; 20070022279; 20070008905; 20070006177; 20070005556; 20070003138; 20060282425; 20060282298; 20060281473; 20060253258; 20060248141; 20060246495; 20060239338; 20060224356; 20060212337; 20060208185; 20060195415; 20060195269; 20060195204; 20060190465; 20060190191; 20060177837; 20060136589; 20060112146; 20060106816; 20060101377; 20060101060; 20060095521; 20060093208; 20060093188; 20060074924; 20060074771; 20060074621; 20060064177; 20060058592; 20060053142; 20060053129; 20060052943; 20060041414; 20060034545; 20060031219; 20060020662; 20060015630; 20060015341; 20060013482; 20050286774; 20050285937; 20050283328; 20050281291; 20050278324; 20050273319; 20050267993; 20050267992; 20050267991; 20050265331; 20050262044; 20050256413; 20050255458; 20050251882; 20050225678; 20050198575; 20050193216; 20050192768; 20050185848; 20050182570; 20050180638; 20050176057; 20050175244; 20050164273; 20050163384; 20050163373; 20050149269; 20050147303; 20050138056; 20050137806; 20050132069; 20050130230; 20050130215; 20050120105; 20050114331; 20050102305; 20050102272; 20050085436; 20050075995; 20050058336; 20050027829; 20050015376; 20050010571; 20040267774; 20040260694; 20040254901; 20040249939; 20040249789; 20040243362; 20040233987; 20040230586; 20040213461; 20040181527; 20040177069; 20040175700; 20040172225; 20040171063; 20040170318; 20040162834; 20040162647; 20040139067; 20040130546; 20040129199; 20040127777; 20040122797; 20040107205; 20040103377; 20040101198; 20040091933; 20040075656; 20040071368; 20040068332; 20040056778; 20040049517; 20040048264; 20040036716; 20040024773; 20040024758; 20040024739; 20040019574; 20040013292; 20040003005; 20040002973; 20040002954; 20030229635; 20030208488; 20030205124; 20030175720; 20030174179; 20030161500; 20030161396; 20030158842; 20030145014; 20030139851; 20030138978; 20030129660; 20030120630; 20030107768; 20030101003; 20030100996; 20030097357; 20030097356; 20030093227; 20030088563; 20030078509; 20030078494; 20030074251; 20030065661; 20030065635; 20030061249; 20030059081; 20030058339; 20030054573; 20030050923; 20030050908; 20030046253; 20030046018; 20030044062; 20030044053; 20030036093; 20030033138; 20030028564; 20030016250; 20030014191; 20030009469; 20030009333; 20020191034; 20020190198; 20020184080; 20020183966; 20020181786; 20020181711; 20020147703; 20020146175; 20020143989; 20020132479; 20020131641; 20020129038; 20020128781; 20020122587; 20020115070; 20020111966; 20020099721; 20020099675; 20020091655; 20020069218; 20020050990; 20020049740; 20020033835; 20020023061; 20020002555; 20020002550; 20020000986; 20010055019; 20010048753; 20010014868; 20010000356; U.S. Pat. Nos. 8,200,648; 8,200,506; 8,195,734; 8,195,670; 8,195,345; 8,191,783; 8,190,863; 8,190,082; 8,184,913; 8,183,050; 8,180,766; 8,180,627; 8,180,147; 8,175,896; 8,175,730; 8,175,412; 8,170,961; 8,170,306; 8,169,681; 8,169,481; 8,165,407; 8,165,406; 8,164,507; 8,150,169; 8,145,669; 8,139,838; 8,135,719; 8,135,681; 8,135,680; 8,135,679; 8,122,502; 8,122,045; 8,117,213; 8,117,204; 8,117,203; 8,117,139; 8,116,566; 8,108,931; 8,108,405; 8,108,392; 8,099,381; 8,097,469; 8,095,830; 8,095,521; 8,095,389; 8,090,729; 8,082,246; 8,077,984; 8,073,652; 8,065,316; 8,065,248; 8,055,677; 8,051,139; 8,051,082; 8,046,362; 8,041,715; 8,032,476; 8,027,977; 8,019,766; 8,015,183; 8,015,125; 8,015,124; 8,014,957; 8,014,591; 8,010,589; 8,010,466; 8,005,294; 8,000,533; 8,000,527; 7,996,369; 7,991,557; 7,979,435; 7,979,362; 7,975,039; 7,975,035; 7,970,627; 7,966,327; 7,966,225; 7,966,130; 7,962,651; 7,958,096; 7,954,090; 7,953,705; 7,953,679; 7,949,186; 7,937,349; 7,937,234; 7,933,915; 7,933,740; 7,930,189; 7,926,026; 7,917,517; 7,917,306; 7,912,734; 7,912,726; 7,912,290; 7,912,284; 7,904,303; 7,899,564; 7,894,995; 7,894,669; 7,890,512; 7,890,510; 7,890,294; 7,889,914; 7,889,679; 7,885,966; 7,882,126; 7,882,119; 7,879,620; 7,876,947; 7,873,616; 7,868,786; 7,865,456; 7,856,434; 7,849,027; 7,848,567; 7,842,874; 7,835,542; 7,831,549; 7,831,531; 7,831,325; 7,827,183; 7,827,181; 7,826,635; 7,823,055; 7,822,426; 7,813,580; 7,805,496; 7,805,443; 7,805,266; 7,801,893; 7,801,685; 7,783,249; 7,773,784; 7,767,395; 7,761,448; 7,752,208; 7,747,547; 7,747,390; 7,747,054; 7,746,534; 7,743,059; 7,739,284; 7,736,905; 7,716,148; 7,711,846; 7,707,210; 7,702,155; 7,697,785; 7,693,683; 7,689,457; 7,688,495; 7,685,090; 7,684,963; 7,679,617; 7,660,468; 7,657,379; 7,657,126; 7,657,100; 7,650,320; 7,644,090; 7,643,597; 7,639,868; 7,639,714; 7,624,337; 7,613,572; 7,610,306; 7,603,326; 7,599,917; 7,599,799; 7,590,264; 7,584,168; 7,580,682; 7,580,556; 7,574,409; 7,574,069; 7,570,213; 7,567,961; 7,565,432; 7,565,346; 7,565,251; 7,565,213; 7,562,325; 7,562,015; 7,558,425; 7,555,441; 7,552,474; 7,552,131; 7,545,978; 7,539,656; 7,529,732; 7,526,101; 7,519,227; 7,519,209; 7,516,149; 7,512,524; 7,499,916; 7,492,943; 7,487,056; 7,475,085; 7,468,730; 7,464,074; 7,458,050; 7,450,746; 7,450,122; 7,437,308; 7,428,541; 7,428,528; 7,426,301; 7,424,462; 7,418,136; 7,406,200; 7,401,087; 7,397,946; 7,395,250; 7,389,281; 7,386,426; 7,376,752; 7,369,961; 7,369,889; 7,369,680; 7,346,601; 7,337,158; 7,328,363; 7,325,201;

7,296,088; 7,296,011; 7,293,036; 7,287,019; 7,275,018; 7,272,262; 7,263,220; 7,251,648; 7,246,128; 7,246,012; 7,231,074; 7,225,397; 7,222,126; 7,221,794; 7,216,129; 7,215,786; 7,206,778; 7,202,791; 7,196,705; 7,188,055; 7,177,470; 7,174,048; 7,167,578; 7,158,970; 7,142,602; 7,139,739; 7,111,188; 7,068,723; 7,065,587; 7,065,521; 7,062,083; 7,058,650; 7,058,638; 7,054,724; 7,047,252; 7,043,463; 7,039,621; 7,039,446; 7,035,823; 7,035,431; 7,031,980; 7,031,844; 7,016,531; 7,010,520; 6,999,886; 6,993,186; 6,980,984; 6,976,016; 6,970,796; 6,968,342; 6,961,721; 6,954,756; 6,950,752; 6,915,241; 6,912,547; 6,907,380; 6,906,719; 6,904,420; 6,895,267; 6,854,096; 6,845,377; 6,841,403; 6,834,278; 6,834,266; 6,832,162; 6,826,316; 6,819,793; 6,816,848; 6,807,306; 6,804,670; 6,801,859; 6,801,645; 6,799,175; 6,797,526; 6,785,419; 6,785,409; 6,778,981; 6,778,699; 6,763,128; 6,760,701; 6,757,415; 6,751,614; 6,751,363; 6,750,859; 6,735,465; 6,735,336; 6,732,119; 6,711,585; 6,701,026; 6,700,115; 6,684,177; 6,674,905; 6,643,629; 6,636,849; 6,627,464; 6,615,205; 6,594,658; 6,592,627; 6,584,433; 6,564,197; 6,556,983; 6,539,352; 6,535,881; 6,526,389; 6,519,591; 6,505,191; 6,496,834; 6,487,554; 6,473,522; 6,470,094; 6,468,476; 6,466,695; 6,463,433; 6,453,246; 6,445,391; 6,437,796; 6,424,973; 6,424,971; 6,421,612; 6,415,046; 6,411,953; 6,400,831; 6,389,169; 6,373,485; 6,351,712; 6,331,859; 6,300,965; 6,295,514; 6,295,504; 6,295,367; 6,282,538; 6,263,334; 6,263,088; 6,249,241; 6,203,987; 6,192,364; 6,185,314; 6,140,643; 6,122,628; 6,121,969; 6,112,186; 6,100,825; 6,092,049; 6,085,151; 6,049,777; 6,041,311; 5,949,367; 5,940,833; 5,940,529; 5,926,820; 5,920,852; 5,889,523; 5,872,850; 5,813,002; 5,809,490; 5,795,727; 5,764,283; 5,748,780; 5,731,989; 5,724,571; 5,717,915; 5,710,916; 5,699,507; 5,668,897; 5,627,040; 5,625,704; 5,574,837; 5,566,078; 5,506,801; 5,497,486; 5,463,702; 5,448,684; 5,442,792; 5,327,521; 5,285,291; 5,253,307; 5,020,411; 4,965,580; 4,855,923; 4,773,093; 4,257,703; and 4,081,607.

The natural language processing module performs functions to understand human language. For example, the natural language processing module may analyze and extract information (including patient symptom information) from the raw input data, or such extraction may occur outside of the speech recognition per se. That is, the natural language processing module may analyze audio input. A health management application may further extract information from non-verbal (non-speech) portions of audio input (including patient symptom information). For example, the health management application may detect coughing (including whether the cough is dry or productive), wheezing, shortness of breath, sneezing, congestion, sniffling, or any other non-verbal indications of probable symptoms of potential health conditions. The health management application may further extract the emotional state or characteristics of the user. For example, the health management application may determine whether the user is worried, nervous, confident, agitated, annoyed, or in any other emotional state. For example, the machine learning engine may apply one or more ML models trained to extract the emotional state of the user from the audio input. These one or more ML models may be stored in a knowledge database and/or memory module. Further example details of extracting information from audio input can be found in U.S. patent application 20170084295.

The health management application may analyze audio data to detect expressions of symptoms that may be present when a patient is experiencing a particular health condition. In some examples, guideline information may comprise one or more ML models or subprocesses trained or defined to detect whether a user is experiencing particular health conditions. For example, the health management application may determine whether a user is experiencing one or more potential health conditions.

Certain implementations of the disclosed technology may include "real-time" (or "interaction time") prediction of classes based on speech features as well as the integration of acoustic features. The disclosed technical advances include computer-implemented techniques that enable the classes to be predicted accurately and reliably even though short time windows are used to capture the features. As used herein, "real time" or "interactive time" generally refers to the production of a system response without a significant time delay, i.e., within a short enough amount of time that the end user of the system receives the system's response in an interactive fashion, even while a risk encounter prevails. the user is still continuing speaking, in some cases. As used herein, the term "speech" or "speech feature" generally refers to information extracted from the audio signal that pertains to the content of what is heard (e.g., lexical information, or words or phrases) and/or the manner in which the words or phrases are spoken by the particular user (e.g., acoustics, pronunciation, emphasis, loudness, phonetics, timing, pausing, intonation, rhythm, speaking rate, quality of the voice, biometric indicia). Speech or speech features may also include non-lexical information such as laughter, sighing, or breathing patterns, as well as other characteristics that can be gleaned from the voice signal, such as cough, sneeze, hoarseness or wheezing, for example, even if the person is not talking at the particular moment in which these occur.

The term "state" generally refers to one or more conditions and/or one or more characteristics that describe the user. The state is associated with the point in time at or time interval during which the associated sounds were obtained. State typically refers to a condition that may change over time for a given speaker. Examples of states may include emotional states (e.g., happy, sad, angry, surprised, fearful, emotional arousal, and emotional valence), cognitive or cognitive-affective states (e.g., confused, bored, confident, engaged, fluent, and committed/motivated), and both physical health and mental health states (e.g., depressed, stressed, PTSD, brain injury, Parkinson's disease, tired/sleepy, inebriated, illness (temporary or chronic), drug effects, hypoxia, low blood sugar, cough, sneeze, wheeze, etc.).

Features extracted from the audio signal, in addition to indicia of respiratory pathology, may include word-based (lexical), part-of-speech based, ASR-information-based (e.g., N-best, durations, confidences, lattice based, pronunciations, phones, or syllables), acoustic (e.g., cepstral, spectral, spectral-temporal, or noise-robust), articulatory (e.g., based on how human speech articulators move), phonetic (e.g., phonetic patterns of the signal and ASR output), auditory inspired (e.g., based on how the human auditory system processes speech), prosodic (e.g., intonation, timing, pausing, rate, loudness, voice quality patterns, and speech variability), speech/non-speech/voicing patterns, voicing percentage, intonation dynamics, turn-taking patterns, overlap patterns, discourse patterns (types of words used to manage interaction), pauses, filler words from ASR, or any combination thereof. Embodiments of the disclosed technology generally pertain to a computerized platform that can be used to extract and analyze various indicators of a speaker's state from a speech signal, even if the speech signal is captured with detracting environmental or channel characteristics (such as in a noisy environment, for example). Such embodiments may include a platform that is configurable to perform different types of speaker state analytics in real-time or "on demand," e.g., as needed in accordance with the requirements of a particular implementation of the system. For example, such a platform may determine which speaker state analytics are to be performed based on, e.g., the speaker's current context or in response to a detection of certain features in portions of the speech signal. Types of speaker state indicators that may be inferred from the speech analytics output by the disclosed system may include, for example, emotional, cognitive, and physiological state indicators, as well as any change in state indicators. That is, certain implementations may detect, based on features extracted from one or more speech signals, changes in the speaker's state, e.g., happy to nervous, motivated to confused, and mildly pleased to ecstatic.

Note that in case of severe respiratory disease, blood oxygenation may be low, and continued talking may further compromise oxygenation status. Therefore, even in absence of other indicia of respiratory disease, speech patterns associated with need to interrupt speaking to regain blood oxygen may also be detected.

Certain implementations of the disclosed technology may include systems configured to provide local and/or global data summaries and/or visualizations for both class output and feature outputs over time, typically as selected by the user. Such systems may also provide a template of algorithms (e.g., one or more algorithms) to run and "take notice" for thresholds on certain metrics after getting raw outputs from system. Summaries may then be made available in an interpretable manner to users. Thus, statistics and/or visualizations may be advantageously provided for any or all of the following: history and/or background data comparisons; archival and/or retrieval of output data; distilling of output (e.g., highlights of raw feature output); and interpretation and/or summaries of output data.

Implementations of the disclosed technology generally pertain to platforms, systems, and methods for speech-based speaker state analytics that may be implemented using one or more computing devices, e.g., in hardware, in firmware, in software, or in a combination of hardware, firmware, and/or software. In certain embodiments, the electronic device may also be configured (e.g., with additional microphones or multidirectional microphones or other sensors) to perform ambient sensing by retrieving or otherwise receiving other audio input (e.g. speech, sounds), and/or other data (e.g., other sensed data, metadata, etc.) that is detected in the user's surrounding physical and/or virtual environment 103. In such embodiments, the microphone(s) and/or other sensor(s) of the electronic device and/or the environment may advantageously pick up other audio inputs and/or other signals from the surrounding context, in addition to the speech and respiratory sounds input captured from the user (where the user may likely be physically located nearest to a microphone connected to the electronic device).

A sound analytics system may provide real-time state estimates and/or features, which may be fed back to the electronic device or to electronic device(s) of one or more end user(s) (e.g., model trainers, analysts), such that the electronic device and/or other electronic device(s) can then present the state information to the user, e.g., by way of an output device such as a display screen or touchscreen of the electronic device and/or other electronic device(s). In this way, the sound analytics system can be used to immediately or interactively inform the user of his or her own health status, or a health status of those nearby.

The sound analytics system includes a real-time feature extraction and classification subsystem, may explicitly include one or more model(s) (which may be trained by applying machine learning algorithms to a set of training data), and a model training subsystem (which may be remote from the user device, and precede deployment and use). The model(s) are accessed and used by the real-time feature extraction and classification subsystem to interpret the features extracted from the audio stream. Various different model(s) may be utilized by the analytics system for different applications, domains, or end users (human subjects), for example. The model training subsystem provides automated tools for generating the model(s). The real-time feature extraction and classification subsystem and the model training subsystem may be tightly coupled such that feature extraction, model adaptation, and classification of the sound input can occur asynchronously, e.g., continuously over the course of a session as the session progresses. For example, in some embodiments, the analytics system can dynamically vary the time interval ("time window") over which a sound sample is segmented.

In certain embodiments, the speech analytics system is implemented in an apparatus, which may include one or more computing devices, each of which include at least memory, e.g., non-transitory machine readable storage media (such as random access memory and/or read only memory), a processor (e.g., one or more microprocessors), at least one input device (such as a microphone), and at least one output device (such as a speaker and/or display). Such apparatus may include a signal preprocessing component, e.g., a subsystem or module, configured to enable real-time/interaction-time analytics such as speech signal segmentation, speech activity detection, etc. The apparatus may also include a library of analytics engines, where each analytics engine may be configured, e.g., executable by a processor, to provide as output a different type of state indicator.

Each analytics engine may include a component configured to perform selective feature extraction based on criteria such as the objective of the particular analytics engine, speech context, e.g., the user's current activity and/or information about the user's physical environment. Each analytics engine or the platform more generally may include a component configured to perform automated extraction of verbal word content and/or non-verbal acoustic features/indicators from a speech signal. The analytics engine or the platform more generally may utilize verbal content extracted from the speech signal (such as words or phrases), non-verbal acoustic features/indicators (such as prosodic features and/or others), gasps, stuttering, breath sounds, articulatory features (e.g., how the speaker's tongue moves during the speech), phonetic features, spectral features, or a combination of verbal features and non-verbal features, e.g., in the performance of a particular analytics task.

In certain embodiments, a method or process for development of a customized real-time/interaction-time state analytics module/system, e.g., in which the state analytics may be derived from an audio signal, can be implemented using one or more computing devices configured to selectively extract features based on one or more criteria, e.g., where the one or more criteria may be customized (such as for a particular application, context, or user); label features based on the selected criteria; using the labeled data, build a model to analyze one or more input signals for features/indicators relating to the selected criterion/criteria; configure an analytics engine based on the model; and instantiate the analytics engine in a state analytics module/system. The method may facilitate the creation, development, or automated generation of a custom/personalized analytics application or "app." In other cases, the implementation is self-adaptive, and therefore tunes itself to the respective user over time.

Implementations of the disclosed technology may be used in conjunction with speaker identification tools to diarize a multi-party recording and direct identified sounds to appropriate analytic engines, for example. In addition, such speaker identification technologies can provide detection of additional speaker data in non-labeled speech for building up additional background model information to improve model quality, for example. The detection—and, in some instances, analysis, of background speech, music, or other non-speaker audio can advantageously assist with the primary analysis.

Certain implementations of the disclosed technology make use of context meta-information for certain scenarios. Such meta-information is generally intended for use in data categorization, selection, and retraining. A live database may support the enrolling of new meta-data to support later data selection for a multitude of categories. Consider an example to support the tracking of the context of a person's respiratory sounds. Such meta-data tagging may support various analyses such as how the state changes when the user is talking vs. non-communicative breath sounds. Another type of meta-information may be geographical. As the meta-data becomes richer over time, the underlying data can be grouped in different ways, e.g., to support training and analysis that can extend beyond the initial scope.

While a preferred embodiment of the invention is embodied within a smartphone, alternately, it may be implemented within, or in conjunction with a smart speaker system with cognitive sound analysis and response. A characteristic of these known smart speaker devices is the preference and implementation for a fixed predefined wake word or phrase that the smart speaker must recognize in order to determine that it is to perform speech recognition on the spoken words of the user following the wake word or phrase. Examples of such fixed wake words or phrases include, for example, "Hey, Siri . . . " for the Apple Siri™ software devices, "Cortana . . . " for the Microsoft Cortana devices, or "Alexa . . . " for the Amazon Echo™ software devices. This preference arises from a need to limit interactions to intentional ones.

Known smart speakers are not configured to autonomously recognize different types of sounds as wake sounds and do not provide any functionality for analyzing various sounds to categorize them, determine patterns of sounds, cognitively analyze such patterns to identify events occurring within a monitored environment, and automatically cognitively determine appropriate feedback or response actions to be performed in response to identification of such events. See, U.S. 20200020329 and 20200020328.

The present invention provides a smart speaker system that is capable of analyzing a variable wake sound which activates the smart speaker system's functionality for cognitively, and automatically, analyzing the sound, identifying or classifying the sound as a particular type of sound originating from a particular type of sound source, analyzing the pattern of sounds occurring within a designated time window of each other to identify a potential event, and determining an appropriate responsive action to perform in response to the identification of the potential event. The analysis of the pattern of sounds may take into account a plurality of different information obtained from analysis of the sounds and patterns of sounds themselves, as well as other knowledge databases and information sources that may be generalized for any monitored environment, specific to the particular environment being monitored by the specific smart speaker device and system, or even specific to the particular user or operator of the smart speaker device.

Preferably, audio is maintained in a buffer or circular buffer which is subject to processing, to permit sounds preceding the wake sound to be fully analyzed.

For example, the smart speaker system may recognize any sound or type of distinct sound, which has a classifiable pattern, such as a cough, sneeze or wheeze.

These sounds may take many different forms depending on the particular implementation and may include, for example, sounds of a dog barking, loud noises, calls for help, fire alarms, carbon monoxide alarms, machine making an improper noise (e.g., due to a defect, incident, or worn part), the speaking of a code/token such as a prime number or emergency word/phrase (e.g., as a user security signal or the like), whistling, the sound of someone falling to the floor, pest noises (e.g., mice, bees) in a wall of the environment, a car accident, baby or child crying, glass breaking, doorbells, or any other distinguishable sound that may indicate something occurring within the monitored environment, that is of importance for performing a responsive action.

A registry or database of sound patterns, sound features, or the like, and their corresponding sound types and source types, also referred to herein as a sound sample archive, may be provided for use in classifying detected sounds into a corresponding type of sound from a particular type of sound source. In addition, a registry of sound patterns, which may include correlations of sounds, sequences of sounds, or other patterns of identified sounds indicative of events occurring within a monitored environment may also be provided for use in determining whether a corresponding event is or has occurred within the monitored environment. For example, a sneeze may be preceded by a strong inhalation (the "ah" phase of a sneeze, "ah-choo"), and a cough may be preceded by a wheeze or other indicium of a trigger.

The illustrative embodiments may comprise one or more microphones or other audio capture devices, either present in a single smart speaker device, multiple smart speaker devices, or other distributed array of audio capture devices, within or associated with a monitored environment. In some embodiments, the audio capture devices may be part of a smart speaker device that is mobile within a monitored environment, such as part of a robotic chassis whose movement is either automatically guided through the monitored environment or controlled remotely by a human operator. The audio capture devices operate to capture audio data, e.g., data representing the waveform of sound captured from a monitored environment. The audio data may then be locally and/or remotely stored and analyzed to identify the sounds and source of the sounds present in the audio data. For example, the analysis of the audio data may comprise first determining, such as at a local level, whether the captured audio data represents one or more sounds that may be significant for additional analysis, i.e. sounds that are distinct from learned ambient sounds of the monitored environment and which pass an initial set of criteria, which may be user configurable, indicating a need for further analysis.

Thereafter, a more cognitive and detailed analysis of audio data comprising sounds determined to be significant may be performed either locally or remotely, e.g., at a remote server or other computing device. For example, such analysis may comprise performing pattern analysis, feature extraction (e.g., amplitude, frequency, duration, etc.), comparisons to known sounds or sound patterns, and the like. More generally, optimized filters and source extraction may be implemented at a low level, within the smart speaker, rather than transmitting all sounds to a remote server, which has negative privacy implications.

The patterns and/or features may be used as a basis for comparing the audio data, i.e. the sound sample, with a stored archive of sound samples, i.e. a sound sample archive, to thereby indicate a nature or type of the sounds in the audio data and/or the nature or type of the sound sources generating the sounds in the audio data. Pattern analysis may be applied to compare the sound sample patterns to determine a degree of matching of the captured sound sample to archived sound samples. Similarly, feature comparisons may be used to determine a degree of matching between features of the captured sound samples with archived sound samples. In this way, the identification or classification of a captured sound sample may be generated with regard to archived sound samples that have a highest degree of matching or confidence in the matching.

In some implementations, the audio capture device(s) are able to triangulate or otherwise identify the location within the monitored environment from which the sound is sampled and may track movement of sound sources within the monitored environment, e.g., tracking amplitude and timing of received audio data from one or more audio capture devices indicating movement towards or away from the respective audio capture devices. Such location and/or movement information may be used to assist with cognitive analysis of the audio data to identify the classification or identification of the sound. Such location and/or movement detection may be based on sound amplitudes received at various audio capture devices positioned in different positions of the monitored environment, e.g., the same sound received at different audio capture devices with different amplitudes indicates the source being closer to audio capture devices where the amplitude is relatively greater and further away from audio capture devices with the amplitude is relatively lower.

This same technology may track two or more distinct persons within the soundscape, and determine their relative proximity to each other. Since the smart speaker typically include a Bluetooth transceiver, if one or both users have smartphones, the smart speaker may also include Bluetooth or WiFi proximity or localization technology to track user's positions and movements.

Various types of analysis may be performed on the captured audio data to perform sound identification in a composite sound signal. For example, impulsive sound components in a composite sound signal may be separated using wavelet analysis and sorting of wavelet coefficient sets according to statistical parameters of each respective coefficient set, such as is generally known in the art. Each entire coefficient set is either included or excluded from each respective separated component based on the statistical parameters. Once the impulsive sound component is isolated, it may be compared to reference sound information, e.g., stored or archived sound patterns, in order to classify the sound according to its potential causes.

In some embodiments, a history of captured audio data, and the sound identification results associated with the captured audio data, e.g., the identification of the type of sound and the type of sound source of the sound, may be stored for use in cognitively evaluating the pattern of different identified sounds to determine whether an event is occurring within the monitored environment that would trigger a responsive action, or reaction, by the smart speaker system, e.g., the outputting of an audible message, the outputting of an audible request or question to a user and listening, via the smart speaker device, for an audible response from a user which is then processed, the triggering of a display of information such as on a display associated with the smart speaker device, the triggering of a visual indicator on the smart speaker device, such as a light on the smart speaker device, the initiating of a communication (automated telephone call, electronic mail message, instant text message, or the like) to another device via a wired or wireless connection, or the like. The history may be stored in a local buffer memory of the smart speaker device, stored remotely in a remote storage device of a computing system in association with an identifier of the smart speaker device, or the like. The history preferably is configured to store captured audio data and the corresponding identification of sounds present in the audio data as determined from the smart speaker system, identified sound source types, and any other suitable features of the captured sounds, for a predetermined time window, or period of time, consistent with an amount of time required to identify events occurring within or in association with the monitored environment. For example, the time window may be set to store audio data captured over a 5, 10, or 15 minute time duration, or any other desirable amount of time, such that patterns and correlations of sounds present in the audio data captured during the time window may be made to identify events occurring within or associated with the monitored environment.

In the above example embodiment, the time window is relatively short and associated with a time period determined to be sufficient to identify events occurring within or associated with the monitored environment. However, in some illustrative embodiments, the history may be maintained in the smart speaker system in a more permanent fashion for use in later playback operations. For example, the buffered audio data and corresponding sound identifications may be moved from the buffer memory to a more permanent memory, e.g., a hard disk storage system, remote storage system, or the like, for later retrieval and playback when desired. Moreover, such a stored history may be made accessible to a user via another remotely located computing device, e.g., a user may be notified, via an electronic communication (e.g., email, instant message, or the like) of an event occurring and be given a link or other selectable mechanism by which to access the stored audio data and sound identification information from the permanent storage.

The cognitive analysis of the identified sound(s) in the captured audio data over the specified time window may involve utilizing stored or learned knowledge about events and the types of sounds associated with such events. This stored or learned knowledge may be provided in the form of machine executable rules that are stored in the smart speaker system, either in the local smart speaker device, in a remotely located computing system (e.g., a cloud computing system), or a combination of both local and remotely located devices/systems. The rules may be stored as template data structures, where each template data structure may represent a different type of event and may comprise one or more rules.

In determining whether an event is occurring within or in association with the monitored environment, a degree of matching of the sounds found in the captured audio data to the criteria specified in these rules/templates may be calculated to determine a risk or danger level of the perceived event associated with the monitored environment. For example, the risk or danger level may be a combination of a basic or default risk or danger level associated with the event defined by a rule/template, weighted by the degree of matching of the sounds, or patterns of sounds, identified in the captured audio for the specified time window.

For example, a template may have one or more rules specifying criteria for an event of a contagious risk at the monitored environment. The rules may specify the sounds as including cough, sneeze, gasp, etc. Based on how many of these sounds are identified in the captured audio data during the specified time window, a degree of lingering contagion risk in the environment may be calculated and used to weight the basic or default risk/danger level of the event, e.g., the default risk/danger level may be considered high, but if the number of matching sounds is low, then the risk/danger level may be reduced accordingly. Alternatively, the degree of matching may simply be used as a measure of confidence that the event is actually occurring or has occurred in association with the monitored environment and if the confidence is sufficiently high, e.g., equal to or greater than a predetermined threshold, which may be user configurable, then the event specified in the rules/template is considered to be a match and the corresponding risk/danger level for that event is utilized.

Based on the type of event, source of the sounds identified in the captured audio data, and the risk/danger level associated with the event, a corresponding responsive action may be taken by the smart speaker system. The responsive actions may take many different forms depending on the particular type of event. However, these responsive actions may generally be categorized into local audible/visual message/request output actions, remote communication actions, and local device control actions. Of course, a combination of such actions may also be utilized. Examples of local audible/visual message/request output actions include, but are not limited to, outputting a natural language message in an audible format indicating the nature of a detected event, outputting a natural language request in an audible format indicating a nature of the detected event and requesting instructions from a user (followed by appropriate action based on the user response), illuminating or otherwise controlling the turning on/off of a visual indicator as well as controlling characteristics of the visual indicator, e.g., color, textual message displayed, blinking, rate of blinking, or other visual characteristics, and the like. Examples of remote communication actions include, but are not limited to, initiating an automated telephone call to a user's registered telephone number, initiating an automated sanitization or cleaning operation, e.g., a Roomba™ robot style automated cleaning system, initiating a call to emergency services personnel, sending an electronic mail message to a user associated with the smart speaker system indicating the detected event with/without attachment of audio data for playback, sending an instant message or push notification to a registered device associated with a user, or the like. Examples of local device control actions include, but are not limited to, turning on/off ultraviolet lights (under safe conditions), activating/deactivating HVAC or air purification systems, turning on/off video feeds from security video cameras, etc. In some cases, the nature of the response may depend on whether face coverings are being employed. Therefore, a camera may be employed to visualize the persons in the environment, and in particular to detect facemasks or other suitable face covering to reduce contagion risk. Further, the sounds and/or video may be analyzed for speaker/user recognition. In some cases, a person may be immune to from the contagion risk, e.g., has already been infected, has been vaccinated, etc. In that case, the contagion risk may be deemed low, both for transmission and receipt of disease. This can help distinguish a cause of a respiratory sound. For example, an immune person may suffer seasonal allergies and have cough or sneeze as a result. The system, upon considering sounds indicative of cough or sneeze, may then consider the identity of the proximate persons, their medical history (including perhaps recent antibody or antigen tests), and contemporaneous weather and other respiratory ailment risks. This consideration may then be used to weigh the contagion risk for a particular disease.

The smart speaker may localize a sound, and control the viewing position of video cameras, e.g., by controlling a motor in the video camera to pan the camera to focus on a location where the smart speaker system determines the source of a detected sound may be present.

Thus, based on the type of event, source of the sounds identified in the captured audio data, and the risk/danger level associated with the event, one or more corresponding responsive actions are identified by a cognitive system of the smart speaker system and a runtime action composer component (which is typically remote from the smart speaker, through the Internet) composes the corresponding responsive actions and causes the responsive actions to be performed. This may involve accessing registered contact information for the user, such as may be stored in configuration information or a user profile data structure, to obtain information for sending communications and what those communications should contain. This may further involve accessing other knowledge bases located remotely to obtain information needed to formulate the content and/or control information for composing and/or directing the responsive actions, e.g., unique identifiers of devices to be controlled, and the like.

The operation of the smart speaker system is configurable in many different ways so that the types of events for which the smart speaker is to monitor the environment, the level of confidence and/or danger/risk level required for different types of responsive actions to be performed, the types of responsive actions to be performed in response to particular types of events, schedules of when certain types of events are to be monitored for, and the like. Moreover, the smart speaker system may learn, over time, normal ambient sound patterns for the monitored environment such that these normal ambient sound patterns may be filtered from other captured sound data when evaluating whether or not significant sounds are present in captured audio data requiring further analysis.

Thus, the present invention provides a cognitive smart speaker device and smart speaker system that continuously monitors the environment for sounds, and has action triggers upon detection of a distinct pattern, through cognitive analysis of patterns and features of the captured sounds, based on classification and discrimination algorithms.

Moreover, the mechanisms of the illustrative embodiments may utilize joint analysis when performing such cognitive analysis, using a plurality of different sound attributes and information obtained from other knowledge databases and information sources, to identify the type of sounds captured and the types of sources of such sounds. Furthermore, the mechanisms may evaluate patterns of identified sounds to identify events occurring within or associated with a monitored environment and may take appropriate responsive action in response to identifying an event.

The term "mechanism" refers to elements that perform various operations, functions, and the like. A "mechanism," may be an implementation of the functions or aspects of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms may be implemented as specialized hardware, software executing on general purpose hardware, software instructions stored on a medium such that the instructions are readily executable by specialized or general purpose hardware, a procedure or method for executing the functions, or a combination of any of the above.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A non-transitory computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. On the other hand, an automated processor may be controlled in dependence on transitory information.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Python C++ or the like, and conventional procedural programming languages, such as the "C" programming language or similar programming languages. The computer readable program instructions may execute entirely on the user's computer/smartphone/smart speaker, partly on the user's device, as a stand-alone software package, partly on the user's device and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions, and the block boundaries do not denote physical separateness or code module separation.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate aspects of the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). Note that unless antecedent processing is required, the order of blocks may be arbitrary. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides a smart speaker system that is capable of continuously analyzing sounds, and classifying the sounds to make decisions or produce data flows in response to the analyzed sounds. In one scenario, the presence of a sound activates the smart speaker system's functionality. The identifying or classifying of the sound as a particular type of sound originating from a particular type of sound source, analyzing the pattern of sounds to identify a potential event can all occur in real time, or be delayed.

The smart speaker system may be completely provided within a stand-alone smart speaker device or may be distributed over multiple devices that may communicate via one or more data networks. For example, a smart speaker device may be provided that includes software logic for implementing the various components of a smart speaker system in accordance with the illustrative embodiments. Such a stand-alone smart speaker system may access remotely located data processing systems for information retrieval purposes, but otherwise the functionality of the illustrative embodiments may be provided within the stand-alone smart speaker device. In other illustrative embodiments, the smart speaker system may comprise a smart speaker device that performs a first subset of the functionality described herein with regard to various ones of the illustrative embodiments, while other subsets of the functionality may be provided by one or more other data processing systems, cloud-based systems, or the like.

As discussed above, the phrase smart speaker may also encompass a smart phone configured to act in accordance with the functions of a smart speaker, and therefore, a smartphone with an "Alexa" or "Google" app running or accessible may be encompassed within the functions of a smart speaker. Note that smartphones are typically higher performance devices (other than audio quality) than smart speakers, and therefore substantially all smart speaker functionality may be subsumed within a smartphone.

The device may generate requests may be provided as structure or unstructured data, request messages, natural language questions, or any other suitable format for requesting an operation to be performed by the cognitive system. For example, the request may be simply the detection of audio data by audio capture device(s) associated with a smart speaker device and the request being the input data provided for sound pattern/feature analysis and recognition, event identification, and responsive action performance. In other cases, the request may be a spoken question made by a user and captured by an audio capture device of the smart speaker system.

The request processing pipeline may have an associated corpus or corpora that is ingested by the cognitive system to perform cognitive operations on input requests and/or data. The corpus or corpora may comprise information from a variety of different sources which may be generalized for a plurality of different types of monitored environments, or may be specific to the particular monitored environment in which the smart speaker system is present, or specific to the particular user associated with the smart speaker system. For example, the corpus may comprise general sound pattern, sound features, and corresponding sound types and types of sound sources for various types of general sounds that may be found in a number of different environments, e.g., sounds of a dog barking, human coughs, calls for help, fire alarms, carbon monoxide alarms, machines making improper noises (e.g., due to a defect, incident, or worn part), the sound of someone falling to the floor, pest noises (e.g., mice, bees) in a wall of the environment, a car collision, baby or child crying, glass breaking, doorbells, or any other distinguishable sound that may indicate something occurring within the monitored environment, other than a normal ambient sound situation, that is of importance for performing a responsive actions. In some cases, it is efficient to identify potentially interfering sounds than to fully differentiate desired sounds, while the former strategy permits other uses for the same hardware investment.

The corpus may comprise configuration information for the particular monitored environment in which the smart speaker system or device is present. For example, the corpus may comprise configuration information indicating the type of the monitored environment, e.g., a home residence, office, school, commercial property, etc. which indicates a potential subset of audio samples that may be associated with that monitored environment. The configuration information may comprise a listing of the contents of the monitored environment, e.g., a television, refrigerator, dishwasher, vacuum cleaner, computer, stereo, telephone, washing machine and dryer, glass windows, doors, security alarms, fire alarms, carbon monoxide sensors, etc. In some cases, information about the user and/or other occupants of the monitored environment may also be registered in the configuration information including gender, age, and the like. Any configuration information that may be used to select subsets of audio sample information from the larger superset of generalized audio samples may be included without departing from the spirit and scope of the present invention. This allows for a multi-tiered matching or evaluation of captured audio samples by first looking to the subsets for matches and if no match is found then expanding the search to the larger superset of generalized audio samples, e.g., if the smart speaker system knows that an elderly person lives in the monitored environment, a subset of audio samples associated with elderly persons may be first searched to determine if there is a sufficient match and if not, then a search of a larger superset of generalized audio samples may be performed.

The corpus may also comprise specific sound patterns for the specific monitored environment. For example, during a training phase of operation, the audio capture devices of the smart speaker system may be used to capture audio samples over a training period of time from the specific monitored environment. These captured audio samples may be analyzed to extract audio features of the captured audio samples and may be presented to the user of the smart speaker system for classification, such as by recording the captured audio samples and replaying them to the user who may then answer questions that the smart speaker system presents to the user and captures the user's response via natural language processing.

For example, during a training period, the audio capture devices may capture the sound of an icemaker in a freezer dropping ice into the receptacle. The audio capture device may capture the audio sample and analyze it to extract representative audio features. The audio sample may be stored for later playback to the user when the user agrees to assist with training. The smart speaker system, via the smart speaker device, may playback the audio sample followed by a set of inquiries, such as "What is this sound?", "What is the source of this sound?", or the like. In response to each of these inquiries, the audio capture device of the smart speaker device may capture the user's spoken response and may then perform natural language processing of the spoken response to obtain the identification of the type of sound, i.e. ice dropping, and the type of sound source, i.e. freezer ice maker. This information may be stored, along with the extracted features and even the captured audio sample, in a monitored environment specific database or registry of sound samples specific to the monitored environment.

Similarly, the corpus or corpora may comprise personal information, audio sample information, and the like, that is specific to the particular user associated with the smart speaker system. For example, the audio capture device of the smart speaker system may capture and store an audio sample of the user's speaking of a personal identifier. The personal information provided in the corpus or corpora may also comprise information from other systems that the user may utilize, such as a computerized personal calendar, electronic mail system, communication device contact information database, or the like. The information provided from these various systems may be utilized to perform cognitive analysis of captured audio samples to determine whether events are occurring or have occurred, the risk or danger level of the events, and perform responsive actions if needed.

The smart speaker system, or the corpus/corpora, may further include knowledge, rules, or the like, defining events and responsive actions that the smart speaker system is to perform in response to such events. The knowledge or rules may specify sounds that occur relative to one another and which combined represent an event. The sounds may be defined as occurring in a sequence or a sequence may not be specified. That is, the event may be determined to have occurred or be occurring within or associated with the monitored environment only if a sufficient number of the sounds are detected in the captured audio samples for a particular period of time, and a specified sequence of sounds is determined to be present, or regardless of the sequence. Responsive actions may be dependent on the particular event and risk/danger level of the event. For example, if the event is a break-in event indicating an intruder has entered the monitored environment, the risk/danger level is considered high and the responsive action may be to initiate an automated call to the police or an emergency first responder communication system, e.g., 911 call. If the event is a series of coughs coming from a baby, the event may be considered to be potential croup and the user may be informed of this potential situation, such as via an audible message, an email or other textual message with an attachment of the stored audio sample, or the like, so that the user may perform a follow-up on the event detected by the smart speaker system. Moreover, such sounds of coughing or the like may be recorded, transmitted, and played back to a medical professional, e.g., physician, ER doctor, etc., for assisting the medical professional in treating the patient. Various types of responsive actions may be defined for implementation by the smart speaker system based on the particular corresponding event and may be stored in association with such knowledge or rules either in the smart speaker system itself, or in the corpus/corpora accessed by the smart speaker system.

Note that in contradistinction to 20200020329 and 20200020328, the audio environment is continuously monitored for sounds representing respiratory noises, which may include speech, but also breath sounds, cough, sneeze, wheeze, snort, and other sounds. Detection of these sounds do not necessarily trigger an awakening of the device, or some particular active response. The sounds and their pattern are analyzed detections recorded. However, within the same framework, a more traditional smart speaker implementation may be achieved employing the same hardware components and in some cases, sound processing primitives. Further, at a higher level, a cognitive analysis of speech patterns may help differentiate speech sounds that are similar to pathological respiratory noises.

A cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like. In the context of the illustrative embodiments set forth herein, the logic of the cognitive system implements cognitive operations for autonomously recognizing different types of sounds as wake sounds, analyzing various sounds to categorize them, determine patterns of sounds, cognitively analyze such patterns to identify events occurring within a monitored environment, and automatically cognitively determine appropriate feedback or responsive actions to be performed in response to identification of such events.

Note that the real-time continuous analysis of respiratory sounds need not be cognitive, and rather may be primitive or not commensurate with human thought processes. For example, the sound processing may employ domain transforms that are foreign to intrinsic human cognition, such as wavelet transforms, and may perform operations distinct from cognitive operations. On the other hand, as appropriate, the IBM Watson™ computer software system may be employed for cognitive analysis of information transmitted outside of the smartphone or smart speaker.

Natural language processing of spoken words may be performed by converting the spoken words represented in the captured audio data to a textual representation and performing natural language processing of the textual representation. The natural language processing may operate to attempt to determine what is being said to determine how to respond to the spoken words. Such natural language processing is generally known in the art.

In some embodiments, the analysis of the captured audio sample may utilize both natural language processing and audio characteristic analysis to perform sentiment analysis or other non-semantic analysis.

The information stored in the input buffer or temporary storage may be used by the event identification engine as a basis for determining whether an event has occurred within or in association with the monitored environment. This may be done on a continuous basis as audio information is added to the buffer or temporary storage, such as in the case of a moving time window, or may be done on a periodic basis, such as at the elapse of each period of time for which the buffer or temporary storage is used to store captured audio sample and sound identification information (collectively referred to as sound information).

Evaluation of the input stream by an event identification engine may involve applying event models from a sound and event model repository to the stored sound information in the buffer or temporary storage to determine if criteria of the event model are satisfied to a threshold level of certainty to indicate that the corresponding event has occurred. That is, the analysis of the identified sound(s) in the captured audio samples over the specified time window may involve utilizing stored or learned knowledge about events and the types of sounds associated with such events which are represented as event models in the sound and event model repository. This stored or learned knowledge may be provided in the event models as machine executable rules stored in the sound and event model repository of the smart speaker system, in the local smart speaker device itself, or a combination. The machine executable rules may be stored as template data structures, where each template data structure may represent a different type of event and may comprise one or more rules for matching as well as additional information for evaluating the event when it is matched, e.g., a default risk or danger level, an identification of a responsive action to take, etc.

The stored and learned knowledge represented in the rules or templates of the event models may specify one or more sounds indicative of an event. The event model may further specify timing constraints, sequences, particular combinations of sounds, particular locations of sounds, or the like, that are indicative of the event. The sound information stored in the buffer or temporary storage may be compared to such criteria and a degree of matching of the sound information stored in the buffer or temporary storage to the event model may be determined and this degree of matching may be compared to a predetermined threshold requirement for determining that the event model has been matched. If the event model has been matched, then the event is determined to have occurred in association with the monitored environment.

In determining whether an event is occurring within or in association with the monitored environment, the degree of matching of the sounds found in the captured audio samples to the criteria specified in these rules/templates may be calculated to determine a risk or danger level of the perceived event associated with the monitored environment. For example, the risk or danger level may be a combination of a basic or default risk or danger level associated with the event defined by the rule/template, weighted by the degree of matching of the sounds, or patterns of sounds, identified in the captured audio for the specified time window. Based on how many of these sounds are identified in the captured audio data during the specified time window, a degree of matching may be calculated and used to weight the basic or default risk/danger level of the event, e.g., the default risk/danger level may be considered high, but if the number of matching sounds is low, then the risk/danger level may be reduced accordingly. Alternatively, the degree of matching may simply be used as a measure of confidence that the event is actually occurring or has occurred in association with the monitored environment and if the confidence is sufficiently high, e.g., equal to or greater than a predetermined threshold, which may be user configurable, then the event specified in the rules/template is considered to be a match and the corresponding risk/danger level for that event is utilized.

Assuming an event model is matched by the sound information stored in the buffer or temporary storage, a responsive action performance engine may evaluate the event to determine an appropriate responsive action to be performed, if any, and may initiate performance of that responsive action. The particular responsive action may be dependent upon the type of the matching event and its determined danger or risk level, as well as any specific responsive actions that may be specified in the matched event model, if any. The determined danger or risk level may be determined by the responsive action performance engine based on the danger/risk level associated with the identified event, such as by using a specified default danger/risk level, possibly weighting the default danger/risk level by a degree of matching with the event model criteria, as described above, and evaluation of other relevant factors including time of day (break-ins at night or when residents tend to be home are relatively higher danger/risk level than other times of the day), user preferences or configuration information for such events indicating user determined danger or risk levels for the particular event (e.g., one user may desire to rank dog barking sounds as relatively higher danger/risk level than another user), and other information present in the configuration information and from other knowledge bases. The danger or risk level along with the event type may be correlated with a responsive action which is then initiated. This responsive action may be a responsive action specifically associated with the event in the event model itself, may be a responsive action performed in addition to any specific responsive action indicated in the event model, or may be a selection of one of a plurality of possible responsive actions set forth in the event mode based on the determined level of danger or risk associated with the event.

The responsive actions may take many different forms depending on the particular type of event. However, these responsive actions may generally be categorized into local audible/visual message/request output actions, remote communication actions, and local device control actions. Of course, a combination of such actions may also be utilized. These responsive actions may make use of the audio output device(s) of the smart speaker device, may make use of control capabilities of the smart speaker device to control other devices within or associated with the monitored environment, such as via a wireless network and home automation products, e.g., cleaning/sanitizing devices, HVAC/air purifiers, social distancing violation alerts, and the like.

Examples of local audible/visual message/request output actions include, but are not limited to, outputting a natural language message in an audible format indicating the nature of a detected event, outputting a natural language request in an audible format indicating a nature of the detected event and requesting instructions from a user (followed by appropriate action based on the user response), illuminating or otherwise controlling the turning on/off of a visual indicator as well as controlling characteristics of the visual indicator, e.g., color, textual message displayed, blinking, rate of blinking, or other visual characteristics, and the like. Examples of remote communication actions include, but are not limited to, initiating an automated telephone call to a user's registered telephone number, initiating a call to a security company managing the security of the monitored environment, initiating a call to emergency services personnel, sending an electronic mail message to a user associated with the smart speaker system indicating the detected event with/without attachment of audio data for playback, sending an instant message to a registered device associated with a user, or the like. Examples of local device control actions include, but are not limited to, turning on/off lights, activating/deactivating security alarms, locking/unlocking doors, turning on/off video feeds from security video cameras, controlling the viewing position of such security video cameras, e.g., by controlling a motor in the video camera to pan the camera to focus on a location where the smart speaker system determines the source of a detected sound may be present, playing music or other audio, or the like.

The responsive action performance engine of the smart speaker system composes the corresponding responsive actions and causes the responsive actions to be performed via the smart speaker device. This may involve accessing registered contact information for the user, such as may be stored in configuration information or a user profile data structure of the configuration information and knowledge base interface, to obtain information for sending communications and what those communications should contain. This may further involve accessing other knowledge bases, via the configuration information and knowledge base interface, located remotely to obtain information needed to formulate the content and/or control information for composing and/or directing the responsive actions, e.g., unique identifiers of devices to be controlled, identifiers of on-line retailers from which products/services may be obtained, contact information for first responders or emergency services in the geographic area of the monitored environment, and the like.

Thus, based on the type of event, source of the sounds identified in the captured audio data, and the risk/danger level associated with the event, one or more corresponding responsive actions are identified by the smart speaker system implemented in, or in association with, the cognitive system. The logic of the smart speaker system may interact with or be integrated with various stages of the pipeline of the cognitive system to achieve this functionality. For example, the audio sample analysis and classification engine may operate in conjunction with, or even may be implemented as, the pipeline in cognitive system as the functionality of the engine involves an input parsing, analysis, and decomposition stage of the pipeline as well as hypothesis generation, evidence scoring, synthesis, and final result generation to identify sounds in a received audio sample from the smart speaker device. Similarly, the event identification engine may be integrated in, or work in conjunction with, one or more stages of the pipeline to identify events as described above. In some embodiments, the event identification engine may also be implemented as a pipeline entirely and this pipeline may be separate from that of a pipeline used to identify individual sounds in an audio sample, e.g., a first pipeline for identifying sounds in a captured audio sample and a second pipeline for identifying events based on the sounds in captured audio samples and stored in the buffer or temporary storage.

In the above example embodiment, the time window for which sound information is stored in the buffer or temporary storage is described as a relatively short time window and associated with a time period determined to be sufficient to identify events occurring within or associated with the monitored environment. However, in some illustrative embodiments, the history of captured sounds may be maintained in the smart speaker system in a more permanent fashion for use in later playback operations, such as in a history data structure associated with the particular monitored environment or smart speaker device. For example, the buffered audio data and corresponding sound identifications may be moved from the buffer memory or temporary storage to a more permanent memory, e.g., a hard disk storage system, remote storage system, or the like, for later retrieval and playback when desired. Moreover, such a stored historical playback may be made accessible to a user via another remotely located computing device, e.g., a user may be notified, via an electronic communication (e.g., email, instant message, or the like) sent to their computing device, mobile computing device, or the like, of an event occurring and be given a link or other selectable mechanism by which to access the stored audio data and sound identification information from the permanent storage of the smart speaker system.

It should be appreciated that in some illustrative embodiments, the sound and event model repository may store models applicable to multiple different smart speaker devices in multiple different monitored environments. Moreover, the sound and event model repository may learn and store models obtained from a variety of different monitored environments. For example, based on user feedback indicating the type and/or source of a sound, the user specified classification of the sound and sound source may be stored in association with the captured audio data in the repository to thereby dynamically modify and improve the repository by including additional models indicative of a particular type of sound or sound source. A similar operation can be performed for event models as well. Furthermore, such operations may be performed automatically by the system in response to a smart speaker device capturing audio data determined to be abnormal to assist in detecting normal versus abnormal sounds in other monitored environments. Thus, a collective learning of types of sounds and types of sound sources, as well as events, may be achieved using a plurality of different smart speaker devices in a plurality of different monitored environments.

It should be noted that as envisioned, a smart speaker need not have substantial speaker functionality, and may be more properly considered a smart microphone. Such device may be placed/disbursed in commercial and institutional environments, to provide real-time monitoring of spaces, i.e., "bugs". In order to provide privacy and information security, the audio analysis may be limited to local analysis of sounds (within the smart microphone or institution), and without any residual recording of the sounds. This may be achieved by programming the smart microphone to retain the raw audio data solely within a local non-persistent memory, and to define a communication protocol that does not permit streaming or transmission of buffer contents. For example, the communication protocol may limit the communications to a single IP packet per second or per few seconds, and the processing capability beneath that required to perform even primitive speech analysis, e.g., phoneme extraction.

On the other hand, in some cases, user may reduce their expectations of privacy, and accept remote sound processing that may include private information.

The operation of the smart speaker system and the smart speaker device is user configurable in many different ways so that the user can identify the types of events for which the smart speaker is to monitor the environment, the level of confidence and/or danger/risk level required for different types of responsive actions to be performed, the types of responsive actions to be performed in response to particular types of events, schedules of when certain types of events are to be monitored for, schedules of when the smart speaker system is to disable monitoring, such as for privacy or security reasons, and the like. For example, a user may make use of the computing device, a mobile computing device, or any other data processing device or system to access the smart speaker system and configure the user configurable parameters and provide configuration for storage in the configuration information and knowledge base interface. The user may make use of an application running on such a data processing device/system to access the smart speaker system and configure it for use with the user's own smart speaker device and for the monitored environment.

While the above illustrative embodiments assume that audio samples captured by the smart speaker device are those that are within the human perceivable range of sound frequencies, the present invention is not limited to such. Rather, in some illustrative embodiments, the smart speaker device may be sensitive to sounds beyond the normal hearing range (e.g., less than 20 Hz or more than 20 kHz). As such, the smart speaker system may be configured to analyze, identify, and classify such sounds and perform event identification and responsive action determinations in a manner similar to that described above, but with sounds outside normal human hearing range. The smart speaker device, as part of a responsive action, may also be configured to emit such sounds outside the normal human hearing range.

In some illustrative embodiments, the smart speaker system may selectively record anomalous sounds/noise, or noises that it has been programmed to record, and may perform responsive actions to try to mitigate such noises. The smart speaker system also may replay the noises (stored audio samples) and describe the context related to the noises and the action(s) that the smart speaker system took in the determined order or sequence.

The mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. For example, the technology improves the smartphone or smart speaker by providing continuous audio analysis and sound classification, using low power and low computational complexity, and permitting preservation of privacy by avoiding remote communication of the audio stream.

The audio sample may be analyzed using an initial set of analysis algorithms to determine if the sample is potentially a sound type needing further detailed analysis. For example, this operation may perform an initial determination as to whether the audio sample is of a sound that is a cough, but not who has coughed (or if it is generated by an audio reproduction device such as a TV or radio). This may be accomplished by performing analysis of the audio sample to extract major features and compare them to sound models of ambient sounds. A determination, based on such analysis and comparison to ambient sound models, is then made as to whether the audio sample contains a trigger sound requiring further detailed analysis. If the sound in the audio sample is not a trigger sound, then no further processing is necessary, and the operation terminates. Otherwise the successive stages or processing are initiated.

Configuration information and other knowledge base information that may be used to identify events and weight the confidence scores associated with events occurring in the monitored environment may also be retrieved from corresponding stores. A weighted confidence score may be generated based on the degree of matching of the various factors of the sounds, configuration information, and knowledge base information. A ranked listing of the matched event models is generated, and the confidence scores are compared to threshold requirements. A highest-ranking event model with the threshold amount of confidence score is selected as a match. The matching event model may specify a default danger/risk level for the event and a suggested responsive action to be performed.

According to US 2014663537, a cough model used to reconstruct coughs from extracted features may be sufficient to reconstruct the extracted cough features but may be insufficient to reconstruct other audio sounds, e.g., speech, that may also have been recorded by the microphone. Examples of cough models include principal component analysis representations of a cough. The principal components may be used to extract features from an audio signal and then again to reconstruct the audio signal. An audio signal (e.g., audio stream) may be received and represented as an audio spectrogram. The spectrogram may generally be a data representation of the audio including a measure of how the spectral density of the audio signal varies with time. For example, the audio spectrogram may include amplitude of sound at particular frequencies over time. The cough model may be a data model including a plurality of eigenvectors of a spectrogram (e.g., the principal components of a portion of a cough spectrogram). Accordingly, the cough model may include a representation of audio spectrograms indicative of a known cough. The cough model may include any number of basis vectors (e.g., eigenvectors), 10 eigenvectors in one example, and any number of eigenvectors in other examples including 5-25 eigenvectors. The cough model may be generated by analysis of known cough sounds, such as by portions of audio spectrograms manually identified by listeners as cough sounds. The cough model may be represented as a matrix $X_N$ where N denotes the number of components in the model. Eigenvectors may be selected through this analysis which reliably describe cough sounds as distinguished from non-cough sounds. The eigenvectors may be eigenvectors of a covariance matrix of frequency-based matrix representations of audio signals corresponding to known cough sounds. Accordingly, multiple frequency-based matrix representations (e.g., spectrograms) of audio signals corresponding to known cough sounds may be provided, and a covariance matrix of those representations may be provided. Eigenvectors of that covariance matrix may be used as the basis vectors for a cough model. Moreover, in some examples, the cough model may be based on only portions of known cough sounds. In some examples, the fidelity of the reconstructed cough sound may be increased by using a larger number of components (for example larger than 10) at the expense of making speech more intelligible during reconstruction, which is a tradeoff to be evaluated as may be desired.

Irritation of afferent cough receptors in airways may trigger a cough reflex. Once triggered, the cough reflex may include four phases: (1) an initial deep inspiration and glottal closure, (2) contraction of the expiratory muscles against the closed glottis, (3) a sudden glottis opening with an explosive expiration, (4) a wheeze or "voiced" sound. The third and fourth phases of the cough reflex may generally be manifested as a cough sound. Cough sounds may share common attributes such as a relatively loud intensity, quick burst of sounds, and predictable duration and falloff. The overall energy of a cough reflex may be much stronger relative to the surrounding environment and the initial burst of air may cause significant energy, for example well into the 15 kHz range. During the fourth stage of the cough reflex, remaining air from the initial impulse may be pushed out of a vocal tract. It is this fourth stage of the cough which may cause coughs to sound different amongst different individuals as the pathological processes in the lungs may determine the characteristics of the sound based on how the lung tissue and vocal resonances are affected. Accordingly, this fourth stage of a cough may vary from person to person and may not be useful in cough detection across a larger population.

Cough models used herein are based only on portions of coughs which are non-specific to users, e.g., the third or explosive stage of a cough. Stages of a cough which may be more likely to be user-specific (e.g. the fourth stage of a cough) may not be used to develop a cough model in examples of the present invention. Accordingly, cough models may be developed without using the fourth stage of known coughs (e.g., using only the explosive stage of known coughs). The audio signal (e.g., the frequency-based representation of the audio signal from box 220) may be compared with a cough model in box 230. The comparison may reduce the dimensionality of the frequency-based representation of the audio signal, resulting in a lesser dimensional matrix. The comparison may occur in accordance with principal component analysis, which generally uses orthogonal components (e.g., projections of eigenvectors) of a particular feature space to reduce dimensionality. The frequency-based representation may be multiplied by a matrix vectors from a cough model, resulting in a representation of projections of the cough model vectors into the frequency-based representation of the audio signal, a generally lesser dimensional matrix. A selected number of projections may be selected for use in the lesser dimensional matrix, and remaining projections discarded (e.g., the projections may be sorted by eigenvalue and the largest eigenvalue projections retained). The lesser-dimensional matrix may in one example include 10 projections, although in other examples any number of projections may be used including 5-25 projections. The number of projections in the lesser-dimensional matrix of the audio signal may be selected to match a number of eigenvectors used in a cough model. The frequency-based representation of the audio signal or portion of audio signal may be compared with the cough model including principal components indicative of coughs. The lesser-dimensional matrix may include a score for each of the principal components of the audio signal or portion thereof based on the vectors of the cough model. A plurality of scores (e.g. one score per eigenvalue) may be obtained in box 230 for use in determining whether or not the audio signal or portion thereof corresponds with a cough. The scores may represent entries in the lesser dimensional matrix which, as described above, may be generated by multiplying vectors from a cough model with the frequency-based matrix representation of the audio signal. The lesser dimensional matrix may also accordingly be referred to as a matrix of projection scores, where the lesser dimensional matrix includes scores representing a projection of the basis vectors of the cough model into the audio spectrogram.

Once a comparison has been performed with the cough model, one or more tiers of classification may be used to determine whether the audio signal or portion thereof corresponds with a cough sound. An initial or threshold analysis may be performed to filter out any features which fall below a predetermined threshold. For example, all of the scores obtained during the comparison may be required to be at or above a threshold to indicate a cough sound. In other examples, a certain number of scores (e.g., corresponding to a certain number of eigenvalues) may be required to be above the threshold for the audio signal or portion thereof to be considered a cough sound. In some examples, higher fidelity classification techniques may be used. For example, tree classifiers, such as but not limited to a random forest classifier, may be used to classify a portion of the audio signal as a cough sound. The random forest classification may allow for increased accuracy and/or lower false positive as to which of the extracted features from the audio correspond to cough sounds. The thresholds and/or configuration information for the tree classifiers may be additionally included in cough models described herein, such as the cough model, or may be stored as separate cough models or cough model information.

Extracted features which are classified as a cough (e.g., determined to correspond to a cough sound) may be stored. The extracted features may correspond to a representation of the audio signal or portion thereof identified as corresponding to a cough sound. The cough model may be based on only certain portions, e.g., initial portions, of a cough sound. Accordingly, in some examples, the extracted features may correspond to the representation of the portion of audio signal corresponding to the cough sound as detected using the cough model plus an additional amount of the audio signal (e.g., 1-5 additional seconds of audio signal). In some examples, additionally or instead, representations of portions of the audio signal preceding the detected cough may be stored (e.g., 1-5 additional seconds of audio signal). The additional amount of audio signal may facilitate later reconstruction of the entire cough sound. The extracted features may be stored locally on the same device which receives the audio or they may be transmitted to a remote location (e.g., database). Other parameters, for example time of the cough, may also be recorded and used in further analysis, for example in determining duration, frequency, quality of cough, number of coughs, cough epochs, and the like. In this manner, the computing system may further be configured (e.g., by being programmed with further executable instructions) to provide data (e.g., store data and provide the data to the computing device or other remote device) regarding cough frequency, quality, length, number of coughs, cough epochs, and the like over time. Moreover, the computing system may be configured to provide (e.g., display) data regarding the frequency, quality, length, number of coughs, and/or cough epochs (e.g., multiple coughs within a certain time combined to form one coughing episode).

The extracted features may be the mean decibel energy of a Fast Fourier Transform (FFT) of all or a portion of the audio signal, the mean decibel energy of the FFT coefficients above 16 kHz (or other threshold in other examples), and below 16 kHz (or other threshold in some examples). The energy values, components weights, and residual error between a reconstructed cough sound and actual cough portion of the audio signal may be referred to as the extracted features.

In this manner, portable devices such as cell phones and/or audio recorders may be used to continuously record sounds in the vicinity of a user. Sounds may include ambient noises, speech, coughs, sneezes, and other environmental noises occurring in the vicinity of the user. Events may be extracted from the audio recordings, either by the same device as performed by the recording or by a different device. The events may be extracted and then determined whether or not they correspond with cough sounds using PCA and a known cough model. The cough model may be stored on a device performing the analysis and/or may be downloaded from or accessed from another remote device. Features relating to cough sounds may be stored, and may be provided to the same or another device for reconstruction.

It is therefore an object to provide a method of monitoring respiratory sounds of a user, comprising: receiving an audio stream through a microphone; automatically identifying a commencement and a completion of a sound event cycle in the received audio stream with at least one automated processor; automatically distinguishing a respiratory event from a non-respiratory event in the sound event comprising performing a first analysis of frequency domain characteristics of the sound event with the at least one automated processor; automatically classifying a type of respiratory event of the user from a predetermined set of classifications comprising performing a third analysis of frequency domain characteristics of the sound event with the at least one automated processor; and at least one of outputting and storing the automatically classified type of respiratory event of the user. The method may further comprise automatically distinguishing between a respiratory event of a user of the device and a respiratory event of a non-user of the device comprising performing a second analysis of characteristics of the sound event with the at least one automated processor.

The respiratory event may comprise a cough, and the classified type of respiratory event may comprise a distinction between a cough of a COVID-19 person and a cough of a COVID-19 negative person.

It is also an object provide a method of monitoring respiratory sounds of a user, comprising: receiving an audio stream through a microphone of a device; identifying a commencement and a completion of a sound event cycle in the received audio stream; distinguishing a respiratory event from a non-respiratory event in the sound event comprising performing a first analysis of frequency domain characteristics of the sound event; distinguishing between a respiratory event of a user of the device and a respiratory event of a non-user of the device comprising performing a second analysis of characteristics of the sound event; and classifying a type of respiratory event of the user from a predetermined set of classifications comprising performing a third analysis of frequency domain characteristics of the sound event.

The respiratory event may comprise a cough, and the classified type of respiratory event comprises wet cough and dry cough.

The method may further comprise determining a location of the device during the respiratory event.

The classifying may be contingent upon determination of the commencement of the sound event cycle.

The device may be a smartphone having an operating system, having background execution and foreground execution, wherein at least the identifying and distinguishing a respiratory event from a non-respiratory event, are performed as background execution.

The device may be a smartphone having an operating system, having root execution privileges and user execution privileges, wherein at least the identifying and distinguishing a respiratory event from a non-respiratory event, are performed with root execution privileges.

The identifying may be performed using a sound event detection model comprising: performing a spectrographic analysis on received sound signals to produce a spectrogram; analyzing the spectrogram with respect to a spectrum model; and applying a frame-wise mask to the analyzed spectrogram.

The classifying may be performed using a sound source separation model, comprising: performing a spectrographic transform; segmenting the spectrographic transform; comparing the segmented spectrographic transform with a cough sound spectrum and a non-cough sound spectrum; and inverse transforming the segmented spectrographic transform corresponding to the cough sound spectrum.

The distinguishing between the respiratory event of the user of the device and the respiratory event of a non-user of the device may be performed using a non-speech source identification model, comprising: performing a spectrographic transform; employing a spectrum model; generating an embedded vector output; and performing a database lookup.

The classifying may distinguish between cough, sneeze, and clear throat sounds.

It is also an object to provide a non-transitory computer readable medium for controlling a programmable processor to perform a method of monitoring respiratory sounds of a user, comprising: instructions for receiving an audio stream through a microphone of a device; instructions for identifying a commencement and a completion of a sound event cycle in the received audio stream; instructions for distinguishing a respiratory event from a non-respiratory event in the sound event comprising performing a first analysis of frequency domain characteristics of the sound event; and instructions for classifying a type of respiratory event of the user from a predetermined set of classifications comprising performing a second analysis of frequency domain characteristics of the sound event.

The programmable processor is provided within a smartphone or smart speaker, or other fixed or mobile sensor or sensor network.

Instructions may be provided for distinguishing between a respiratory event of a user of the device and a respiratory event of a non-user of the device comprising performing a third analysis of characteristics of the sound event.

The respiratory event may comprise a cough, and the classified type of respiratory event may comprise wet cough and dry cough.

Instructions may be provided for determining a location of the device during the respiratory event.

The instructions for classifying may be executed contingent upon a determination of the commencement of the sound event cycle.

The device may have an operating system, having background execution and foreground execution, wherein at least the instructions for identifying and instructions for distinguishing a respiratory event from a non-respiratory event, are performed as background execution of the operating system. The operating system may have root execution privileges and user execution privileges, wherein at least the instructions for identifying and instructions for distinguishing a respiratory event from a non-respiratory event, are performed with the root execution privileges of the operating system.

The instructions for identifying may be performed using a sound event detection model, and further comprise: instructions for performing a spectrographic analysis on received sound signals to produce a spectrogram; instructions for analyzing the spectrogram with respect to a spectrum model; and instructions for applying a frame-wise mask to the analyzed spectrogram.

The instructions for classifying may be performed using a sound source separation model, comprising: instructions for performing a spectrographic transform; instructions for segmenting the spectrographic transform; instructions for comparing the segmented spectrographic transform with a cough sound spectrum and a non-cough sound spectrum; and instructions for inverse transforming the segmented spectrographic transform corresponding to the cough sound spectrum.

Instructions may be provided for distinguishing between the respiratory event of the user of the device and the respiratory event of a non-user of the device, performed using a non-speech source identification model, comprising: instructions for performing a spectrographic transform; instructions for employing a spectrum model; instructions for generating an embedded vector output; and instructions for performing a database lookup.

The instructions for classifying may comprise instructions for distinguishing between cough, sneeze, and clear throat sounds.

It is another object to provide a device for monitoring respiratory sounds of a user, comprising: a microphone configured to transduce acoustic waves into an electronic stream of audio information; at least one automated processor, configured to: identify a commencement and a completion of a sound event cycle in the electronic stream of audio information; distinguish between a respiratory event from a non-respiratory event in the sound event comprising performing a first analysis of frequency domain characteristics of the sound event; and classify a type of respiratory event of the user from a predetermined set of classifications comprising performing a second analysis of frequency domain characteristics of the sound event. The respiratory event may comprise a cough, and the classified type of respiratory event comprises wet cough and dry cough.

The device may further comprise a geolocation system for determining a location of the device.

The device may further comprise a radio frequency transceiver, e.g., a digital packet data network radio communication device or other data communication device, configured to communicate with a remote device, server and/or database. The communication may be a handshake, e.g., identifying a media access control (MAC) address, an identifier, a telephone number or contact name, or the like. Advantageously, the determined location of the device is communicated in conjunction with the classified type of respiratory event to a remote database. This permits automated contact tracing, by geotagging the location of respiratory events, and permits correlation at the database of different device in proximity to the device at the time of an event. Further, the transceiver may track and communicate locations even in the absence of respiratory events, so that lower risk contact situations than cough or sneeze may be monitored. The device may communicate not only respiratory events or other events, but also identifiers of other devices or persons to the database, to provide additional contact information. For example, a speaker recognition system may permit voice identification of proximate persons. The aforementioned location-tagged MAC address may be harvested to determine anonymous or personally identifiable contacts. A device with a camera may capture images of contacts and proximity.

Given the potential availability of retrospective analysis of the data, the database may be analyzed to determine high and low-risk contact situations, and provide population risk information. For example, outdoors proximity of greater than 3 meters is considered low risk, with risks increasing with closer proximity. Likewise, temporal displacements of contacts by more than 4 hours is considered low risk in a dry and sunlit environment. However, retrospective analysis of a central database may permit a quantitative multivariate risk analysis of each contact situation, and alert a user when a high risk situation is predicted to occur, or is occurring, or has occurred. Various approaches to analysis of the data are possible, but key to the analysis is availability of infection data to retrospectively (or in rarer cases, prospectively) tag proximity events, and monitoring of changes in health of a population of users after proximity events. Note that infection data may include PCR viral data, antibody tests, self-reporting, and automated analysis of respiratory events as discloses herein.

The system is not limited to detecting and tracking COVID-19, and rather the respiratory events may be classified to determine influenza, asthma, rhinitis, allergies, chronic obstructive pulmonary disease, certain types of cancer, congestive heart failure, other viruses, bacterial infection, and the like. Therefore, the technology is not limited to a single type of event classification, and can distinguish between different respiratory event etiology in an adaptive manner, even without a precise semantic diagnosis for each. Various types of clustering technology may be useful The programmable processor is provided within a smartphone, smart speaker, IoT device, networked fixed or mobile sensor, or the like.

The at least one automated processor may be further configured to distinguish between a respiratory event of a user of the device and a respiratory event of a non-user of the device comprising performing a third analysis of characteristics of the sound event.

The at least one automated processor may be further configured to determine a location of the device during the respiratory event.

The at least one automated processor may be further configured to classify contingent upon a determination of the commencement of the sound event cycle.

The device may have background execution and foreground execution, wherein the at least one automated processor is further configured to perform the identification and distinguishing between a respiratory event from a non-respiratory event, as background execution of the operating system.

The device may have an operating system, having root execution privileges and user execution privileges, wherein the at least one automated processor is further configured to identify and distinguish between a respiratory event from a non-respiratory event, using instructions executing at the root execution privileges of the operating system.

The at least one automated processor may be further configured to identify using a sound event detection model, being further configured to: perform a spectrographic analysis on received sound signals to produce a spectrogram; analyze the spectrogram with respect to a spectrum model; and apply a frame-wise mask to the analyzed spectrogram.

The at least one automated processor may be further configured to classify using a sound source separation model, being further configured to: perform a spectrographic transform; segment the spectrographic transform; compare the segmented spectrographic transform with a cough sound spectrum and a non-cough sound spectrum; and inverse transforming the segmented spectrographic transform corresponding to the cough sound spectrum.

The at least one automated processor may be further configured to distinguish between the respiratory event of the user of the device and the respiratory event of a non-user of the device, performed using a non-speech source identification model, being further configured to: perform a spectrographic transform; employ a spectrum model; generate an embedded vector output; and perform a database lookup.

The instructions for classifying may comprise instructions for distinguishing between cough, sneeze, and clear throat sounds.

BRIEF DESCRIPTION OF THE DRAWINGS

FIG. 8A shows a probability mask superimposed on the sound wave.

FIG. 8B shows a sound after applying the mask of FIG. 8A.

FIGS. 9A and 9B show 2 STFT spectrums, with spectrum of cough (FIG. 9A) and background environment sound (FIG. 9B), which are the output of FIG. 4.

FIG. 10A shows a sound wave containing the sound of cough and the sounds of the environment. FIG. 10B shows the environmental sound predicted by the model, after applying ISTFT. FIG. 10C show the cough sound predicted by the model after applying ISTFT.

DETAILED DESCRIPTION OF THE PREFERRED EMBODIMENT

Figure 1:
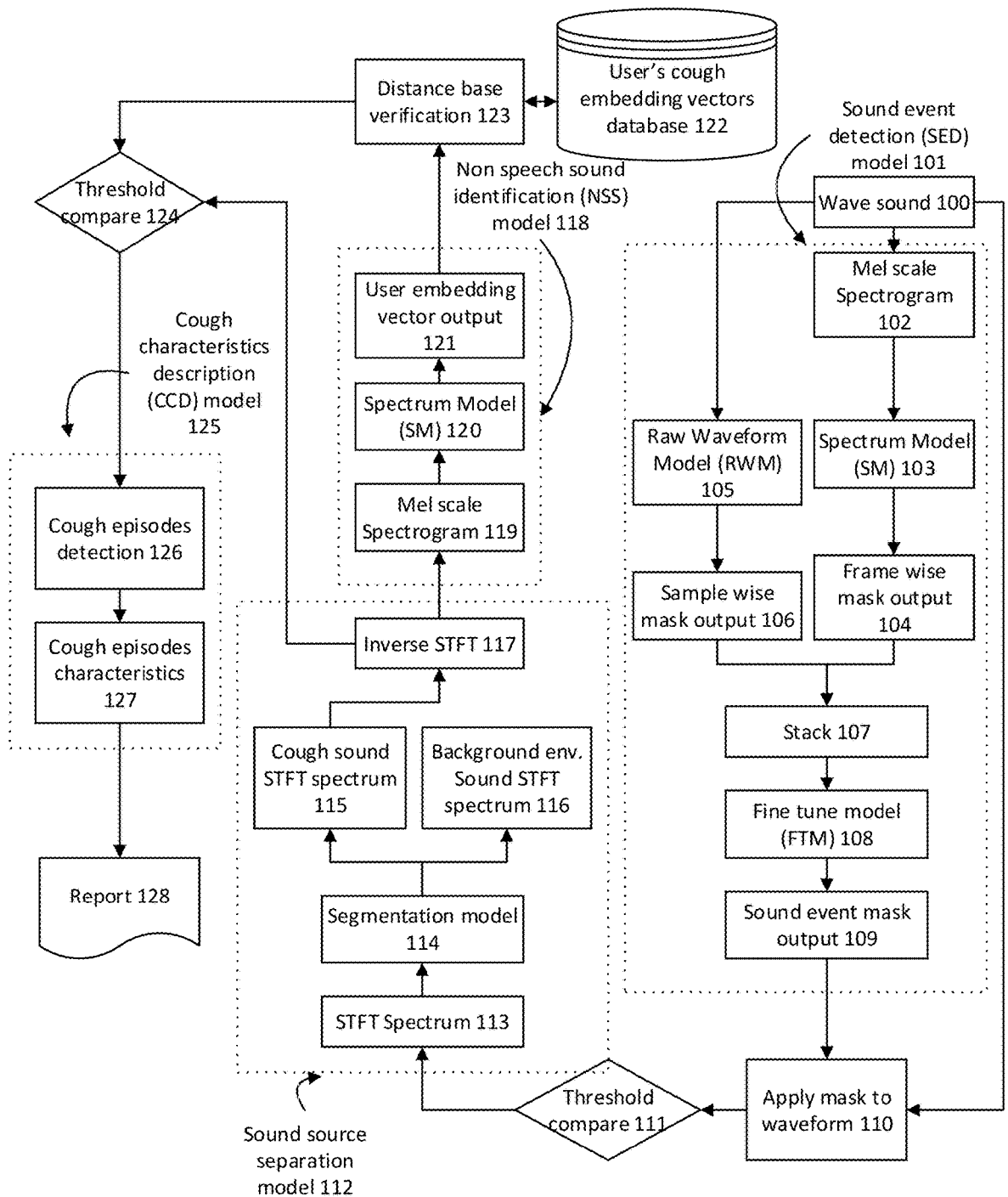
FIG. 1 shows a pipeline general diagram for detecting cough sounds and for cleaning it before analyzing its characteristics. The method consists of several key blocks.

FIG. 1 shows a pipeline general diagram for detecting cough sounds and for cleaning it before analyzing its characteristics. The method consists of several key blocks.

Blocks separated by a dotted line represent a logical combination of operations in the context of one model. Blocks selected with a solid line can represent either an atomic operation, a set of operations, or a machine learning model. The lines with an arrow mark the links in the sequence of Pipeline operations.

Block 101 shows performing event detection of Cough, Sneeze, and Clear Throat (CSC) in incoming sound. Block 112 shows clearing CSC sounds from the background sound environment. Block 118 shows user identification by cough sounds. Block 125 shows detection of cough characteristics. Blocks can either work together or separately on wearable devices, smart devices, personal computers, laptops or on the server.

The processing pipeline receives raw sound 100 at the input, which can be a microphone of a mobile device or computer, or any other sound receiver. On output 128, a detailed report containing the characteristics of the cough.

Figure 2:
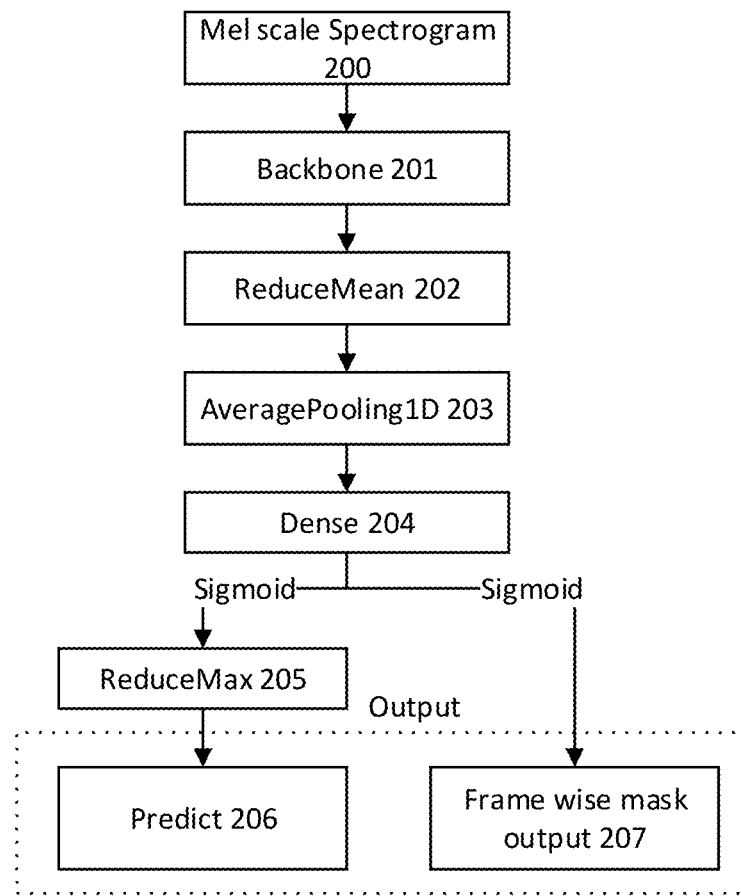
FIG. 2 shows a general diagram of model in FIG. 1.

FIG. 2 shows a general diagram of model 103 in FIG. 1. The model is designed to detect CSC events in the incoming spectrum 200. The model consists of a backbone block, which is a separate neural network and can be any model for working with an image, such as MobileNet, ResNet, InceptionNet, etc. The model has two outputs, the Predict output 206 is a set of CSC classes and is used to train the network. Frame wise mask output 207 is used in the inference stage as a probabilistic mask of CSC events.

FIG. 2 demonstrates an abstract scheme of the neural network, in which a spectrum of sound in mel scale is fed to the input. Backbone block 201 is a neural network that can have any known architecture for image handling, such as MobileNet, ResNet, Inception, EffNet, etc. This is followed by a set of atomic operations ReduceMean, AveragePoolingID. Dense layer is a Multilayer perceptron (MLP) operation. The model has two outputs. The 206 output is a vector with probabilities outside of the time domain. The 207 output is a matrix with probabilities in the time domain.

Figure 3:
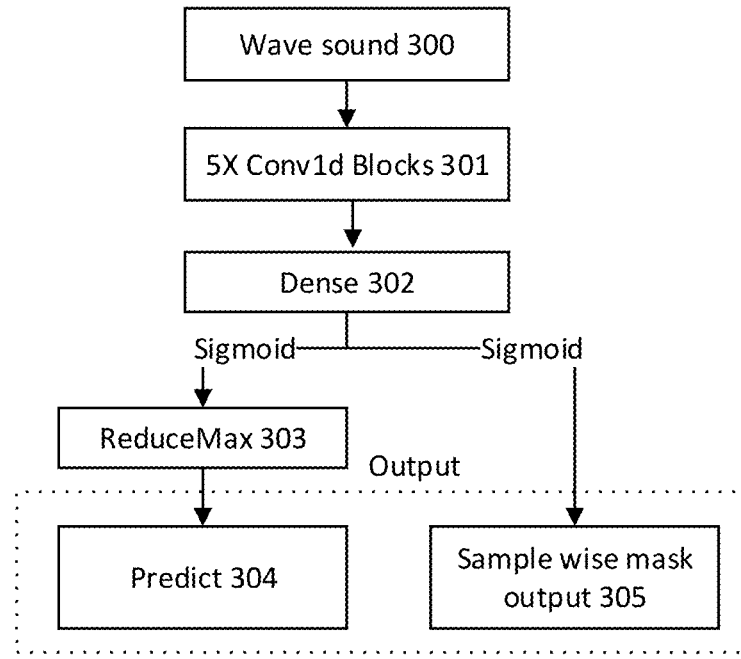
FIG. 3 Shows a general diagram of model in FIG. 1.

FIG. 3 shows a general diagram of model 105 in FIG. 1. The model is designed to detect CSC events in the incoming raw sound 300. The model is a set of Conv1D layers 301 for working with raw sound. Similar to FIG. 2, the model has two outputs Predict 304 which is used for training and Sample wise mask output 305 which is used in the inference stage as a probabilistic mask of CSC events.

FIG. 3 demonstrates an abstract representation of a neural network. A waveform represented by a float vector is fed to the network input 300. Block 301 is a set of consecutive calls of 1D convolutions. Dense layer 302 is a Multilayer perceptron (MLP) operation. The output is similar to that of the FIG. 2 model.

Figure 4:
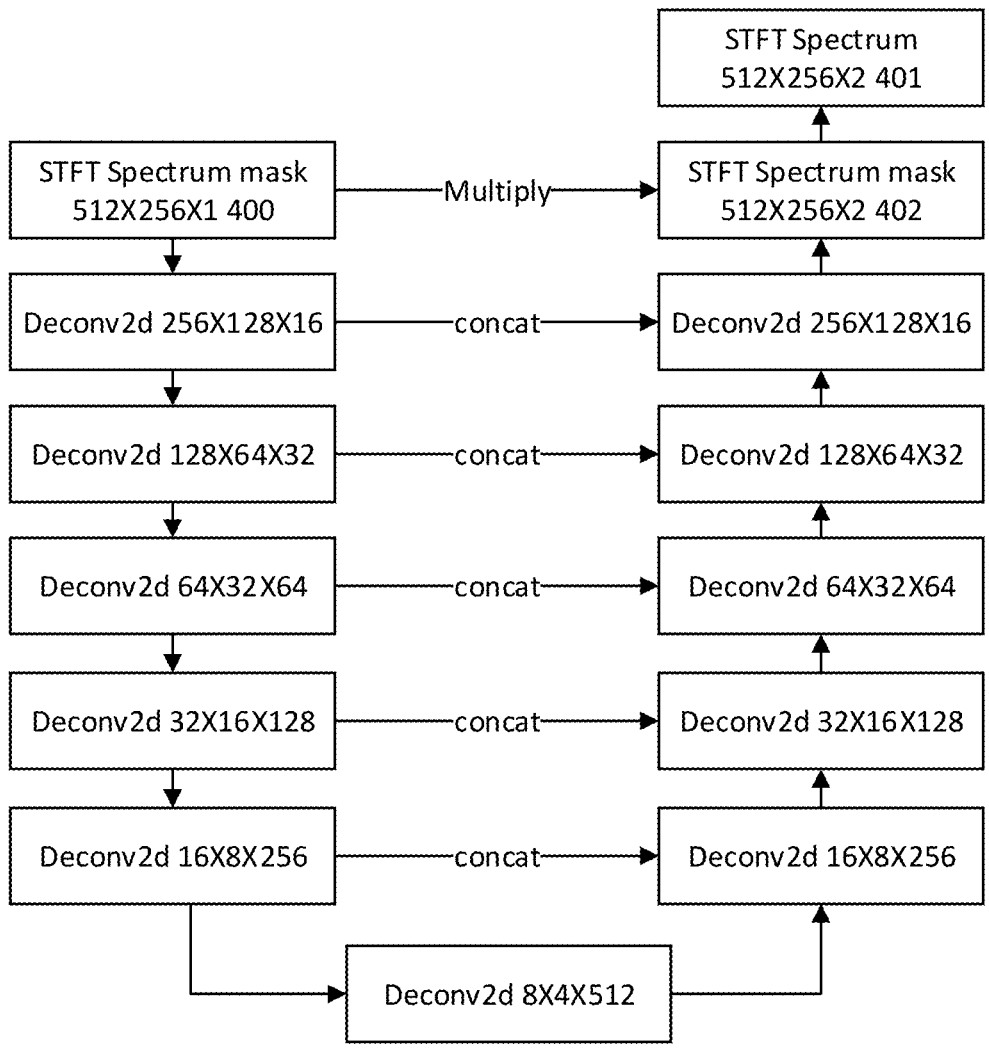
FIG. 4 shows a diagram of model in FIG. 1.

FIG. 4 shows a diagram of model 114 in FIG. 1. The model is designed to separate the sound of coughing from the sound of the environment. It is a U-Net similar architecture. The model accepts as input a Short Time Fourier Transform (STFT) spectrum 400 containing sound that represents the sound of coughing and the sound of the environment. The model is trained to predict the probability channel mask 402 for the input audio spectrum, multiplying this mask by the input spectrum gives the output of the model 401. The first exit channel contains the cough sound spectrum, the second environmental sound spectrum.

FIG. 4 shows a U-Net architecture scheme to separate cough sounds from other sounds. The STFT spectrum of sound containing cough and environmental sounds is fed to input 400. The set of Conv2d and Deconv2d operations, with indicated outgoing dimensions of the tensor, are implemented. The model learns to predict the probability mask 402, which is multiplied by input 400 and the result of multiplication is the 401 output. The network contains a compressive path (left) and an expanding path (right), so the architecture is similar to the letter U, which is reflected in the name. At each step, the number of channels of attributes for the Conv2d operation is doubled. Below the layer name, the output tensor dimension is displayed.

Figure 5:
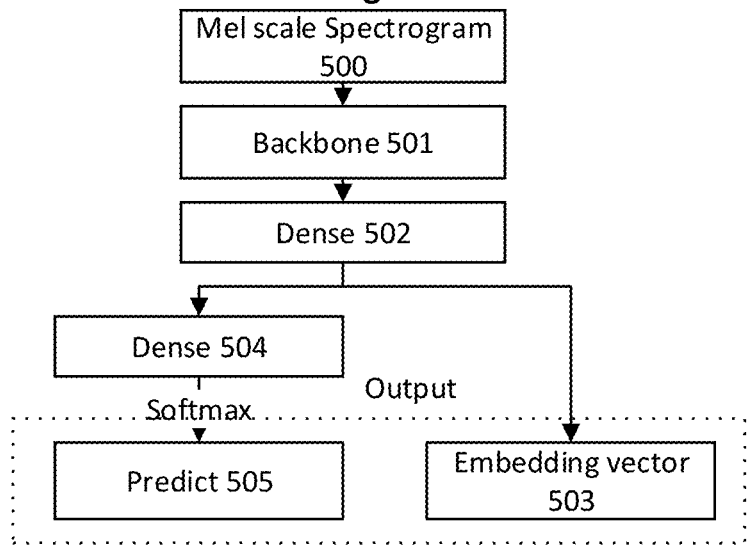
FIG. 5 Diagram of model in FIG. 1.

FIG. 5 shows a diagram of model 120 in FIG. 1. The model is designed to identify the user by the sound of coughing. At the input of the model, a sound with a cough transformed into a Mel scale spectrum 500. Any model for working with images can be used as a backbone block, such as MobileNet, ResNet, InceptionNet, etc. A dense layer 502 is a fully connected neural network block. The model has two outputs Predict 505 and Embedding vector 503. The Predict output is the user ID and is only used to train the model. Embedding vector is a meta-indicative description of a cough sound, the layer has the same dimension as the Dense layer, it is used at the inference stage.

FIG. 5 shows an abstract architecture of the neural network model for user identification by cough sound. Sound spectrum in mel scale 500 is fed to the model input. Backbone block 501 is a neural network that can have any known architecture for image handling, such as MobileNet, ResNet, Inception, EffNet, etc. Dense layers is a Multilayer perceptron (MLP) operation. The model has two outputs. The output 505 is a vector of probability of cough sound belonging to the user, this output is used to training the model. Output 503 is an embedding vector, which is used at an inference stage.

Figure 6:
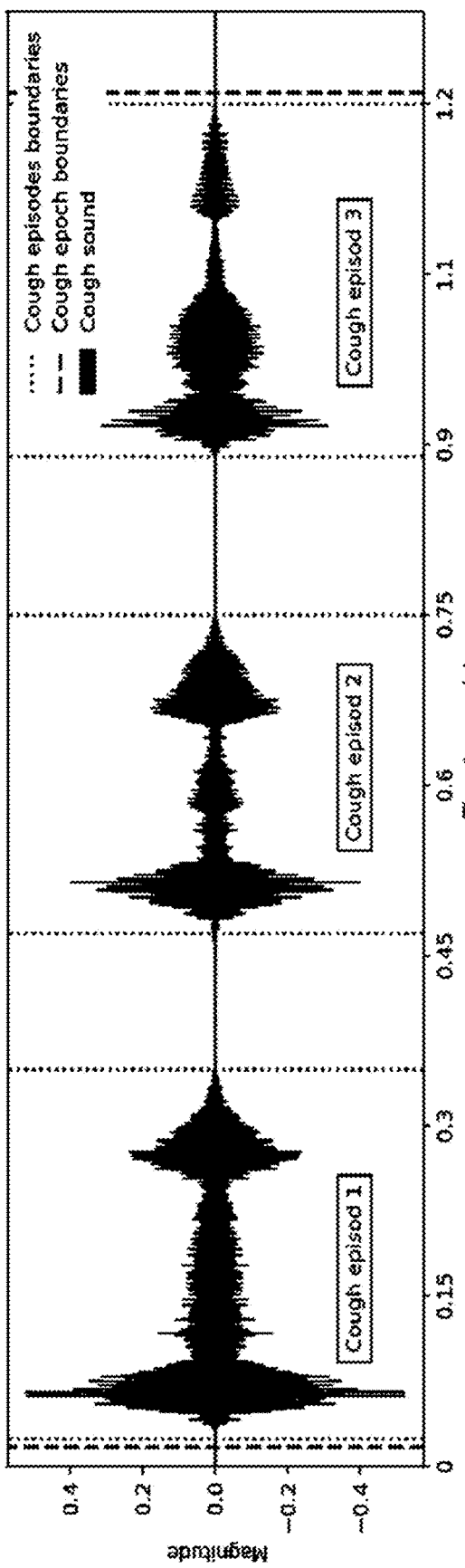
FIG. 6. shows a visual representation of the era of coughing and coughing episodes. Blue indicates a sound wave containing three coughing episodes. The red dotted line indicates the border of the coughing episode. An episode may consist of three or less phases. The whole set of cough episodes in sound is denoted as an epoch. A dotted green line indicates the boundary of the coughing epoch.

FIG. 6 shows a visual representation of the era of coughing and coughing episodes. Blue indicates a sound wave containing three coughing episodes. The red dotted line indicates the border of the coughing episode. An episode may consist of three or less phases. The whole set of cough episodes in sound is denoted as an epoch. A dotted green line indicates the boundary of the coughing epoch.

Figure 7:
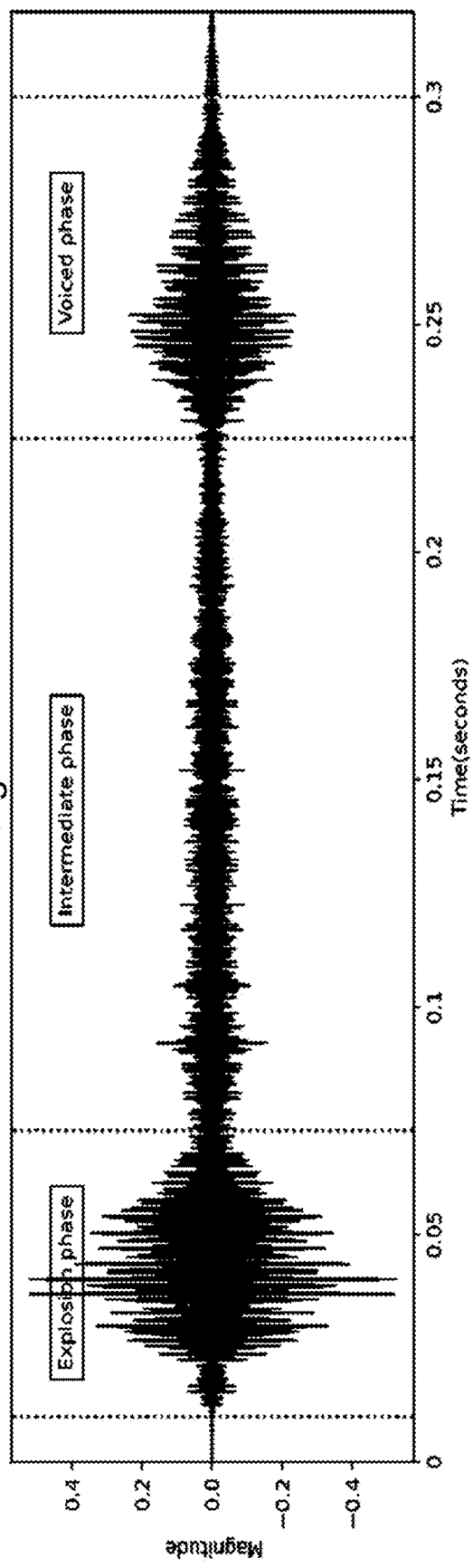
FIG. 7 shows a visual representation of a three-phase cough episode. Vertical dashed lines indicate the phase boundaries. The first phase is called the Explosion phase, the second Intermediate phase, and the third Voiced phase. The first two phases are always present in the cough sound, the third phase may be absent.

FIG. 7 shows a visual representation of a three-phase cough episode. Vertical dashed lines indicate the phase boundaries. The first phase is called the Explosion phase, the second Intermediate phase, and the third Voiced phase. The first two phases are always present in the cough sound, the third phase may be absent.

FIG. 8A shows a probability mask 109 superimposed on the sound wave 100. Blue denotes a sound wave containing coughing sounds as well as environmental sounds. Left X-axis Magnitude of the sound wave. On the right is the probability of a CSC event in the sound. The mask is presented in three classes (Cough, Sneeze, Clear throat). The red dash line shows the likelihood of a coughing event predicted by the SED model 101. The black solid lines indicate the original cough boundaries.

FIG. 8B shows sound after applying the mask of FIG. 8A. Areas of sound with low probability of coughing are filled with zeros. The sound in this form will be sent to the SSS 112 model.

Figure 9B:
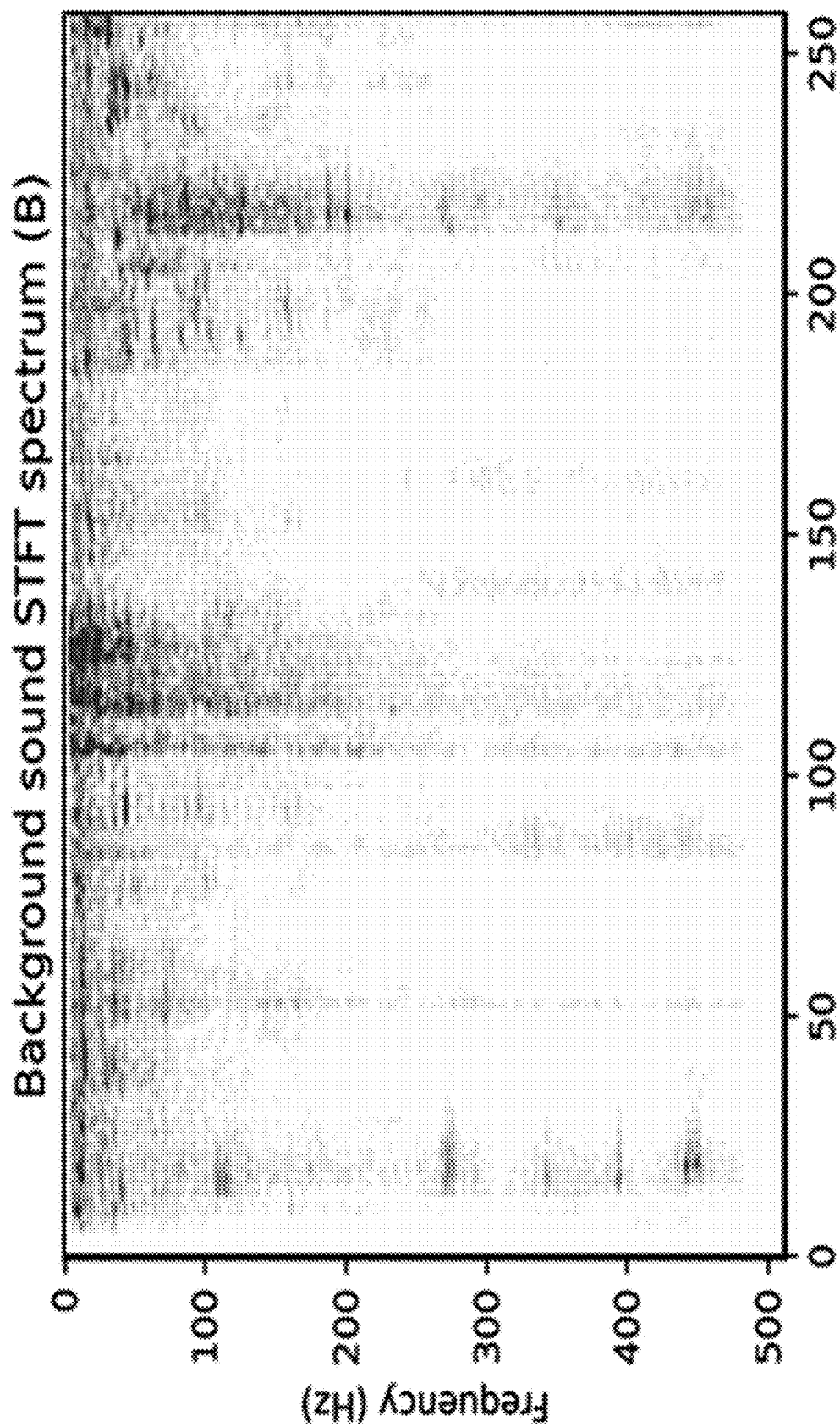

FIGS. 9A and 9B show two Short-time Fourier transform (STFT) spectrums, with spectrum of cough, shown in FIG. 9A and background environment sounds, as shown in FIG. 9B. These spectrums are the output of the FIG. 4. These spectrums can then be restored to a sound wave using Inverse STFT (ISTFT).

Figure 10A:
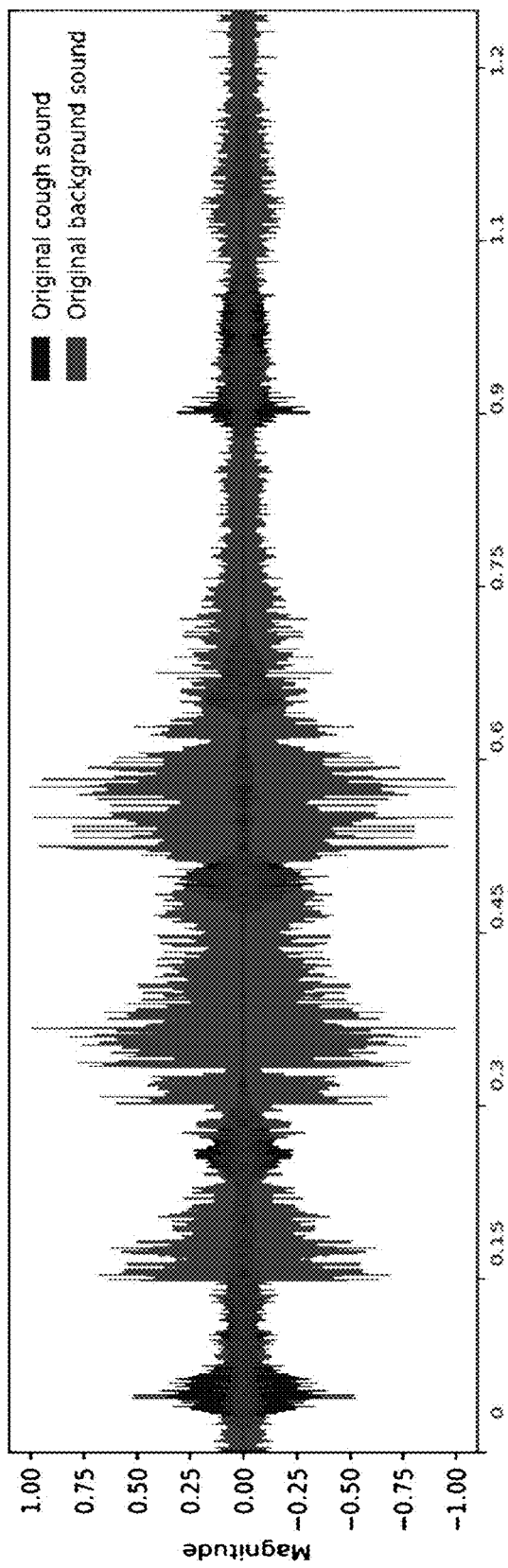
FIGS. 10A-10C shows a decomposition of the sound wave containing cough and environmental sounds into two sounds with and without cough.
Figure 10B:
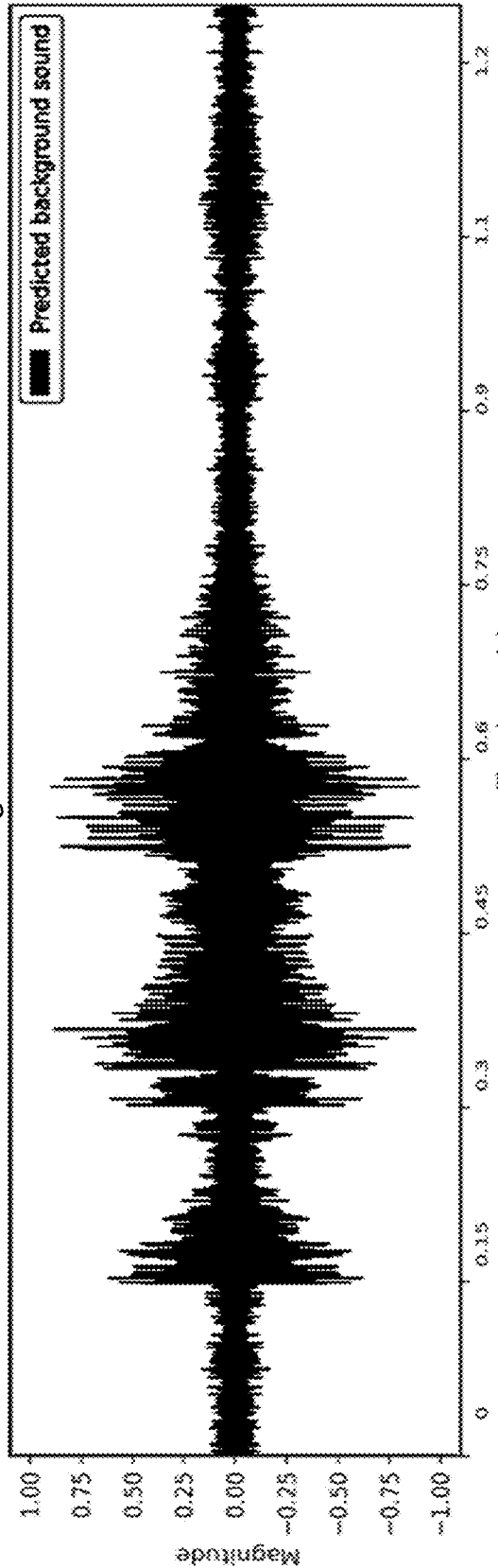
Figure 10C:
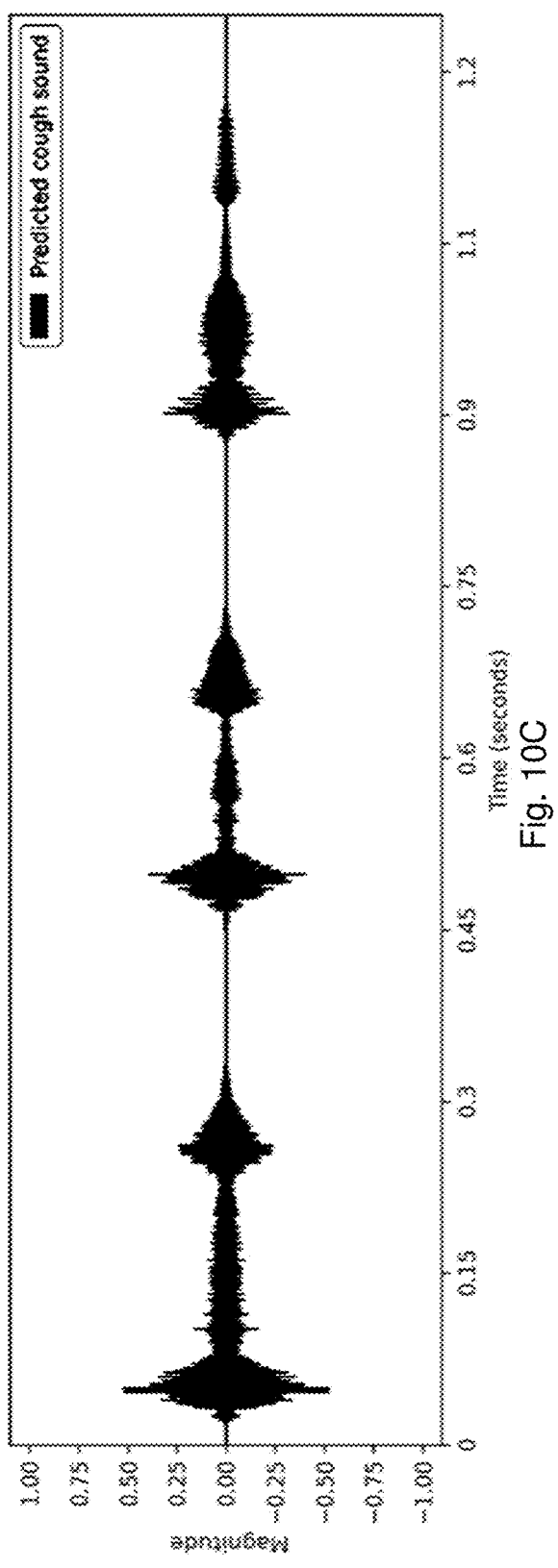

FIGS. 10A-10C show decomposition of the sound wave containing cough and environmental sounds into two sounds with, and without, cough. FIG. 10A shows a sound wave containing the sound of cough and the sounds of the environment. The input sound wave was converted to a spectrum using STFT and sent to the SSS 112 model. The output spectrum were converted back to a sound wave using Inverse STFT (ISTFT). FIG. 10B shows the environmental sound predicted by the model, after applying ISTFT. FIG. 10C shows the cough sound predicted by the model after applying ISTFT.

Figure 11:
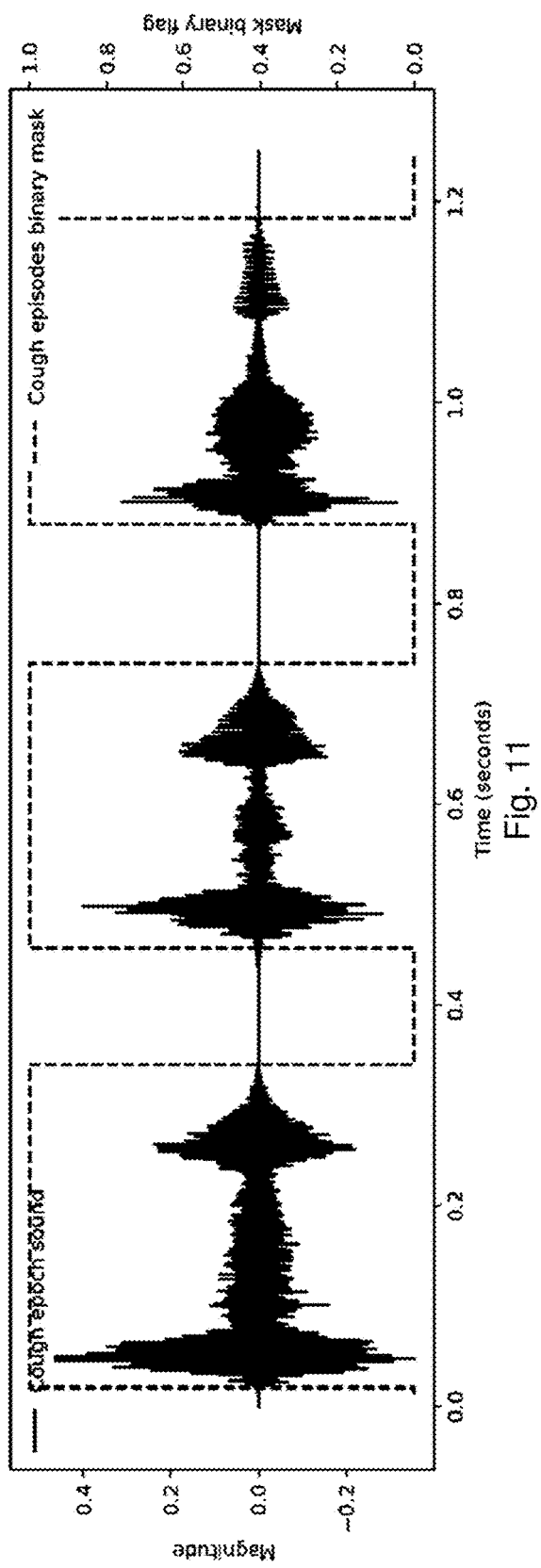
FIG. 11 shows a binary mask separating coughing episodes.

FIG. 11 shows a binary mask separating coughing episodes. The mask is the result of an operation 126 in FIG. 1. The red dot line is a binary mask. It shows the presence of a coughing episode at a time.

Figure 12:
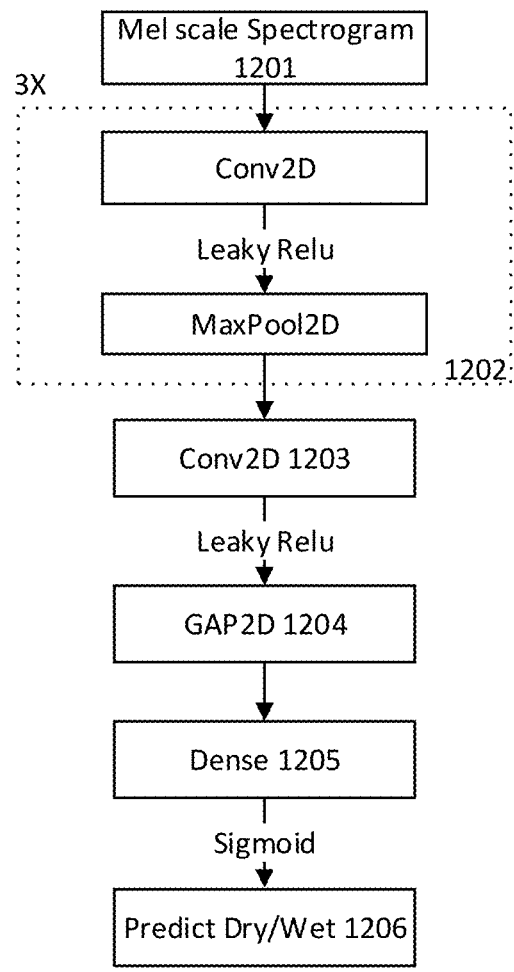
FIG. 12 shows a cough episode classification model on dry/wet.

FIG. 12 shows a cough episode classification model distinguishing dry/wet cough.

The process of extracting cough characteristics from raw sound is represented by several components. Each component is an independent unit capable of operating on both a mobile device and a server.

FIG. 12 shows an abstract architecture of the neural network model for dry wet cough classification. The input 1201 takes the spectrum of sound in the mel scale. Then 3 consecutive operations Conv2D→MaxPool2D. Then Conv2D 1203 and GlobalAveragePooling2D 1204 operations. Dense layers is a Multilayer perceptron (MLP) operation. Predictions 1206 is a probability of wet cough at the model output.

The SED model is designed to detect Cough, Sneeze, Clear Throat (CSC) events in sound. The model has multi label output, it means that the model can correctly process the situation when on one sound segment there are sounds of several classes (for example, after sneezing there is cough). The architecture of the model allows use of weakly labeling data for learning. It is enough just to label if there is a CSC sound on the sound segment, without detailed information about the beginning and end of the segment containing CSC. The model consists of three separate submodels 103, 105, 108 which are trained independently of each other. These models are then combined into one common model 101.

Model 103 in FIG. 2 accepts Mel scale spectrum which is built by operation 102 from incoming raw sound 100 to the input. Any popular neural network architecture such as MobileNet, ResNet, Inception, EfficenceNet, etc. can be used as a Backbone 201. The ReduceMean 202 layer calculates the average for the second dimension of the output from the Backbone. AveragePooling1D 203 averages the value on the channel axis. The Dense 204 layer is a fully connected layer consisting of the number of neurons corresponding to the number of classes. ReduceMax 205 averages the probabilities in the time axis. An Attention operation can be used instead of ReduceMax. The Predict 206 block is an output for ReduceMax operation using this output. After the training, at the inference stage, the Dense block contains a mask consisting of probabilities of SCS classes by time, which is passed to Frame wise mask output 207. The model trained in this way is able to generalize frequency domain features, and time domain features are not taken into account, so the model is not invariant by time. The recognition quality may also depend on the parameters used at conversion of wave sound to Mel scale spectrum. The model output is a probability mask of CSC sounds presence in time FIG. 8 The Model 105 shown in FIG. 3 takes wave sound to the input without pre-processing.

The model consists of five Conv1D blocks. Each block consists of Conv1D, BatchNormalization, Activation operations. As an activation function, any differentiable function can be used, e.g. Relu. Similar to model 103, this model has a Dense 302 layer where data are converted into a probability mask after applying the Sigmoid activation function. The model is trained using the Predict 304 output. Similar to model 105, the second output represents a mask with the same dimension as the model mask 103. Identical dimensions are required to perform the Stack 107 operation which combines the outputs to be sent to the next model. The model is able to generalize the time domain signs, without taking into account the frequency domain signs. The model is invariant by time.

The results of the masks of two models 103 and 105 are combined to train FTM 108. This model consists of only one Conv2D layer, which is fed with the masks of models 103 and 105. The model is designed for weighted probability estimation based on the opinion of two models. As a result of this approach both frequency domain and time domain signs are taken into account. The output of FTM is a mask containing the probability of CSC presence in time.

The SED output is a three-channel mask containing CSC class probabilities, the mask 110 is applied to the incoming sound to get the beginning and end of CSC segments per FIG. 8. Comparison with threshold 111 allows us to conclude that CSC sounds are present in the sound file. The value of the threshold is optimized in the test sample and can change with time as the data volume for training changes. If when comparing a mask with threshold 111, the probability value in the mask is above the threshold, the segments without CSC are filled with zeros as shown in FIG. 8A and the sound is further transmitted to the SSS model FIG. 4.

The existing methods of dividing sound into components (Vocal, Drums, Bass) have recently become actively used in music. A corresponding procedure is employed for dividing the sound of coughing into components (cough sound, the rest of the sound).

The SSS model is designed to separate the cough sound from other sounds. A sound containing cough sounds is fed to the model input. At the output there are two STFT spectra containing only the cough sound (FIG. 9A) and the rest of the sound (FIG. 9B). The SSS model is designed to separate the cough sound from the other sounds. The model is a U-Net architecture. The input model accepts the Short Time Fourier Transform (STFT) spectrum 400 containing the cough sound and any other sounds. The model learns to predict a two-channel mask 402 for the input spectrum, then the mask is multiplied by the input spectrum and fed to the output. By applying Inverse STFT (ISTFT) to each output channel, you can convert the spectrum back to sound. The phase for such conversion is taken from the input sound.

FIGS. 10A-10C show the result of the reverse transformation is presented. FIG. 10A shows the original sound obtained after applying the FIG. 8 probability mask and contains both the cough sound and the surrounding noise. After applying the inverse transformation to FIGS. 9A and 9B spectra, FIG. 10B and FIG. 10C sounds are obtained containing the separated sounds of the environment and cough, respectively. The sound with the cough is completely separated from the rest of the sound. Such a sound does not contain any other information than the sound of the cough itself. Also, the quality of the separation allows you to use this sound for analysis by a specialized expert.

During continuous operation, moments may occur when the detected cough does not belong to the user. For example, a person who is next to the user coughs. The SED model will detect this cough. However, before extracting the characteristics of the detected cough, the source of the cough needs to be identified. A trained model capable of identifying the user by the sound of the cough is therefore provided. Since voice authorization methods have long been used and studied, similar methods may be employed herein, with the cough used instead of voice.

FIG. 5 shows a NSSI model designed to identify the user by the sound of his cough, having a task of sending for analysis the sounds of cough belonging to the user. By the clear sound of the cough it is necessary to determine whether the cough belongs to the user, or to an outsider (for example, someone next to the user coughed). At the input of the model, the sound purified from extraneous noise is yielded, which is then converted into Mel Scale Spectrum 500.

For conversion, the same parameters are used as for the SED model. Any popular architecture (MobileNet, ResNet, Inception, EfficenceNet, etc.) can be used as a backbone 501 network. The Dense 502 layer is a vector that will contain a meta-representation of the cough sound during training. The Predict 505 output, which is used to teach the model, contains the probability that the cough sound belongs to a certain user.

The model trained to classify the user by the sounds of the cough at the Inference stage gives the Embedding vector 503 which is a sign description of a cough. This vector is compared 123 by the closeness metric between vectors from the base 122. This database contains user cough episodes transformed into vectors by the NSSI model. The decision on the user ID 124 is be made when estimating closeness by the distance of the initial vector to the vectors in the database. If the closest vectors in the database belong to the user, the identification is considered passed and the sound sent for further processing of characteristics extraction. If the nearest vectors do not belong to the User, the cough shall be deemed not to belong to the User.

If the cough has been identified, signs are extracted from it for further analysis. The cough epoch may contain several episodes of cough FIG. 6.

A clean cough is sent to the CCD model 125. The CCD model is a set of methods for constructing cough characteristics by estimating its coughing episodes. Coughing episodes are separated by an operation comparing the amplitude to the threshold 126. If the amplitude value is higher than the threshold value, then the cough sound FIG. 11 takes place at that moment.

Block 127 is a set of methods for assessing the length of coughing episodes and such characteristics as dry/wet cough. This block of operations is repeated iteratively for each episode of cough.

The architecture of the model determining the dry/wet characteristic is presented at FIG. 12. A wet cough is characterized by hoarseness usually in the Intermediate phase. The model accepts Mel scale spectrum 1201 containing the sound of one coughing episode as input. Then there is a block of three repeated convolution operations 1202. Global Average Pooling 2D 1204 extract average value from each filter of Conv2D 1203 operation. This is followed by the Dense 1205 layer consisting of 1 neuron, after sigmoid activation the value of this neuron can be interpreted as probability. At the output of the model 1206, the value from zero to one is interpreted as a wet cough probability.

Cough characterization methods may not work correctly if the cough episodes are located too close to each other and the method 126 cannot separate them correctly.

The report 128 can be a convenient format for presenting all collected characteristics, which can be sent either to a professional or used for aggregation over a period of time.

Thus, the illustrative embodiments provide mechanisms for enabling continuous audio monitoring and sound discrimination on a smartphone or smart speaker, along with further actions dependent on detection of trigger sounds, such as cough or sneeze. This functionality is not limited to cough and sneeze detection, and advantageously include other or alternate functions consistent with the discussion herein.

It should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device for monitoring respiratory sounds of a user, comprising:
    a microphone configured to transduce acoustic waves into an electronic stream of audio information;
    a spectrographic transform processor configured to produce a spectrogram from the electronic stream of audio information;
    a trained multilayer perceptron artificial neural network configured to distinguish between cough sounds from the user and cough sounds from a surrounding person using an automated non-speech sound source identification process;
    a user-independent cough data model comprising at least five eigenvectors of a covariance matrix of frequency-based matrix representations corresponding to known sequences of cough sounds within cough cycles;
    at least one automated processor configured to, in real time:
    employ the spectrographic transform processor to determine the frequency domain characteristics of the cough sound event cycle and produce the spectrogram;
    apply a frame-wise mask to the segment the spectrogram to separate the electronic stream of audio information into cough sounds and non-cough sounds, and segment the cough sounds to identify a commencement and a completion of a cough sound event cycle in the cough sounds;
    inverse a transform of the segmented spectrogram corresponding to the cough sounds; and
    employ the trained multilayer perceptron artificial neural network to receive the inversed transform of the spectrogram corresponding to the cough sounds and generate an embedded vector output representing a probability that the cough sounds are from the user as an output, associated with an identity of the user; and
    automatically perform a database lookup based on the identity of the user; and
        an automated classifier trained based on labelled respiratory data, configured to classify a type of respiratory event of the user in real time from a predetermined set of respiratory event classifications dependent on frequency domain characteristics of the sound event cycle and the user independent cough data model, using a neural network classifier executing in real time using root execution privileges of an operating system, trained based on labelled transformed respiratory event data; and
    a radio transmitter, configured to transmit a real-time signal selectively dependent on the classified type of the respiratory event.

2. A method of monitoring respiratory sounds of a user with a device according to claim 1, comprising:
    receiving an audio stream through a microphone configured to transduce acoustic waves into an electronic stream of audio information;
    automatically identifying a commencement and a completion of a cycle of a sound event in the received audio stream with at least one automated processor;
    automatically determining frequency domain characteristics of at least a portion of the sound event with a frequency domain transform;
    automatically distinguishing a respiratory event from a non-respiratory event in the sound event comprising performing a first analysis of the frequency domain characteristics of the sound event with the at least one automated processor;
    automatically classifying a type of respiratory event of the user from a predetermined set of classifications comprising performing a second-analysis of the frequency domain characteristics of the sound event with the at least one automated processor, the classifying being performed by a classifier, trained based on transformed respiratory event data; and
    at least one of outputting and storing the automatically classified type of respiratory event of the user,
    wherein the device is a smartphone having an operating system, having background execution, foreground execution, root execution privileges, and user execution privileges,
    wherein at least the automatically identifying and automatically distinguishing a respiratory event from a non-respiratory event, are performed as background execution of the operating system; and
    wherein at least the automatically identifying and automatically distinguishing a respiratory event from a non-respiratory event, are performed with the root execution privileges of the operating system.

3. The device according to claim 2, wherein the classifier is further configured to automatically classify the type of respiratory event selectively contingent upon determination of the commencement of the sound event cycle.

4. The device according to claim 1, wherein the respiratory event comprises a cough, and the classified type of respiratory event is selected from the group comprising a cough of a COVID-19 person and a cough of a COVID-19 negative person.

5. The device according to claim 1, further comprising a global positioning system, wherein the at least one automated processor is further configured to automatically determine a geolocation of the device during the respiratory event based on an output of the global positioning system.

6. The device according to claim 1, wherein the at least one automated processor is part of a smartphone having an operating system, having background execution and foreground execution, wherein at least the at least one automated processor is configured to distinguish a respiratory event from a non-respiratory event, by background execution of the operating system.

7. The device according to claim 1, wherein the at least one automated processor executes an operating system of a smartphone having the root execution privileges and the user execution privileges, wherein the at least one automated processor is further configured to selectively determine which resources of the smartphone to employ at a given time.

8. The device according to claim 1, wherein the classifier is trained to selectively distinguish between cough, sneeze, and clear throat type of respiratory events.

9. The device according to claim 1, further comprising a wavelet transform configured to separate impulsive sound components of the electronic stream of audio information, wherein the at least one automated processor is further configured to automatically sort wavelet coefficient sets of the wavelet transform according to statistical parameters of each respective wavelet coefficient set.

10. The device according to claim 1, wherein the programmable processor is provided within at least one of a smartphone and a smart speaker.

11. The device according to claim 1, further comprising:
an automated geolocation system for determining a location of the device; and
a radio frequency transceiver configured to communicate the determined location of the device in conjunction with the classified type of respiratory event from the radio transmitter to a remote database.

12. The device according to claim 1, wherein the spectrographic transform comprises a Short Time Fourier Transform (STFT) spectrum, and at least one automated processor executes an operating system having root execution privileges and user execution privileges, configured to execute at least the automatic generation of the embedded vector output with the root execution privileges.

13. The device according to claim 1, further comprising a radio proximity detector configured to determine an identity of, a distance to, and a duration of proximity to, a remote radio frequency transceiver.

14. The device according to claim 1, wherein the at least one processor is further configured to determine a path of the device, and to determine a temporal and spatial proximity of another device with respect to the path.

15. A device for monitoring respiratory sounds of a user comprising respiratory events, comprising:
a microphone configured to transduce acoustic waves into an electronic stream of audio information;
at least one automated processor, configured to, in real time:
implement a user-independent cough data model comprising at least five eigenvectors of a covariance matrix of frequency-based matrix representations corresponding to known sequences of cough sounds within cough cycles;
automatically perform a spectrographic transform to determine the frequency domain characteristics of the cough sound event cycle;
segment the spectrographic transform of the cough sound event cycle;
compare the segmented spectrographic transform with a cough sound spectrum and a non-cough sound spectrum;
separate the audio information into spectrographic transform representations of cough sounds and non-cough sounds;
perform an inverse spectrographic transform on the spectrographic transform representations of the cough sounds;
identify a commencement and a completion of a cough sound event cycle in the cough sounds of the inverse spectrographic transform on the spectrographic transform representations of the cough sounds
automatically generate an embedded vector output as an output of a multilayer perceptron neural network, associated with an identity of the user and representing a probability that the cough sounds are from the user;
automatically perform a database lookup, to automatically distinguish between cough sounds from the user and cough sounds from a surrounding person, using an automated non-speech sound source identification process;
classify a type of respiratory event of the user from a predetermined set of classifications using a sound source separation model, using a neural network classifier, trained based on labelled transformed respiratory event data; and
a radio transmitter, configured to transmit a signal selectively dependent on the classified type of the respiratory event,
wherein the at least one automated processor is configured to distinguish between the cough sounds from the user and cough sounds from the surrounding person in real time using the automated non-speech sound source identification process, executable with the root execution privileges of an operating system controlling the at least one automated processor, and transmit the signal through the radio transmitter in real-time.

16. The device according to claim 15, wherein the at least one automated processor is further configured to perform a frequency domain transform as an automated Short Time Fourier Transform, to automatically distinguish a respiratory event of a user of the device in real-time.

17. The device according to claim 15, wherein the at least one automated processor is further configured to identify the commencement and the completion of the cough sound event cycle by automatic application of a frame-wise mask to the frequency domain characteristics of the cough sound event cycle, to automatically identify the commencement and completion of the cough sound event cycle.

18. The device according to claim 15, further comprising a geolocator configured to determine a geolocation of the device over time, wherein the at least one processor is configured to generate the signal comprising a location of the device at a time of a respiratory event, a classification of the type of respiratory event, and whether the respiratory event comprises cough sounds from the user or cough sounds from the surrounding person.

19. The device according to claim 18, further comprising a plurality of different communication transceivers, wherein the at least one automated processor is further configured to selectively determine which respective communication transceiver to employ to transmit the signal.

20. The device according to claim 15, wherein the at least one automated processor is configured to execute the operating system of a smartphone having root execution privileges and user execution privileges.

* * * * *